(12) United States Patent
Yokokawa et al.

(10) Patent No.: US 10,526,266 B2
(45) Date of Patent: Jan. 7, 2020

(54) ACTINIC RAY-SENSITIVE OR RADIATION-SENSITIVE RESIN COMPOSITION, ACTINIC RAY-SENSITIVE OR RADIATION-SENSITIVE FILM, MASK BLANK PROVIDED WITH ACTINIC RAY-SENSITIVE OR RADIATION-SENSITIVE FILM, PHOTOMASK, PATTERN FORMING METHOD, METHOD FOR MANUFACTURING ELECTRONIC DEVICE, ELECTRONIC DEVICE, COMPOUND, AND METHOD FOR PRODUCING COMPOUND

(71) Applicant: FUJIFILM Corporation, Tokyo (JP)

(72) Inventors: Natsumi Yokokawa, Shizuoka (JP);
Hidehiro Mochizuki, Shizuoka (JP);
Koutarou Takahashi, Shizuoka (JP);
Shuhei Yamaguchi, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/176,762

(22) Filed: Jun. 8, 2016

(65) Prior Publication Data

US 2016/0280621 A1 Sep. 29, 2016

Related U.S. Application Data

(63) Continuation of application No. PCT/JP2014/082435, filed on Dec. 8, 2014.

(30) Foreign Application Priority Data

Feb. 5, 2014 (JP) .................. 2014-020781

(51) Int. Cl.
| | | |
|---|---|---|
| *G03F 1/50* | (2012.01) | |
| *G03F 1/76* | (2012.01) | |
| *G03F 7/004* | (2006.01) | |
| *G03F 7/038* | (2006.01) | |
| *G03F 7/32* | (2006.01) | |
| *G03F 7/20* | (2006.01) | |
| *C07C 41/09* | (2006.01) | |
| *C07C 41/22* | (2006.01) | |
| *C07C 41/14* | (2006.01) | |
| *C07C 43/178* | (2006.01) | |
| *C07D 239/10* | (2006.01) | |

(52) U.S. Cl.
CPC .......... *C07C 43/1788* (2013.01); *C07C 41/09* (2013.01); *C07C 41/14* (2013.01); *C07C 41/22* (2013.01); *C07D 239/10* (2013.01); *G03F 1/50* (2013.01); *G03F 1/76* (2013.01); *G03F 7/0045* (2013.01); *G03F 7/0046* (2013.01); *G03F 7/038* (2013.01); *G03F 7/0382* (2013.01); *G03F 7/2059* (2013.01); *G03F 7/322* (2013.01); *G03F 7/325* (2013.01)

(58) Field of Classification Search
CPC ......... C07C 41/09; C07C 41/22; C07C 41/14; C07C 43/23; C07C 43/1788; C07D 239/10; G03F 7/0382; G03F 7/0046; G03F 7/0045; G03F 7/038; G03F 7/322; G03F 7/2059; G03F 7/325
See application file for complete search history.

(56) References Cited

U.S. PATENT DOCUMENTS 4,387,152 A * 6/1983 Stahlhofen ............ G03F 7/0045
430/191
5,217,840 A * 6/1993 Spak .................... G03F 7/0226
430/165
(Continued)

FOREIGN PATENT DOCUMENTS

| CN | 103460133 A | 12/2013 | |
|---|---|---|---|
| JP | 11-102071 | * 4/1999 | ............. G03F 7/038 |

(Continued)

OTHER PUBLICATIONS machine translation of JP 2002-099085 (2002).*
machine translation of JP 2009-042752 (2009).*
Machine translation of JP 2009-237167 (2009).*
Communication dated Feb. 14, 2017, issued by the Japan Patent Office in corresponding Japanese Application No. 2014-020781.
International Preliminary Report on Patentability dated Aug. 9, 2016, in International Application No. PCT/JP2014/082435, with English translation of Written Opinion, 18 pages in English and Japanese.
International Search Report for PCT/JP2014/082435 dated Mar. 10, 2015 [PCT/ISA/210].

(Continued)

*Primary Examiner* — Martin J Angebranndt
(74) *Attorney, Agent, or Firm* — Sughrue Mion, PLLC

(57) ABSTRACT

The composition contains an alkali-soluble resin and a crosslinking agent that is represented by the following General Formula (I). In the formula, each of $R_1$ and $R_6$ independently represents a hydrogen atom or a hydrocarbon group having 5 or less carbon atoms; each of $R_2$ and $R_5$ independently represents an alkyl group, a cycloalkyl group, an aryl group, or an acyl group; and each of $R_3$ and $R_4$ independently represents a hydrogen atom or an organic group having 2 or more carbon atoms, and $R_3$ and $R_4$ may be bonded to each other to form a ring.

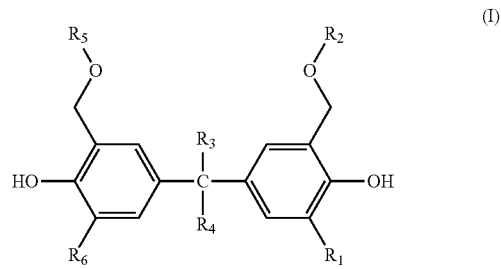

20 Claims, 2 Drawing Sheets

(56) References Cited

U.S. PATENT DOCUMENTS

| | | | | |
|---|---|---|---|---|
| 6,773,862 | B2* | 8/2004 | Shirakawa | G03F 7/0045 430/270.1 |
| 9,718,901 | B2* | 8/2017 | Tsuruta | C08F 12/24 |
| 2003/0124456 | A1* | 7/2003 | Shirakawa | G03F 7/0045 430/270.1 |
| 2004/0033441 | A1* | 2/2004 | Yasunami | G03F 7/0382 430/270.1 |
| 2007/0122733 | A1* | 5/2007 | Hattori | G03F 7/0233 430/141 |
| 2009/0181224 | A1* | 7/2009 | Minegishi | G03F 7/0226 428/201 |
| 2010/0092879 | A1* | 4/2010 | Minegishi | C08G 69/26 430/18 |
| 2010/0159217 | A1* | 6/2010 | Minegishi | C08L 79/08 428/201 |
| 2012/0115084 | A1* | 5/2012 | Okuyama | G03F 7/0382 430/281.1 |
| 2012/0214091 | A1* | 8/2012 | Tsuchimura | G03F 1/50 430/5 |
| 2012/0219888 | A1* | 8/2012 | Masunaga | G03F 7/0045 430/5 |
| 2013/0017376 | A1* | 1/2013 | Okuyama | G03F 7/0382 428/195.1 |
| 2014/0120462 | A1* | 5/2014 | Minegishi | C08G 73/22 430/18 |
| 2014/0234777 | A1* | 8/2014 | Sakurai | G03F 7/0226 430/286.1 |
| 2014/0242502 | A1* | 8/2014 | Tsuchimura | C08F 12/22 430/5 |
| 2016/0282720 | A1* | 9/2016 | Takahashi | G03F 7/0382 |

FOREIGN PATENT DOCUMENTS

| | | | | | |
|---|---|---|---|---|---|
| JP | 2000-1448 | A | | 1/2000 | |
| JP | 2002-099085 | | * | 4/2002 | |
| JP | 2002-99085 | A | | 4/2002 | |
| JP | 2002-169283 | | * | 6/2002 | |
| JP | 2002-372783 | A | | 12/2002 | |
| JP | 2006-313237 | | * | 11/2006 | |
| JP | 2008158263 | A | | 7/2008 | |
| JP | 2008-233363 | A | | 10/2008 | |
| JP | 2008-273844 | A | | 11/2008 | |
| JP | 2009-042752 | | * | 2/2009 | |
| JP | 2009-175357 | | * | 8/2009 | G03F 7/023 |
| JP | 2009-175357 | A | | 8/2009 | |
| JP | 2009-237167 | | * | 10/2009 | G03F 7/038 |
| JP | 2009-258634 | A | | 11/2009 | |
| JP | 2009-265445 | A | | 11/2009 | |
| JP | 2009-265520 | | * | 11/2009 | |
| JP | 2012-063788 | | * | 3/2012 | |
| JP | 2012-203238 | | * | 10/2012 | |
| JP | 2012-226297 | | * | 11/2012 | |
| JP | 2013-003310 | | * | 1/2013 | |
| JP | 2013-156388 | A | | 8/2013 | |
| JP | 2014-186300 | A | | 10/2014 | |
| TW | 201433880 | A | | 9/2014 | |
| WO | 2013/069812 | | * | 5/2012 | G03F 7/004 |
| WO | 2012/172793 | | * | 12/2012 | G03F 7/023 |
| WO | 2013/176063 | | * | 11/2013 | G03F 7/038 |

OTHER PUBLICATIONS

Written Opinion for PCT/JP2014/082435 dated Mar. 10, 2015 [PCT/ISA/237].

Communication dated Apr. 21, 2017, issued by the Korean Intellectual Property Office in corresponding Korean Application No. 10-2016-7015190.

Office Action dated Oct. 25, 2017 from the Taiwanese Intellectual Property Office in counterpart Taiwanese Application No. 103144195.

Office Action dated Oct. 12, 2017 from the Korean Intellectual Property Office in counterpart Korean Application No. 10-2016-7015190.

Office Action dated Feb. 7, 2018 from the Taiwanese Patent Office in counterpart Taiwanese Application No. 103144195.

Communication dated Mar. 26, 2019 from the State Intellectual Property Office of the P.R.C. in counterpart Chinese Application No. 201480070130.0.

Office Action dated Sep. 12, 2019 from the State Intellectual Property Office of the People's Republic of China in counterpart Chinese Application No. 201480070130.0.

* cited by examiner

ACTINIC RAY-SENSITIVE OR RADIATION-SENSITIVE RESIN COMPOSITION, ACTINIC RAY-SENSITIVE OR RADIATION-SENSITIVE FILM, MASK BLANK PROVIDED WITH ACTINIC RAY-SENSITIVE OR RADIATION-SENSITIVE FILM, PHOTOMASK, PATTERN FORMING METHOD, METHOD FOR MANUFACTURING ELECTRONIC DEVICE, ELECTRONIC DEVICE, COMPOUND, AND METHOD FOR PRODUCING COMPOUND

CROSS-REFERENCE TO RELATED APPLICATIONS

This application is a Continuation of PCT International Application No. PCT/JP2014/82435, filed on Dec. 8, 2014, which claims priority under 35 U.S.C. § 119(a) to Japanese Patent Application No. 2014-020781, filed on Feb. 5, 2014. Each of the above application(s) is hereby expressly incorporated by reference, in its entirety, into the present application.

BACKGROUND OF THE INVENTION

1. Field of the Invention

The present invention relates to an actinic ray-sensitive or radiation-sensitive resin composition which is suitably used for ultramicrolithographic processes for the production of ultra-large scale integrations (LSIs) or high-capacity microchips, or other fabrication processes, and with which high precision patterns can be formed using an electron beam or extreme ultraviolet rays, as well as an actinic ray-sensitive or radiation-sensitive film, a mask blank provided with the actinic ray-sensitive or radiation-sensitive film a photomask, a pattern forming method, a method for manufacturing an electronic device, an electronic device, a novel compound, and a method for producing the novel compound, each using the composition. More particularly, the invention relates to an actinic ray-sensitive or radiation-sensitive resin composition which is suitably used for a process of using a substrate having a specific underlying film, as well as an actinic ray-sensitive or radiation-sensitive film, a mask blank provided with the actinic ray-sensitive or radiation-sensitive film a photomask, a pattern forming method, a method for manufacturing an electronic device, an electronic device, a novel compound, and a method for producing the novel compound, each using the composition.

2. Description of the Related Art

In the process of producing a semiconductor device such as an IC or an LSI, microfabrication by lithography using a photoresist composition has been conventionally performed and correspondingly the development of a resin or additive suitable for a variety of lithographic technologies is currently underway. For example, JP2008-273844A and JP2000-1448A disclose additives suitable for lithographic technologies.

Recently, the integration degree of an integrated circuit has been becoming higher and consequently formation of an ultrafine pattern in the sub-micron or quarter-micron range has been required. To cope with this requirement, the exposure wavelength has also tended to become shorter, for example, from g line to i line or further to excimer laser light. At present, the development of lithography using an electron beam or X-rays is also proceeding.

Lithography using an electron beam, X-rays, or EUV light is positioned as a next-generation or next-next-generation pattern formation technique, and a high-sensitivity high-resolution resist composition is required. As a resist composition suitable for negative lithography, a so-called negative chemical amplification resist composition which includes an alkali-soluble resin, a crosslinking agent, and an acid generator as main components has been effectively used (see, for example, JP2002-99085A).

However, from the viewpoint of overall performance as the resist, it remains very difficult to find a suitable combination of a resin, a photoacid generator, a basic compound, an additive, a solvent, and the like to be used. In addition, when forming an ultrafine pattern such as one having a line width of 50 nm or less, there is also a need for an improvement in PEB temperature dependency or an improvement in storage stability of a resist solution since the line width of the pattern varies depending on the temperature of heating after the irradiation of actinic rays or radiation (post exposure bake: PEB).

SUMMARY OF THE INVENTION

As an additive which is suitable for lithographic technologies, for example, JP2008-273844A discloses a fluorene compound having a phenolic hydroxyl group and a hydroxymethyl group, and JP2000-1448A discloses a compound having a structure in which two phenolic nuclei having a cyclohexyl group and a hydroxymethyl group or an alkoxymethyl group as substituents are symmetrically bonded via a cyclohexylidene group. When the present inventors have used these compounds in the resist composition as a crosslinking agent, the present inventors could not achieve the storage stability for the resist solution required in the case of forming an ultrafine pattern (for example, in particular, one having a line width of 50 nm or less). In addition, reduction in PEB temperature dependency in line width variation of a pattern did not reach a satisfactory level.

An object of the present invention is to provide an actinic ray-sensitive or radiation-sensitive resin composition which is capable of reducing line width variation in a pattern dependent on the PEB temperature during the formation of an ultrafine pattern (for example, one having a line width of 50 nm or less), and which also has excellent storage stability, as well as an actinic ray-sensitive or radiation-sensitive film, a mask blank provided with the same film, a photomask, a pattern forming method, a method for manufacturing an electronic device, and an electronic device, each using the composition. Another object of the present invention is to provide a novel compound which can be suitably used in the above-mentioned actinic ray-sensitive or radiation-sensitive resin composition, and a method for producing the same compound.

In an embodiment, the present invention is as follows.

[1] An actinic ray-sensitive or radiation-sensitive resin composition comprising an alkali-soluble resin and a crosslinking agent, wherein the crosslinking agent is represented by the following General Formula (I).

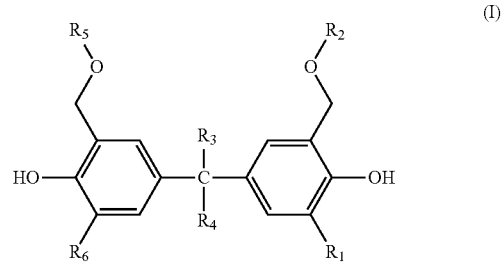

In General Formula (1), each of $R_1$ and $R_6$ independently represents a hydrogen atom, or a hydrocarbon group having 5 or less carbon atoms.

Each of $R_2$ and $R_5$ independently represents an alkyl group, a cycloalkyl group, an aryl group, or an acyl group.

Each of $R_3$ and $R_4$ independently represents a hydrogen atom, or an organic group having 2 or more carbon atoms. $R_3$ and $R_4$ may be bonded to each other to form a ring.

[2] The actinic ray-sensitive or radiation-sensitive resin composition according to [1], wherein $R_3$ and $R_4$ in General Formula (I) are bonded to each other to form a ring.

[3] The actinic ray-sensitive or radiation-sensitive resin composition according to [2], wherein $R_3$ and $R_4$ in General Formula (I) are bonded to each other to form a ring represented by the following General Formula (I-a).

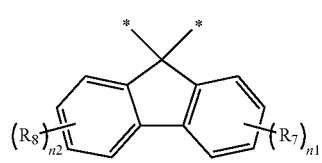

(I-a)

In General Formula (I-a), each of $R_7$ and $R_8$ independently represents a substituent. Each of n1 and n2 independently represents an integer of 0 to 4.

\* indicates a connecting site to the phenolic nucleus.

[4] The actinic ray-sensitive or radiation-sensitive resin composition according to any one of [1] to [3], wherein the alkali-soluble resin is a resin having a repeating unit represented by the following General Formula (1).

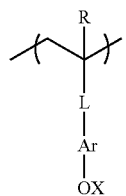

(1)

In General Formula (1),

R represents a hydrogen atom or a methyl group.

X represents a group having a non-acid-decomposable hydrocarbon group.

Ar represents an aromatic ring.

L represents a divalent linking group.

[5] The actinic ray-sensitive or radiation-sensitive resin composition according to any one of [1] to [4], further comprising a compound capable of generating an acid upon irradiation with actinic rays or radiation.

[6] The actinic ray-sensitive or radiation-sensitive resin composition according to [5], wherein the compound capable of generating an acid upon irradiation with actinic rays or radiation is an onium salt.

[7] The actinic ray-sensitive or radiation-sensitive resin composition according to [5] or [6], wherein the compound capable of generating an acid upon irradiation with actinic rays or radiation is a compound capable of generating an acid represented by the following General Formula (IIIB) or (IVB).

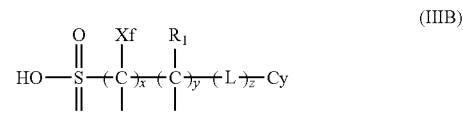

(IIIB)

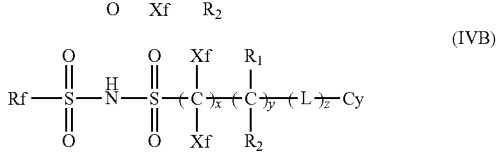

(IVB)

In General Formula (IIIB), each Xf independently represents a fluorine atom, or an alkyl group substituted with at least one fluorine atom.

Each of $R_1$ and $R_2$ independently represents a hydrogen atom, or an alkyl group.

Each L independently represents a divalent linking group.

Cy represents a cyclic organic group.

x represents an integer of 1 to 20, y represents an integer of 0 to 10, and z represents an integer of 0 to 10.

In General Formula (IVB), each Xf independently represents a fluorine atom, or an alkyl group substituted with at least one fluorine atom.

Each of $R_1$ and $R_2$ independently represents a hydrogen atom, or an alkyl group.

Each L independently represents a divalent linking group.

Cy represents a cyclic organic group.

Rf represents a group containing a fluorine atom.

x represents an integer of 1 to 20, y represents an integer of 0 to 10, and z represents an integer of 0 to 10.

[8] An actinic ray-sensitive or radiation-sensitive film formed by using the actinic ray-sensitive or radiation-sensitive resin composition according to any one of [1] to [7].

[9] A mask blank provided with the actinic ray-sensitive or radiation-sensitive film according to [8].

[10] A photomask produced by a method including exposing the actinic ray-sensitive or radiation-sensitive film provided in the mask blank according to [9] to light, and developing the exposed actinic ray-sensitive or radiation-sensitive film.

[11] A pattern forming method, comprising:

forming an actinic ray-sensitive or radiation-sensitive film using the actinic ray-sensitive or radiation-sensitive resin composition according to any one of [1] to [7];

exposing the film and developing the exposed film using a developer to form a pattern.

[12] The pattern forming method according to [11], wherein the exposure is carried out using X-rays, an electron beam, or EUV.

[13] A method for manufacturing an electronic device, comprising the pattern forming method according to [11] or [12].

[14] An electronic device manufactured by the method for manufacturing an electronic device according to [13].

[15] A compound represented by the following General Formula (I-b).

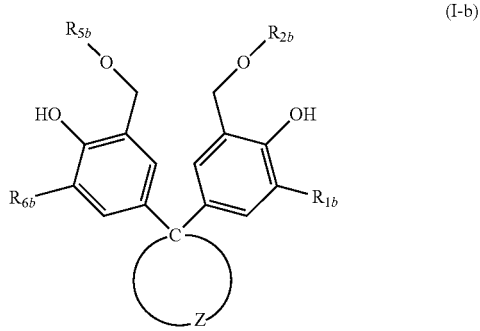

In General Formula (I-b),
each of $R_{1b}$ and $R_{6b}$ independently represents an alkyl group having 5 or less carbon atoms.
Each of $R_{2b}$ and $R_{5b}$ independently represents an alkyl group having 6 or less carbon atoms or a cycloalkyl group having 3 to 12 carbon atoms.
Z represents an atomic group necessary for forming a ring together with the carbon atom in the formula.

[16] A method for producing the compound represented by the following General Formula (I), comprising using a compound represented by the following General Formula (I-c) as a raw material.

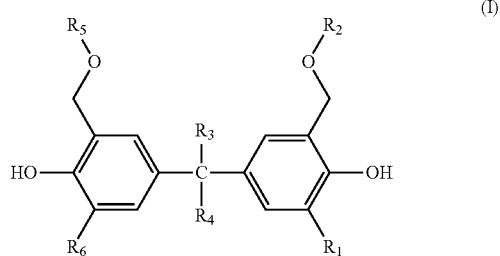

In General Formula (I),
each of $R_1$ and $R_6$ independently represents a hydrogen atom, or a hydrocarbon group having 5 or less carbon atoms.
Each of $R_2$ and $R_5$ independently represents an alkyl group, a cycloalkyl group, an aryl group, or an acyl group.
Each of $R_3$ and $R_4$ independently represents a hydrogen atom, or an organic group having 2 or more carbon atoms. $R_3$ and $R_4$ may be bonded to each other to form a ring.

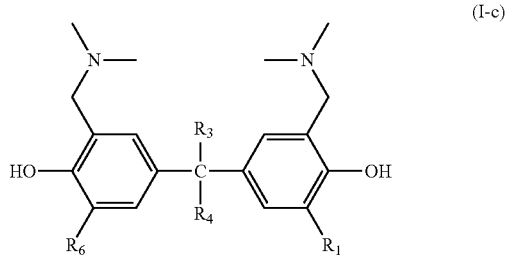

In General Formula (I-c), $R_1$, $R_3$, $R_4$, and $R_6$ have the same definitions as $R_1$, $R_3$, $R_4$, and $R_6$ in General Formula (I), respectively.

According to the present invention, it has become possible to provide an actinic ray-sensitive or radiation-sensitive resin composition which is capable of reducing line width variation in a pattern dependent on the PEB temperature during the formation of an ultrafine pattern (for example, one having a line width of 50 nm or less), and which also has excellent storage stability, as well as an actinic ray-sensitive or radiation-sensitive film, a mask blank provided with the same film, a photomask, a pattern forming method, a method for manufacturing an electronic device, and an electronic device, each using the composition. Further, according to the present invention, it has become possible to provide a novel compound which can be suitably used in the above-mentioned actinic ray-sensitive or radiation-sensitive resin composition, and a method for producing the same compound.

DESCRIPTION OF THE PREFERRED EMBODIMENTS

Figure 1:
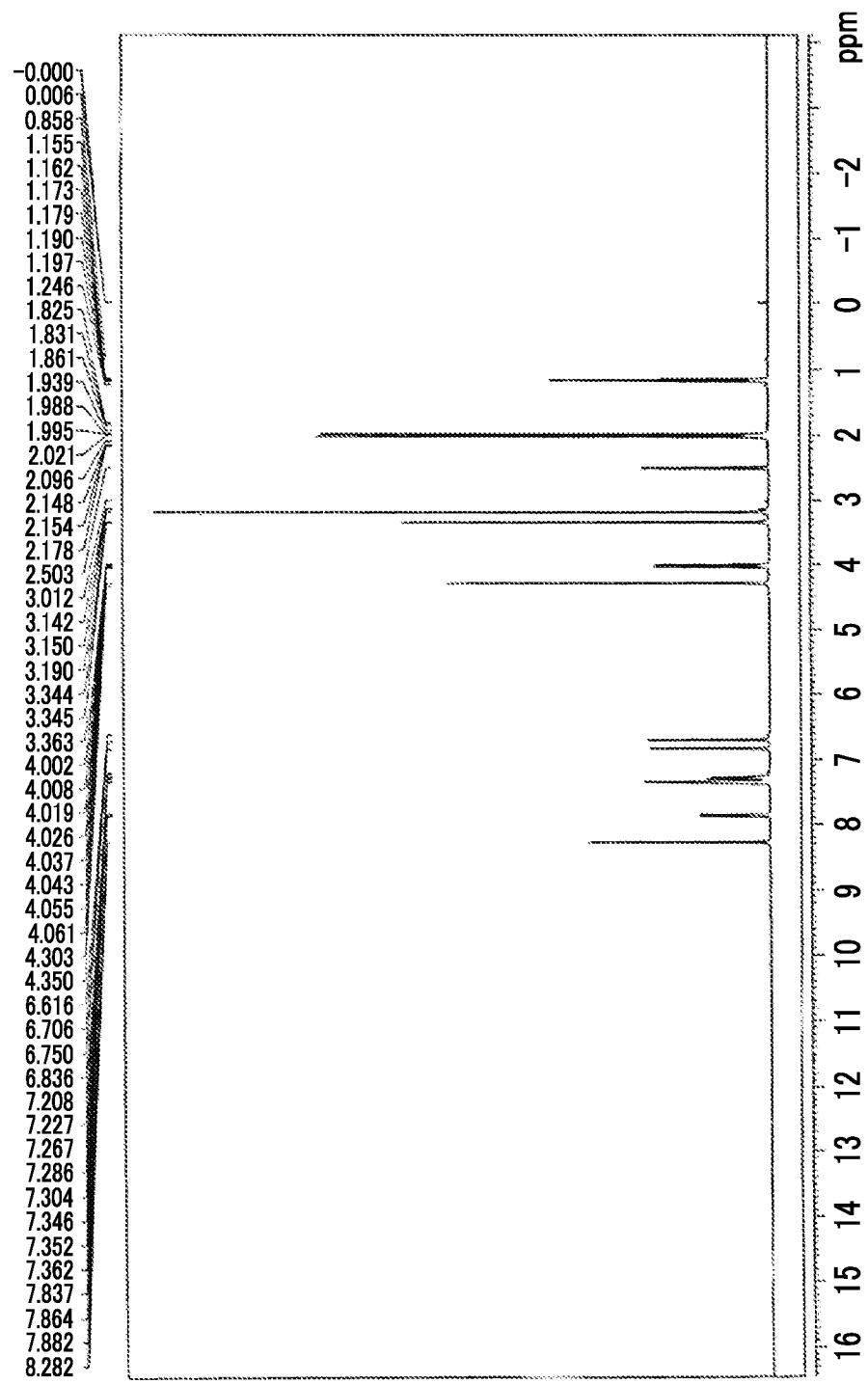
FIG. 1 shows an NMR chart ($^1$HNMR, acetone-d6) of a crosslinking agent (C-1) synthesized in Examples.

In the description of the present invention, when a group (atomic group) is denoted without specifying whether substituted or unsubstituted, the group includes both a group having no substituent and a group having a substituent. For example. "an alkyl group" includes not only an alkyl group having no substituent (unsubstituted alkyl group) but also an alkyl group having a substituent (substituted alkyl group).

Incidentally, the term "actinic rays" or "radiation" as used herein indicates, for example, a bright line spectrum of mercury lamp, a far ultraviolet ray typified by excimer laser, extreme ultraviolet rays (EUV light), X-rays, or an electron beam (EB). Also, in the present invention, the "light" means actinic rays or radiation.

Furthermore, unless otherwise indicated, the term "exposure" as used herein includes not only exposure to a mercury lamp, a far ultraviolet ray represented by excimer laser, extreme ultraviolet rays (EUV light), X-rays, or the like but also lithography with a particle beam such as an electron beam and an ion beam.

Hereinafter, embodiments of the present invention will be described in more detail.

<Crosslinking Agent>

The actinic ray-sensitive or radiation-sensitive resin composition of the present invention contains an alkali-soluble resin as will described hereinafter, and a crosslinking agent represented by General Formula (I) (hereinafter referred to also as a "crosslinking agent of the present invention" or a "crosslinking agent (C)").

The present inventors used a fluorene compound described in JP2008-273844A, which has a phenolic hydroxyl group and a hydroxymethyl group, or a compound described in JP2000-1448A, which has a structure in which two phenolic nuclei having a cyclohexyl group and a hydroxymethyl group or an alkoxymethyl group as substituents are symmetrically bonded via a cyclohexylidene group, as crosslinking agent in a resist composition. However, the present inventors were not able to achieve the storage stability for the resist solution required in the case of forming an ultrafine pattern (for example, in particular, one having a line width of 50 nm or less). In addition, reduction in PEB temperature dependency did not reach a satisfactory level. In contrast, the use of the crosslinking agent (C) has resulted in remarkable improvements in storage stability and PEB temperature dependency of the resist solution.

By having a structure containing a substituent attached to a hydroxymethyl group (that is, —$CH_2$—O—$R_2$ and —$CH_2$—O—$R_5$ in General Formula (I)) in place of a hydroxymethyl group, the crosslinking agent (C) of the present invention can suppress an occurrence of particles during storage of the resist solution over a period of time, resulting in remarkably improved storage stability, compared with a structure, such as a hydroxymethyl group, in which a crosslinking reaction proceeds but a self condensate is easily formed.

In addition, in the crosslinking agent (C) of the present invention, a phenolic nucleus contains no substituent other than —$CH_2$—O—$R_2$ and —$CH_2$—O—$R_5$, or contains only a hydrocarbon group having 5 or less carbon atomes even in the case that the phonolic nucleus contains the other substituent. It is believed that the configuration also greatly contributes to an improvement in storage stability. That is, this is because, in the case where a substituent having 6 or more carbon atoms is substituted on the phenolic nucleus, phenol is shielded to result in poor compatibility with an alkali-soluble resin and therefore an amount of particles is increased.

In addition, in the crosslinking agent (C) of the present invention, it is presumed that both of $R_3$ and $R_4$ being an organic group having 2 or more carbon atoms contributes to particularly an improvement of PEB temperature dependency. That is, this is due to that the distortion of the quaternary sp3 regular tetrahedral structure of the carbon atom in the connecting part of two phenolic nuclei results in an improvement of the crosslinkability and therefore lowering of activation energy of the reaction.

Hereinafter, General Formula (I) will be described in more detail.

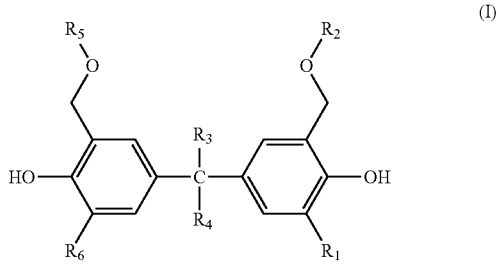

(I)

In General Formula (I),
each of $R_1$ and $R_6$ independently represents a hydrogen atom, or a hydrocarbon group having 5 or less carbon atoms.
Each of $R_2$ and $R_5$ independently represents an alkyl group, a cycloalkyl group, an aryl group, or an acyl group.
Each of $R_3$ and $R_4$ independently represents a hydrogen atom, or an organic group having 2 or more carbon atoms. $R_3$ and $R_4$ may be bonded to each other to form a ring.

In one embodiment of the present invention, $R_1$ and $R_6$ are preferably a hydrocarbon group having 5 or less carbon atoms, more preferably a hydrocarbon group having 4 or less carbon atoms, and particularly preferably a methyl group, an ethyl group, a propyl group, or an isopropyl group.

The alkyl group represented by $R_2$ and $R_5$ is preferably, for example, an alkyl group having 1 to 6 carbon atoms, the cycloalkyl group is preferably, for example, a cycloalkyl group having 3 to 12 carbon atoms, the aryl group is preferably, for example, an aryl group having 6 to 12 carbon atoms, and the acyl group is preferably, for example, an acyl group in which the alkyl portion has 1 to 6 carbon atoms.

In one embodiment of the present invention, $R_2$ and $R_5$ are preferably an alkyl group, more preferably an alkyl group having 1 to 6 carbon atoms, and particularly preferably a methyl group.

Examples of the organic group having 2 or more carbon atoms represented by $R_3$ and $R_4$ may include an alkyl group, a cycloalkyl group, and an aryl group each having 2 or more carbon atoms. Further, $R_3$ and $R_4$ are preferably bonded to each other to form a ring which will be described hereinafter in more detail.

Examples of the ring which is formed by bonding of $R_3$ and $R_4$ to each other may include an aromatic or non-aromatic hydrocarbon ring, an aromatic or non-aromatic heterocyclic ring, and a polycyclic fused ring formed by a combination of two or more rings thereof.

These rings may have a substituent, and examples of the substituent may include an alkyl group, a cycloalkyl group, an alkoxy group, a carboxyl group, an aryl group, alkoxymethyl group, an acyl group, an alkoxycarbonyl group, a nitro group, halogen, and a hydroxy group.

Hereinafter, specific examples of the ring formed by bonding of $R_3$ and $R_4$ to each other are shown. * in the formula indicates a connecting site to the phenolic nucleus.

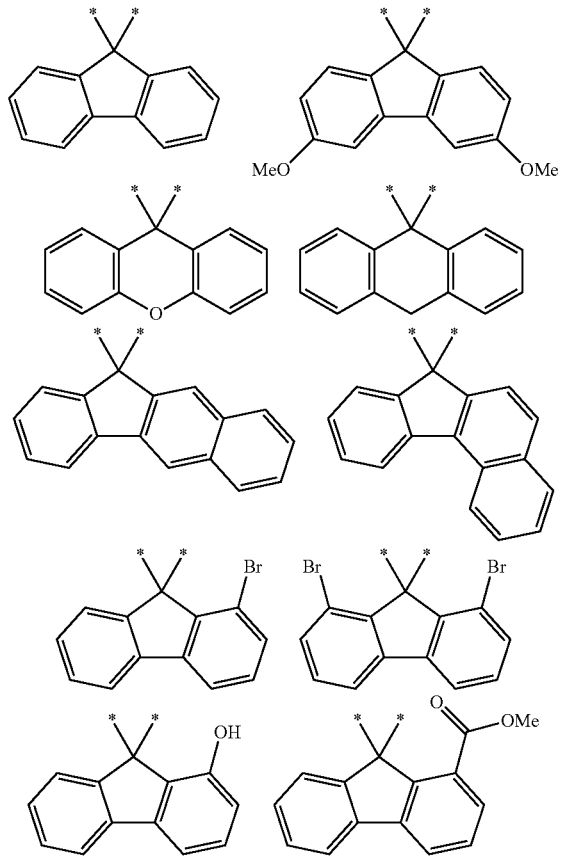

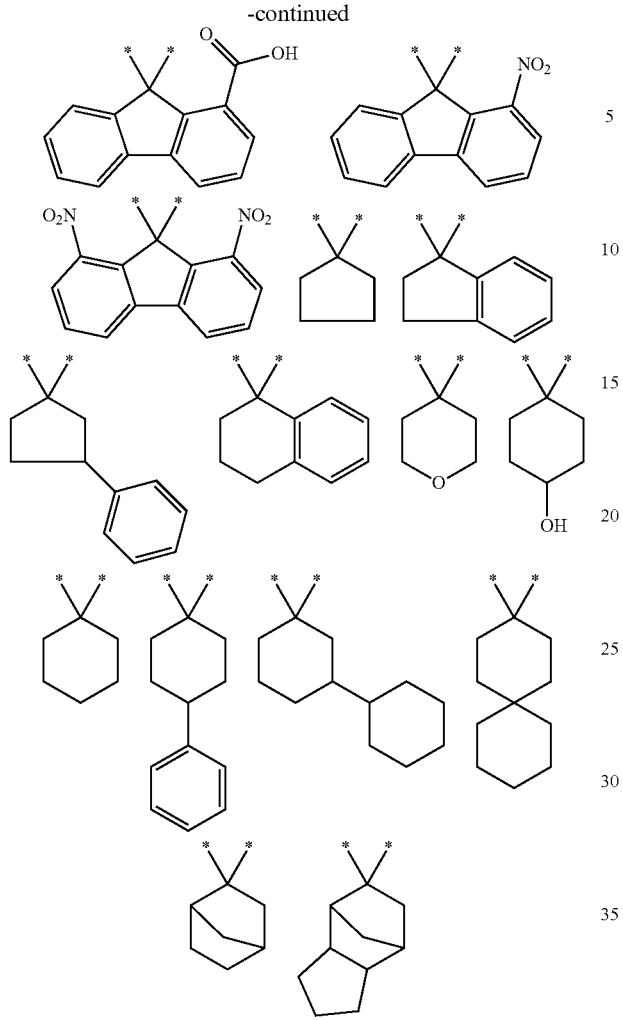

In one embodiment of the present invention, $R_3$ and $R_4$ in General Formula (I) are preferably bonded to form a polycyclic fused ring containing a benzene ring, and more preferably a fluorene structure.

As for the crosslinking agent (C), for example. $R_3$ and $R_4$ in General Formula (I) are preferably bonded to form a fluorene structure represented by the following General Formula (I-a).

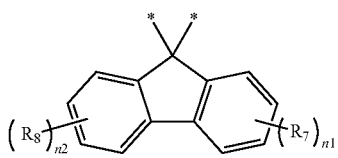

(I-a)

In the formula,
each of $R_7$ and $R_8$ independently represents a substituent. Examples of the substituent may include an alkyl group, a cycloalkyl group, an alkoxy group, an aryl group, alkoxymethyl group, an acyl group, an alkoxycarbonyl group, a nitro group, halogen, and a hydroxy group.

Each of n1 and n2 independently represents an integer of 0 to 4, and preferably 0 or 1.
* indicates a connecting site to the phenolic nucleus.

Further, in one embodiment of the present invention, the crosslinking agent (C) is preferably represented by the following General Formula (I-b).

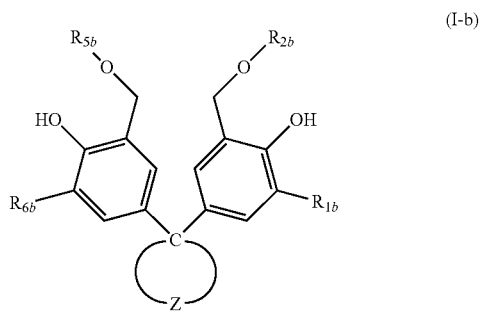

(I-b)

In the formula,
each of $R_{1b}$ and $R_{6b}$ independently represents an alkyl group 5 or less carbon atoms.
Each of $R_{2b}$ and $R_{5b}$ independently represents an alkyl group having 6 or less carbon atoms or a cycloalkyl group having 3 to 12 carbon atoms.
Z represents an atomic group necessary for forming a ring together with the carbon atom in the formula.
Details of the ring which Z forms together with the carbon atom in the formula are the same as those described for the ring formed by bonding of $R_3$ and $R_4$ to each other in the description of General Formula (I).

Next, a method of preparing the crosslinking agent (C) will be described.

The bisphenol compound serving as a mother nucleus of the crosslinking agent (C) is generally synthesized by a dehydration condensation reaction between corresponding two phenol compound molecules and corresponding one ketone molecule in the presence of an acid catalyst.

The resulting bisphenol entity is subjected to amionmethylation by treatment with paraformaldehyde and dimethylamine to obtain an intermediate represented by the following General Formula (I-c). This is followed by acetylation, deacetylation, and alkylation to give a desired crosslinking agent (C).

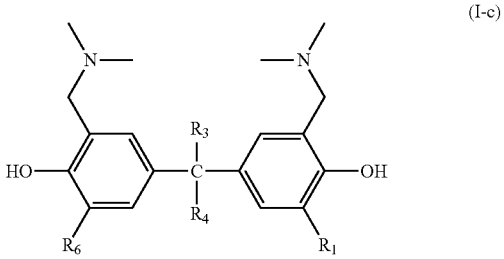

(I-c)

In the formula. $R_1$, $R_3$, $R_4$, and R have the same definitions as those in General Formula (I), respectively.

The present synthesis method is not liable to produce an oligomer as compared to a conventional synthesis method via the hydroxymethyl entity under basic conditions (for example, JP2008-273844A), and therefore exhibits an effect of suppressing the formation of particles.

Hereinafter, specific examples of the crosslinking agent (C) are shown.

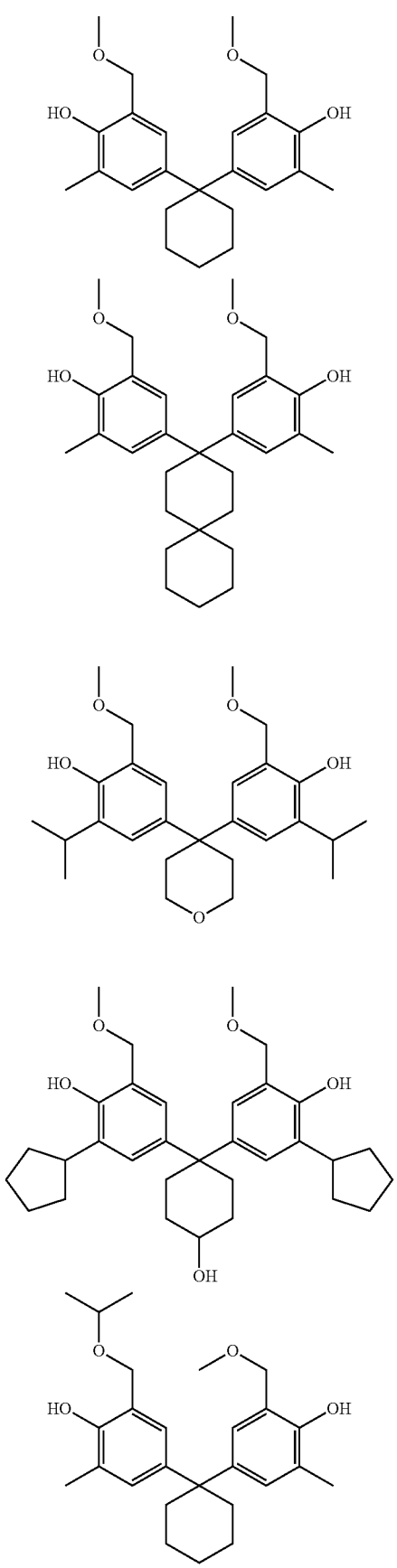
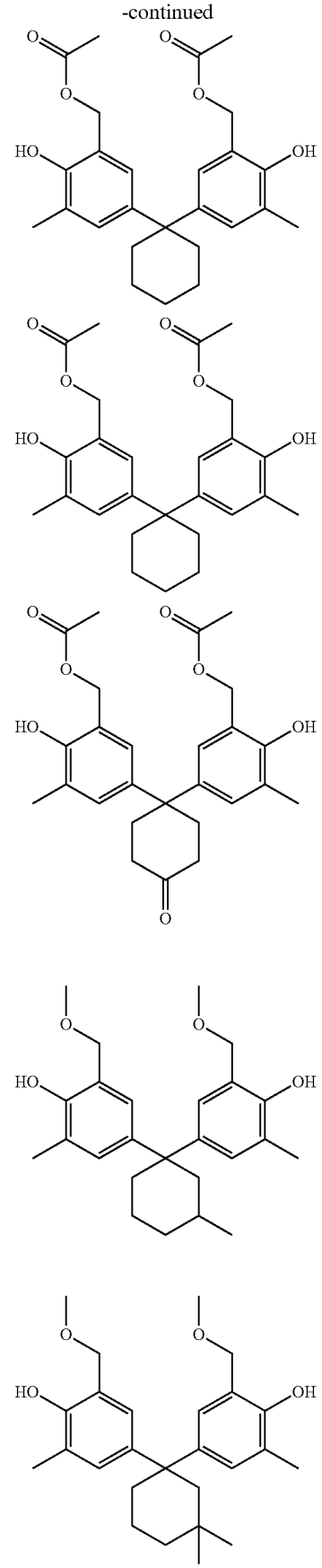

-continued
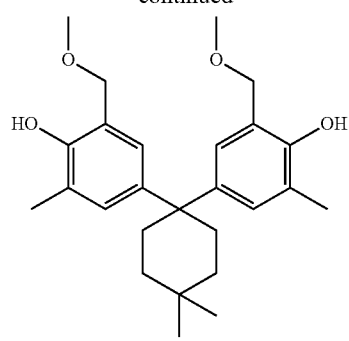
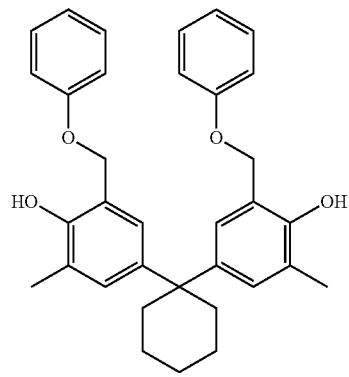
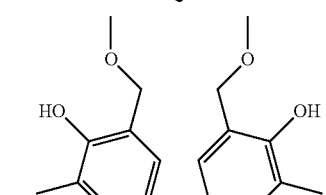
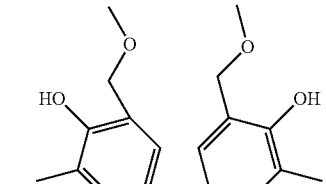
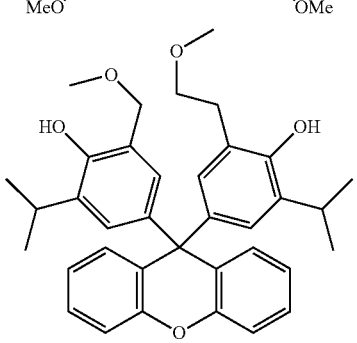
-continued
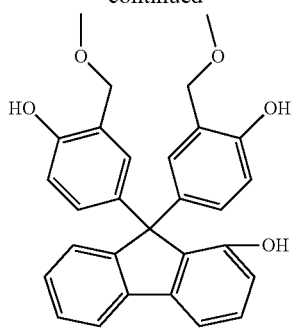
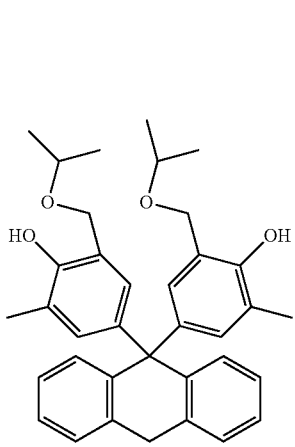
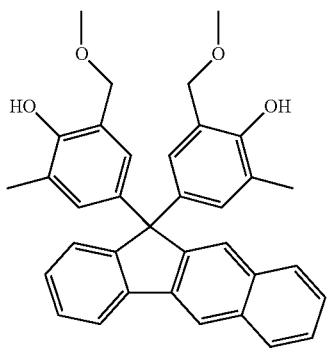
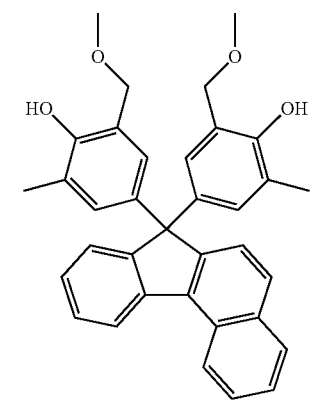

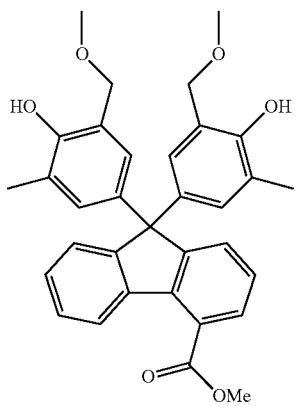
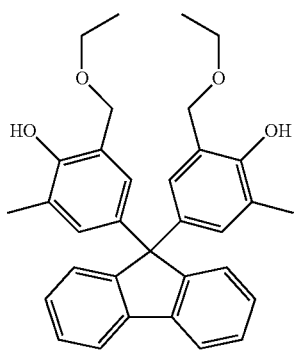
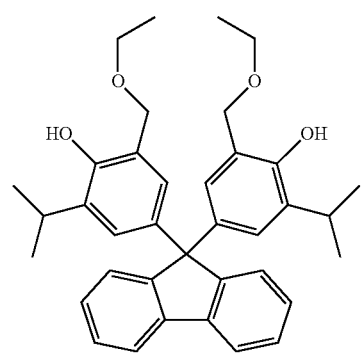
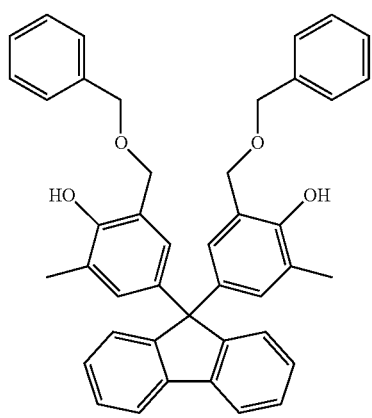
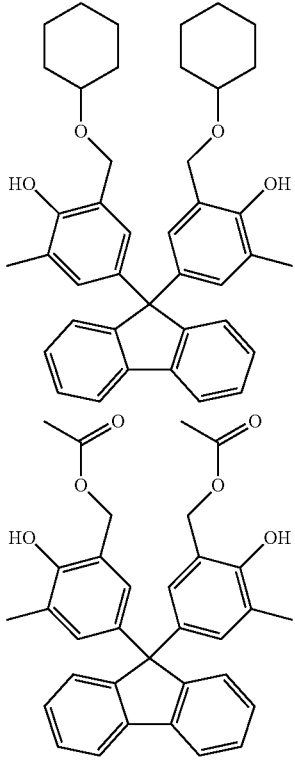
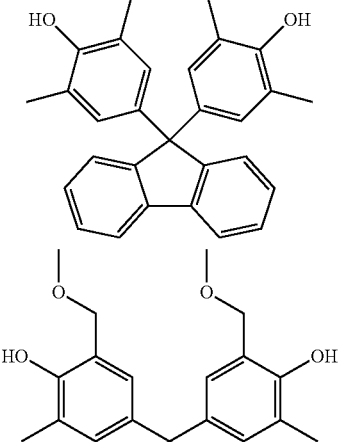
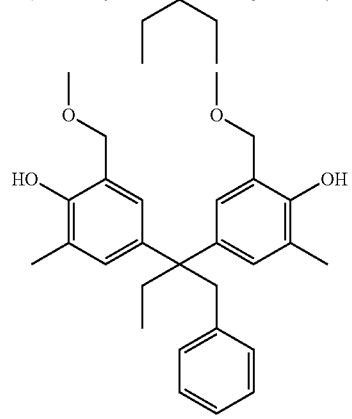

In the present invention, the content of the crosslinking agent (C) is preferably 5 mass % to 80 mass %, and more preferably 10 mass % to 50 mass %, based on the solid content of the actinic ray-sensitive or radiation-sensitive resin composition of the present invention.

The crosslinking agent (C) may be used alone or in combination of two or more thereof. Moreover, the crosslinking agent (C) may be used in combination with another crosslinking agent different from the later-described crosslinking agent (C) in an amount not impairing the effect of the present invention.

<Alkali-Soluble Resin>

The actinic ray-sensitive or radiation-sensitive resin composition of the present invention contains an alkali-soluble resin (hereinafter referred to also as "resin (A)").

The resin (A) is not particularly limited as long as it is alkali-soluble, but the resin (A) is preferably a resin containing a phenolic hydroxyl group.

The phenolic hydroxyl group as used in the present invention is a group formed by substituting for a hydrogen atom of an aromatic ring group by a hydroxyl group. The aromatic ring of this aromatic ring group is a monocyclic or polycyclic aromatic ring and includes, for example, a benzene ring and a naphthalene ring.

According to the composition of the present invention comprised of the resin (A), in the exposed area, in the case where the resin (A) has a later-described "structural moiety capable of decomposing upon irradiation with actinic rays or radiation to generate an acid on the side chain", a crosslinking reaction takes place, from the structural moiety, between the resin (A) containing a phenolic hydroxyl group and the crosslinking agent (C), whereby a negative pattern is formed. Alternatively, in the case where the composition of the present invention contains a later-described "acid generator (B)", a crosslinking reaction takes place by the action of an acid generated from the compound, between the resin (A) containing a phenolic hydroxyl group and the crosslinking agent (C), whereby a negative pattern is formed.

The resin (A) preferably contains a repeating unit having at least one phenolic hydroxyl group. The repeating unit having a phenolic hydroxyl group is not particularly limited, but is preferably a repeating unit represented by the following General Formula (II).

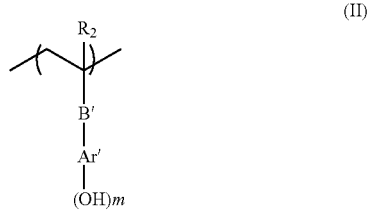

(II)

In the formula,

R$_2$ represents a hydrogen atom, a methyl group which may have a substituent, or a halogen atom (preferably a fluorine atom);

B' represents a single bond or a divalent linking group;

Ar' represents an aromatic ring; and m represents an integer of 1 or greater.

Examples of the methyl group which may have a substituent for R$_2$ include a trifluoromethyl group and a hydroxymethyl group.

R$_2$ is preferably a hydrogen atom or a methyl group, and a hydrogen atom is preferred from the viewpoint of developability.

The divalent linking group of B' is preferably a carbonyl group, an alkylene group (preferably having 1 to 10 carbon atoms, and more preferably 1 to 5 carbon atoms), a sulfonyl group (—S(=O)$_2$—), —O—, —NH—, or a divalent linking group formed by combining these groups.

B' preferably represents a single bond, a carbonyloxy group (—C(=O)—O—), or —C(=O)—NH—; and more preferably represents a single bond or a carbonyloxy group (—C(=O)—O—), and it is particularly preferable for B' to represent a single bond, from the viewpoint of enhancing dry etching resistance.

The aromatic ring of Ar' is a monocyclic or polycyclic aromatic ring, and examples thereof include aromatic hydrocarbon rings having 6 to 18 carbon atoms which may have a substituent, such as a benzene ring, a naphthalene ring, an anthracene ring, a fluorene ring, and a phenanthrene ring; and aromatic heterocyclic rings containing heterocyclic rings such as, for example, a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, and a thiazole ring. Among them, a benzene ring and a naphthalene ring are preferred from the viewpoint of resolution, and a benzene ring is most preferred from the viewpoint of sensitivity.

m is preferably an integer of 1 to 5, and most preferably 1. When m is 1 and Ar' is a benzene ring, the position of substitution of —OH may be a para-position, a meta-position, or an ortho-position with respect to the bonding position of the benzene ring to B' (when B' is a single bond, the polymer main chain). However, from the viewpoint of crosslinking reactivity, a para-position and a meta-position are preferred, and a para-position is more preferred.

The aromatic ring of Ar' may have a substituent other than the group represented by —OH, and examples of the substituent may include an alkyl group, a cycloalkyl group, a halogen atom, a hydroxyl group, an alkoxy group, a carboxyl group, an alkoxycarbonyl group, an alkylcarbonyl group, an alkylcarbonyloxy group, an alkylsulfonyloxy group, and an arylcarbonyl group.

The repeating unit having a phenolic hydroxyl group is more preferably a repeating unit represented by the following General Formula (II'), from the viewpoints of crosslinking reactivity, developability, and dry etching resistance.

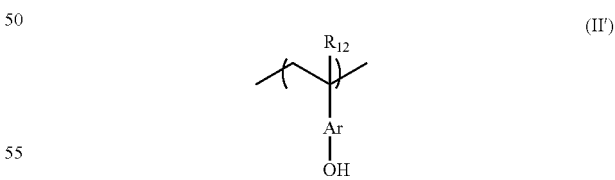

(II')

In General Formula (II'),

R$_{12}$ represents a hydrogen atom or a methyl group.

Ar represents an aromatic ring.

R$_{12}$ represents a hydrogen atom or a methyl group, and is preferably a hydrogen atom in view of the developability.

Ar in General Formula (II') is the same as Ar' in General Formula (II), and the preferred range thereof is also the same as that in General Formula (II). As for the repeating unit represented by General Formula (II'), a repeating unit derived from hydroxystyrene (that is, a repeating unit of General Formula (II') in which $R_{12}$ is a hydrogen atom and Ar is a benzene ring) is preferred from the viewpoint of the sensitivity.

The resin (A) may be constituted by only the above described repeating unit having a phenolic hydroxyl group. The resin (A) may have a repeating unit as described below, in addition to the above described repeating unit having a phenolic hydroxyl group. In this case, the content of the repeating unit having a phenolic hydroxyl group is preferably 10 mol % to 98 mol %, more preferably 30 mol % to 97 mol %, and still more preferably 40 mol % to 95 mol %, based on the total content of the repeating units of the resin (A). Accordingly, particularly, in the case where the resist film is a thin film (for example, in the case where the thickness of the resist film is from 10 nm to 150 nm), it is possible to more reliably reduce the dissolution rate of an exposed area of the resist film of the present invention, which is formed using the resin (A), in an alkali developer (that is, it is possible to more reliably control the dissolution rate of the resist film employing the resin (A) to an optimum level). As a result, the sensitivity may be more reliably improved.

Examples of the repeating unit having a phenolic hydroxyl group will be described below, but are not limited thereto.

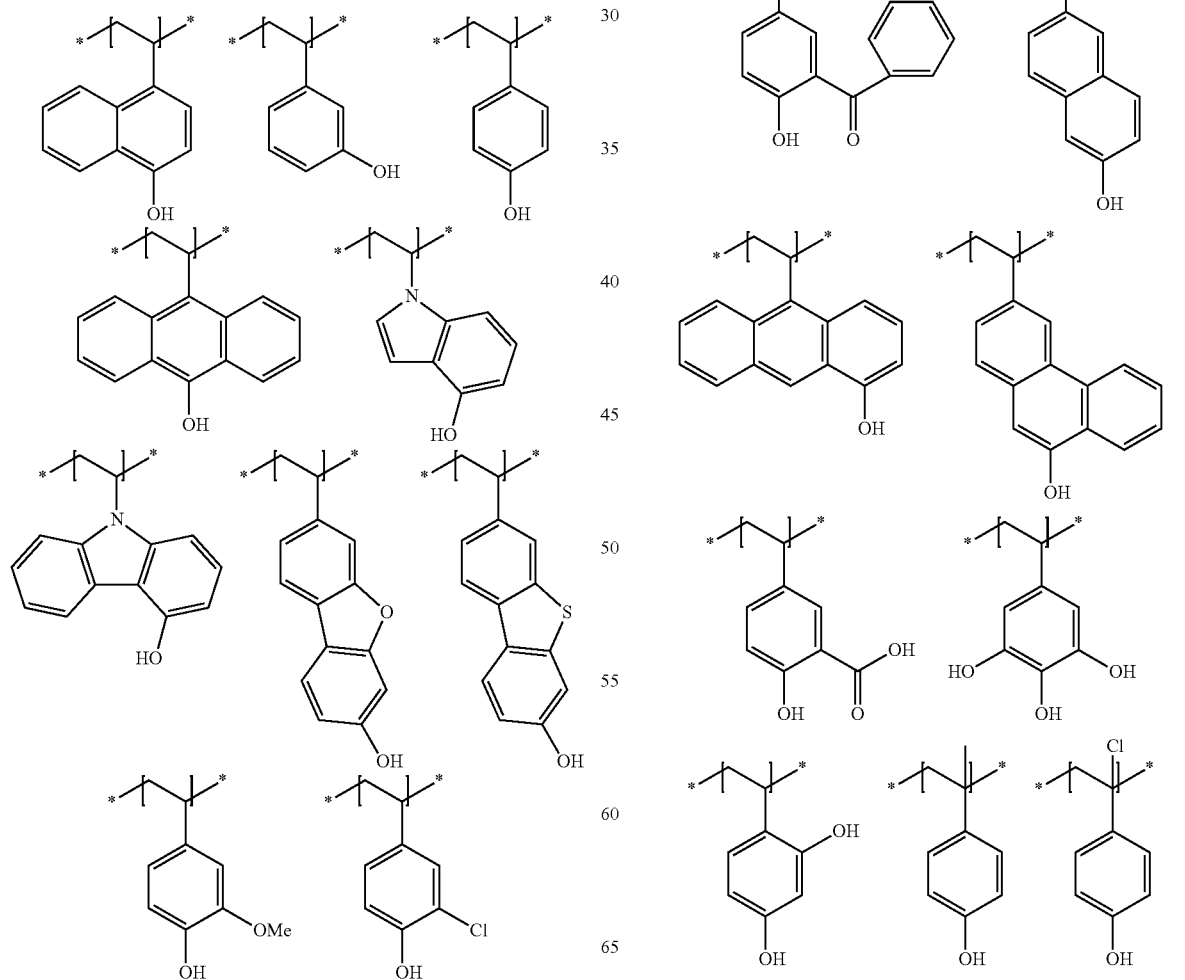

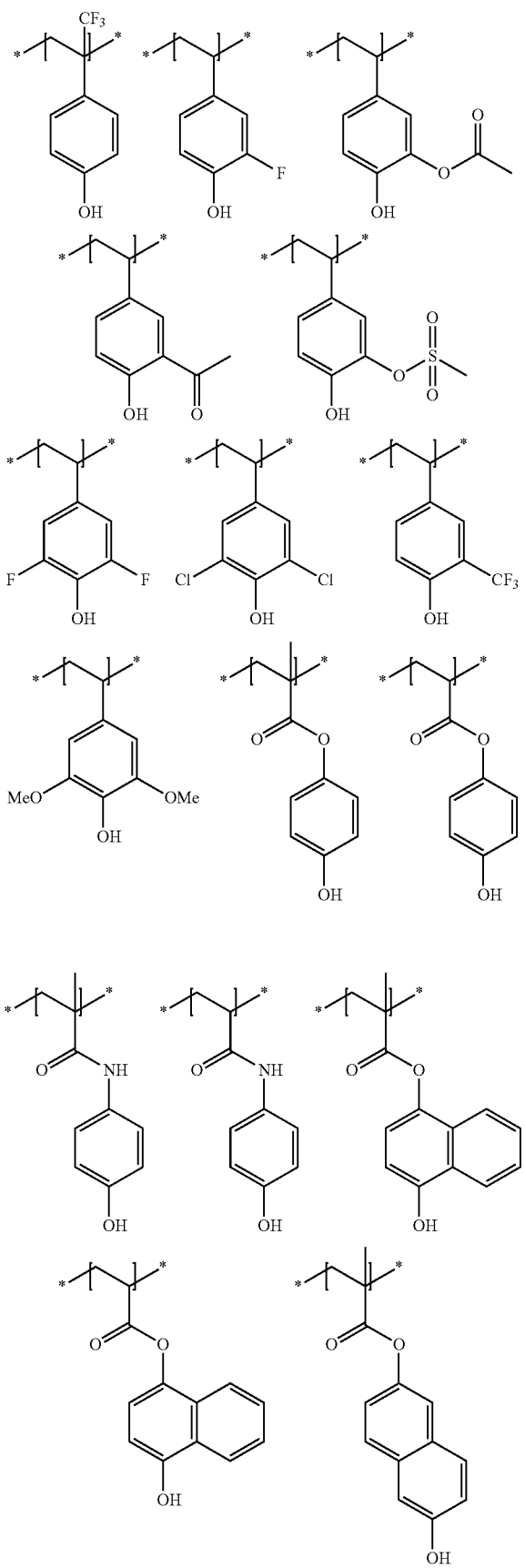

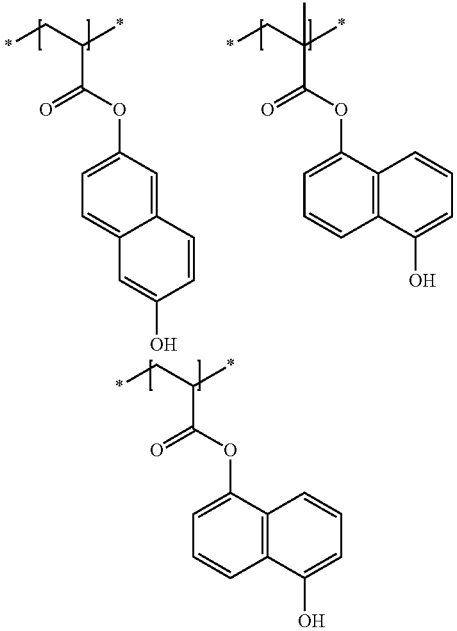

The resin (A) preferably has "a structure in which a hydrogen atom of the phenolic hydroxyl group is substituted with a group having a non-acid-decomposable hydrocarbon structure" from the viewpoints of achieving a high glass transition temperature (Tg) and favorable dry etching resistance. In addition, improving effects of the PEB temperature dependency can be further enhanced by the synergistic effect with the crosslinking agent (C).

Due to the fact that the resin (A) has a specific structure as described above, the glass transition temperature (Tg) of the resin (A) becomes high, so that a very hard resist film can be formed and the acid diffusion or dry etching resistance can be controlled. Accordingly, an acid is highly constrained from diffusion in the area exposed to actinic rays or radiation such as an electron beam and extreme ultraviolet rays, and this produces an excellent effect in terms of resolution, pattern profile, and LER in a fine pattern. Also, the point that the resin (A) has a non-acid-decomposable hydrocarbon structure further contributes to an improvement in dry etching resistance. Furthermore, although details are unknown, it is presumed that the hydrocarbon structure has a high hydrogen radical-donating property and become to serve as a hydrogen source when decomposing a photoacid generator, as a result, the decomposition efficiency of the photoacid generator and in turn, the acid generation efficiency are further enhanced. This is considered to contribute to excellent sensitivity.

In the aforementioned specific structure which may be taken by the resin (A) according to the present invention, an aromatic ring such as a benzene ring and a group having a non-acid-decomposable hydrocarbon structure are connected through an oxygen atom derived from a phenolic hydroxyl group. As described above, that structure not only contributes to high dry etching resistance but also enables raising the glass transition temperature (Tg) of the resin (A). As a consequence, combinatorial effects thereof are believed to provide high resolution.

In the present invention, the term "non-acid-decomposable" means a property of not causing a decomposition reaction by an acid generated from a photoacid generator and an acid generated from the later-described structure (a) capable of generating an acid.

More specifically, the group having a non-acid-decomposable hydrocarbon structure is preferably a group stable to an acid and an alkali. The term "group stable to an acid and an alkali" means a group not exhibiting acid decomposability and alkali decomposability. The term "acid decomposability" as used herein means a property of causing a decomposition reaction by the action of an acid generated from a photoacid generator and an acid generated from the later-described structure (a) capable of generating an acid.

Also, the term "alkali decomposability" means a property of causing a decomposition reaction by the action of an alkali developer, and the group exhibiting alkali decomposability includes the conventionally known group capable of decomposing by the action of an alkali developer to increase the dissolution rate in an alkali developer (for example, a group having a lactone structure), which is contained in the resin suitably used for the positive actinic ray-sensitive or radiation-sensitive resin composition.

The group having a hydrocarbon structure is not particularly limited as long as it is a monovalent group having a hydrocarbon structure, but the total number of carbon atoms thereof is preferably 5 to 40, and more preferably 7 to 30. The hydrocarbon structure may have an unsaturated bond in the ring.

The hydrocarbon structure in the group having a hydrocarbon structure means a structure having a chain-like or branched hydrocarbon group or a monocyclic alicyclic hydrocarbon group, or a polycyclic alicyclic hydrocarbon structure, and may be a crosslinked structure. The monocyclic alicyclic hydrocarbon group is preferably a cycloalkyl group having 3 to 8 carbon atoms, and examples thereof may include a cyclopropyl group, a cyclopentyl group, a cyclohexyl group, a cyclobutyl group, and a cyclooctyl group. The structure having a monocyclic alicyclic hydrocarbon group may have plural such groups. The structure having plural monocyclic alicyclic hydrocarbon groups preferably has two to four monocyclic alicyclic hydrocarbon groups, and particularly preferably two monocyclic alicyclic hydrocarbon groups.

The chain-like or branched hydrocarbon group may be a hydrocarbon group having 1 to 20 carbon atoms (more preferably having 1 to 10 carbon atoms, and still more preferably 1 to 7 carbon atoms), and examples thereof may include a propyl group, an isopropyl group, an n-butyl group, an s-butyl group, an isobutyl group, a pentyl group, an isopentyl group, a neopentyl group, a hexyl group, a 2-ethylhexyl group, and an octyl group.

The polycyclic alicyclic hydrocarbon structure may be a bicyclo-, tricyclo-, or tetracyclo-structure having 5 or more carbon atoms and is preferably a polycyclic cyclo-structure having 6 to 30 carbon atoms, and examples thereof may include an adamantane structure, a decalin structure, a norbornane structure, a norbornene structure, a cedrol structure, an isobornane structure, a bornane structure, a dicyclopentane structure, an α-pinene structure, a tricyclodecane structure, a tetracyclododecane structure, and an androstane structure. Incidentally, a part of carbon atoms in the monocyclic or polycyclic cycloalkyl group may be substituted by a heteroatom such as oxygen atom.

The hydrocarbon structure is preferably an adamantane structure, a decalin structure, a norbornane structure, a norbornene structure, a cedrol structure, a structure having a plurality of cyclohexyl groups, a structure having a plurality of cycloheptyl groups, a structure having a plurality of cyclooctyl groups, a structure having a plurality of cyclodecanyl groups, a structure having a plurality of cyclododecanyl groups, or a tricyclodecane structure, and most preferably an adamantane structure in view of dry etching resistance (that is, it is most preferred that the group having a non-acid-decomposable hydrocarbon structure is a group having a non-acid-decomposable adamantane structure).

Chemical formulae of these hydrocarbon structures are illustrated below.

(1)

(2)

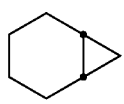

(3)

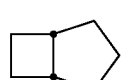

(4)

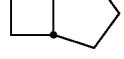

(5)

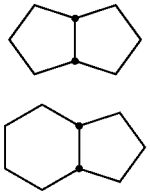

(6)

(7)

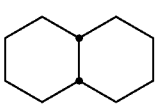

(8)

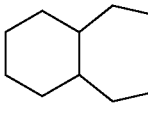

(9)

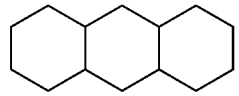

(10)

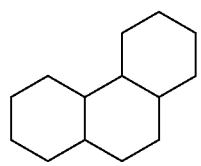

(11)

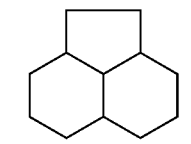

(12)

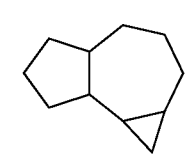

(13)
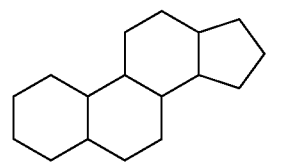
(14)
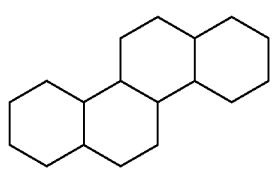
(15)
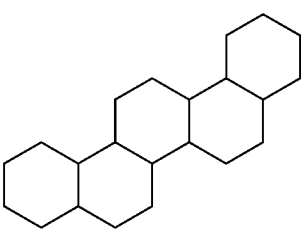
(16)
(17)
(18)
(19)
(20)
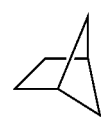
(21)
(22)
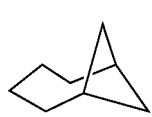
(23)
(24)
(25)
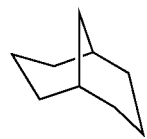
(26)
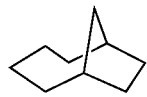
(27)
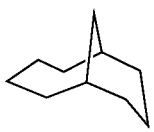
(28)
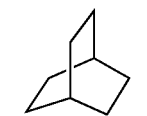
(29)
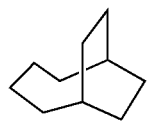
(30)
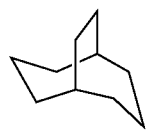
(31)
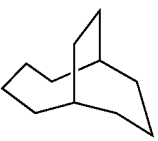
(32)
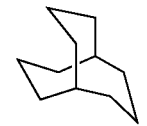
(33)
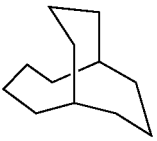
(34)
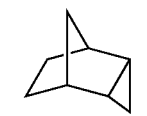
(35)
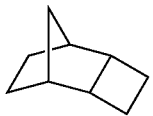

(36) 

(37) 

(38) 

(39) 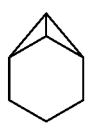

(40) 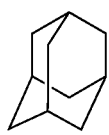

(41) 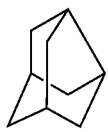

(42) 

(43) 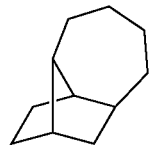

(44) 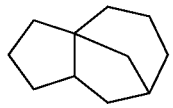

(45) 

(46) 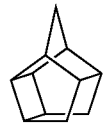

(47) 

(48) 

(49) 

(50) 

(51) 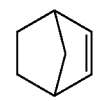

The hydrocarbon structure may further have a substituent, and examples of the substituent may include an alkyl group (preferably having 1 to 6 carbon atoms), a cycloalkyl group (preferably having 3 to 10 carbon atoms), an aryl group (preferably having 6 to 15 carbon atoms), a halogen atom, a hydroxyl group, an alkoxy group (preferably having 1 to 6 carbon atoms), a carboxyl group, a carbonyl group, a thiocarbonyl group, an alkoxycarbonyl group (preferably having 2 to 7 carbon atoms), and a group formed by combining these groups (preferably having a total number of 1 to 30 carbon atoms, more preferably a total number of 1 to 15 carbon atoms).

The hydrocarbon structure is preferably a structure represented by any one of Formulae (7), (23), (40), (41), and (51), or a structure having two monovalent groups each formed by substituting a bond for one arbitrary hydrogen atom in the structure of Formula (48), more preferably a structure represented by any one of Formulae (23), (40), and (51), or a structure having two monovalent groups each formed by substituting a bond for one arbitrary hydrogen atom in the structure of Formula (48), and most preferably a structure represented by Formula (40).

The group having a hydrocarbon structure is preferably a monovalent group formed by substituting a bond for one arbitrary hydrogen atom in the above-described hydrocarbon structure.

In the resin (A), "the structure where a hydrogen atom of a phenolic hydroxyl group is substituted by the above-described group having a non-acid-decomposable hydrocarbon structure" is preferably contained as a repeating unit having such a structure. Such a structure leads to a reduction in the number of crosslinking points in the resin (A), such as a phenolic hydroxyl group or the ortho-position carbon atom of phenol and consequently suppresses an excessive progress of the reaction in the film by an acid generated upon exposure to light. From the viewpoint of further improving PEB stability, the above-mentioned structure is preferably contained in resin (A) as a repeating unit represented by the following General Formula (1). According to this structure, an excessive reaction of the acid generated upon exposure to light is suppressed, for example even in the case where the resist film is allowed to stand after the exposure to light.

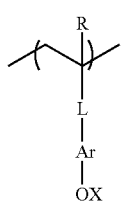

(1)

In General Formula (1), R represents a hydrogen atom or a methyl group, X represents a group having a non-acid-decomposable hydrocarbon group, Ar represents an aromatic ring, and L represents a divalent linking group.

In General Formula (1), R represents a hydrogen atom or a methyl group and is particularly preferably a hydrogen atom.

Examples of the aromatic ring represented by Ar in General Formula (1) may include an aromatic hydrocarbon ring having 6 to 18 carbon atoms which may have a substituent, such as benzene ring, naphthalene ring, anthracene ring, fluorene ring, and phenanthrene ring, and an aromatic heterocyclic ring containing a heterocyclic ring such as thiophene ring, furan ring, pyrrole ring, benzothiophene ring, benzofuran ring, benzopyrrole ring, triazine ring, imidazole ring, benzimidazole ring, triazole ring, thiadiazole ring, and thiazole ring. Among these, a benzene ring and a naphthalene ring are preferred in view of resolution, and a benzene ring is most preferred.

The aromatic ring of Ar may have a substituent other than the group represented by —OX, and examples of the substituent may include an alkyl group (preferably having 1 to 6 carbon atoms), a cycloalkyl group (preferably having 3 to 10 carbon atoms), an aryl group (preferably having 6 to 15 carbon atoms), a halogen atom, a hydroxyl group, an alkoxy group (preferably having 1 to 6 carbon atoms), a carboxyl group, and an alkoxycarbonyl group (preferably having 2 to 7 carbon atoms). Among these, an alkyl group, an alkoxy group, and an alkoxycarbonyl group are preferred, and an alkoxy group is more preferred.

X represents a group having a non-acid-decomposable hydrocarbon group, and preferably represents a group having a non-acid-decomposable hydrocarbon structure. Specific examples and preferred ranges of the group having a non-acid-decomposable hydrocarbon structure represented by X are the same as those described above. X is more preferably a group represented by —Y—$X_2$ in later-described General Formula (4).

The divalent linking group of L is preferably a carbonyl group, an alkylene group (preferably having 1 to 10 carbon atoms, more preferably 1 to 5 carbon atoms), a sulfonyl group (—S(=O)$_2$—), —O—, —NH—, or a divalent linking group formed by combining these groups.

L preferably represents a single bond, a carbonyloxy group (—C(=O)—O—), or —C(=O)—NH—, more preferably a single bond or a carbonyloxy group (—C(=O)—O—), and from the viewpoint of improving dry etching resistance, particularly preferably a single bond.

In the present invention, the repeating unit represented by General Formula (1) is preferably a repeating unit represented by the following General Formula (4).

When the resin (A) having a repeating unit represented by General Formula (4) is used, Tg of the resin (A) becomes high and a very hard resist film is formed, so that the acid diffusion and dry etching resistance can be more reliably controlled.

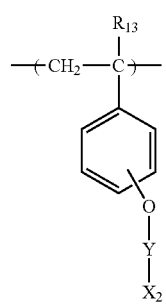

(4)

In General Formula (4), $R_{13}$ represents a hydrogen atom or a methyl group.

Y represents a single bond or a divalent linking group.

$X_2$ represents a non-acid-decomposable hydrocarbon group.

Preferred embodiments of the repeating unit represented by General Formula (4) for use in the present invention are described below.

In General Formula (4), $R_{13}$ represents a hydrogen atom or a methyl group and is preferably a hydrogen atom.

In General Formula (4), Y is preferably a divalent linking group. The divalent linking group of Y is preferably a carbonyl group, a thiocarbonyl group, an alkylene group (preferably having 1 to 10 carbon atoms, more preferably 1 to 5 carbon atoms), a sulfonyl group, —COCH$_2$—, —NH—, or a divalent linking group formed by combining these groups (preferably having a total number of 1 to 20 carbon atoms, more preferably a total number of 1 to 10 carbon atoms), more preferably a carbonyl group, —COCH$_2$—, a sulfonyl group, —CONH—, or —CSNH—, still more preferably a carbonyl group or —COCH$_2$—, and particularly preferably a carbonyl group.

$X_2$ represents a hydrocarbon group and is non-acid-decomposable. The total number of carbon atoms in the hydrocarbon group is preferably 5 to 40, and more preferably 7 to 30. The hydrocarbon group may have an unsaturated bond in the ring thereof.

This hydrocarbon group is a chain-like or branched hydrocarbon group, a group having a monocyclic alicyclic hydrocarbon group, or a polycyclic alicyclic hydrocarbon group, and may be a crosslinked group. The monocyclic alicyclic hydrocarbon group is preferably a cycloalkyl group having 3 to 8 carbon atoms, and examples thereof may include a cyclopropyl group, a cyclopentyl group, a cyclohexyl group, a cyclobutyl group, and a cyclooctyl group. The group having a monocyclic alicyclic hydrocarbon group may have plural such groups. The group having plural monocyclic alicyclic hydrocarbon groups preferably has two to four monocyclic alicyclic hydrocarbon groups, and particularly preferably two monocyclic alicyclic hydrocarbon groups.

The chain-like or branched hydrocarbon group is preferably a group having 1 to 20 carbon atoms, more preferably a group having 1 to 10 carbon atoms, and still more preferably a group having 1 to 7 carbon atoms. Specific examples of the chain-like or branched hydrocarbon group may include a propyl group, an isopropyl group, an n-butyl group, an s-butyl group, an isobutyl group, a pentyl group, an isopentyl group, a neopentyl group, a hexyl group, a 2-ethylhexyl group, and an octyl group.

The polycyclic alicyclic hydrocarbon group may include a group containing, for example, a bicyclo-, tricyclo-, or tetracyclo-structure having 5 or more carbon atoms and is preferably a group containing a polycyclic cyclo-structure having 6 to 30 carbon atoms, and examples thereof include an adamantyl group, a norbornyl group, a norbornenyl group, an isobornyl group, a camphanyl group, a dicyclopentyl group, an α-pinel group, a tricyclodecanyl group, a tetracyclododecyl group, and an androstanyl group. Incidentally, a part of carbon atoms in the monocyclic or polycyclic cycloalkyl group may be substituted by a heteroatom such as oxygen atom.

The polycyclic alicyclic hydrocarbon group of $X_2$ is preferably an adamantyl group, a decalin group, a norbornyl group, a norbornenyl group, a cedrol group, a group having a plurality of cyclohexyl groups, a group having a plurality of cycloheptyl groups, a group having a plurality of cyclooctyl groups, a group having a plurality of cyclodecanyl groups, a group having a plurality of cyclododecanyl groups, or a tricyclodecanyl group, and most preferably an adamantyl group in view of dry etching resistance. Examples of the chemical formula of the hydrocarbon structure in the hydrocarbon group of $X_2$ are the same as those of the chemical formula of the hydrocarbon structure in the above-described group having a hydrocarbon structure, and the preferred range thereof is also the same. The hydrocarbon group of $X_2$ includes a monovalent group formed by substituting a bond for one arbitrary hydrogen atom in the above-described hydrocarbon structure.

The alicyclic hydrocarbon group may further have a substituent, and examples of the substituent are the same as those described above as the substituent which may be substituted on the hydrocarbon structure.

In General Formula (4), the substitution position of —O—Y—$X_2$ may be a para-position, a meta-position, or an ortho-position with respect to the bonding position of the benzene ring to the polymer main chain but is preferably a para-position.

In the present invention, the repeating unit represented by General Formula (1) is most preferably a repeating unit represented by the following General Formula (4').

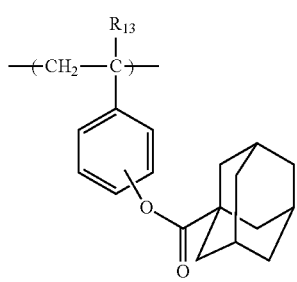

(4')

In General Formula (4'), $R_{13}$ represents a hydrogen atom or a methyl group.

In General Formula (4'), $R_{13}$ represents a hydrogen atom or a methyl group and is particularly preferably a hydrogen atom.

In General Formula (4'), the substitution position of the adamantyl ester group may be a para-position, a meta-position, or an ortho-position with respect to the bonding position of the benzene ring to the polymer main chain but is preferably a para-position.

Specific examples of the repeating unit having "a structure where a hydrogen atom of the phenolic hydroxyl group is substituted by a group having a non-acid-decomposable hydrocarbon structure" may include the followings.

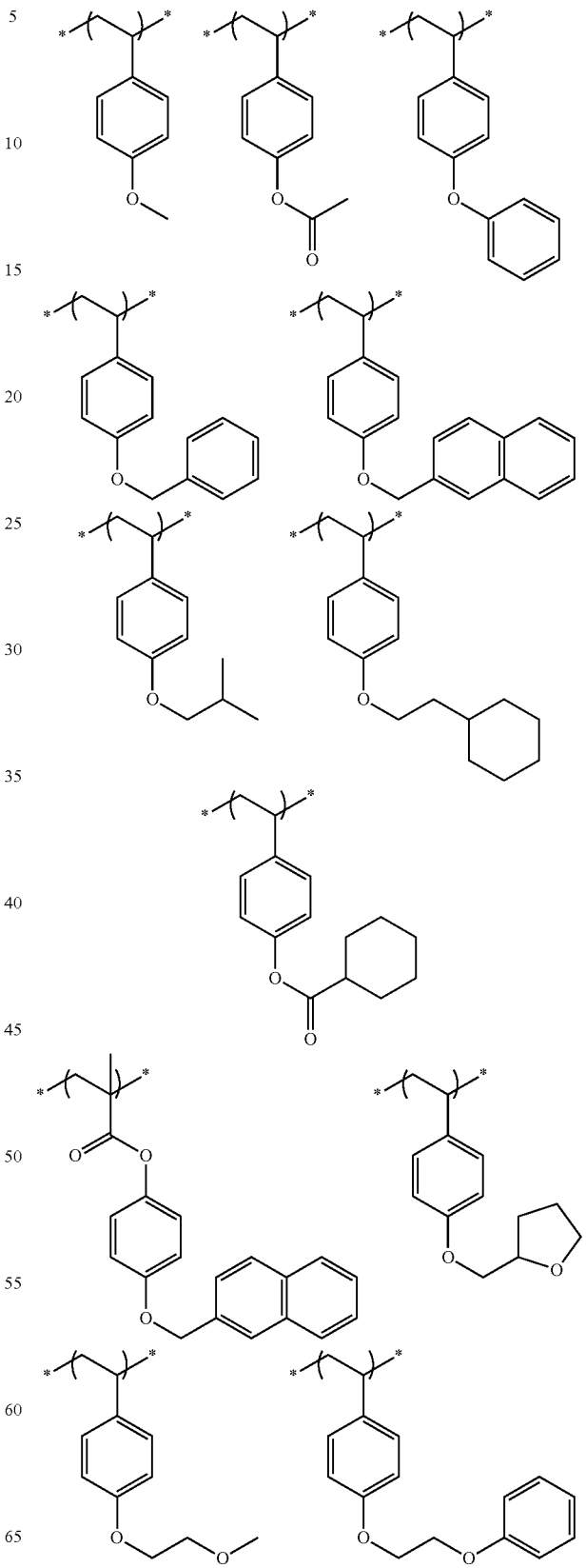

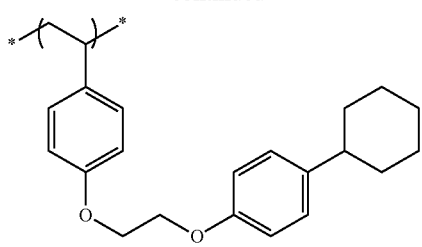
Among these, specific examples of the repeating unit represented by General Formula (4) are as follows.
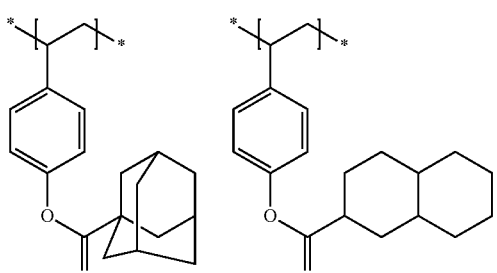
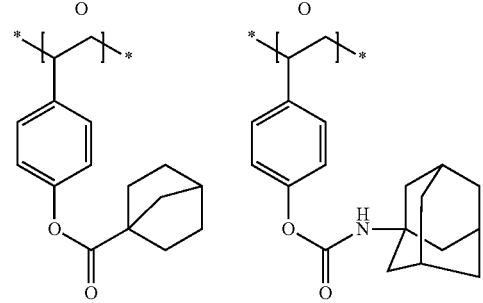
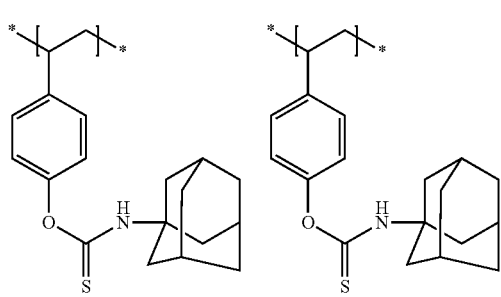
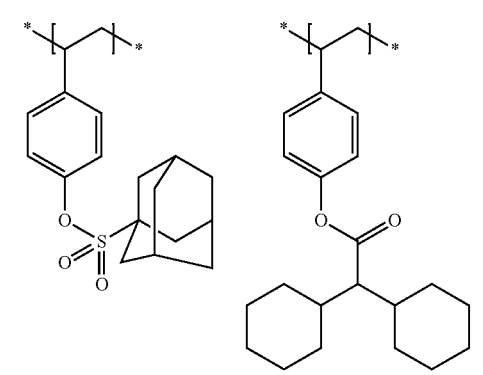
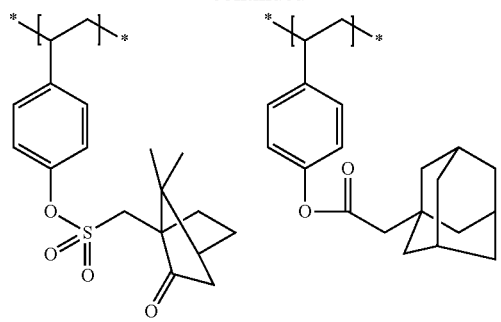
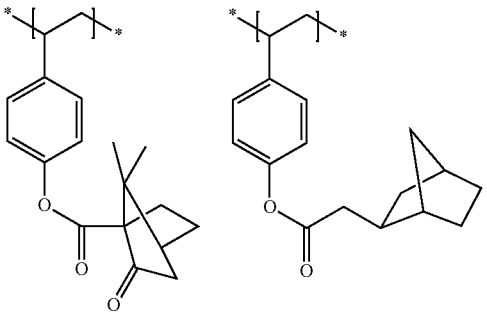
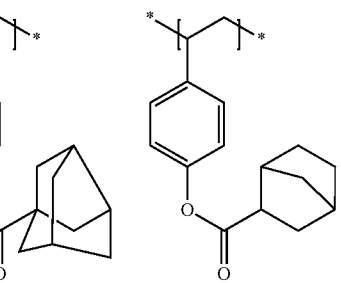
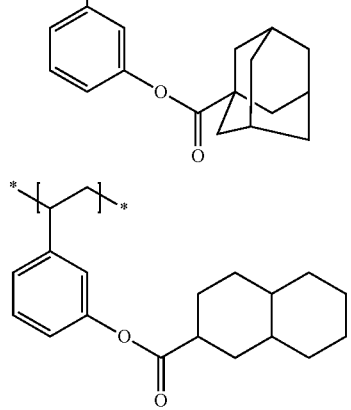
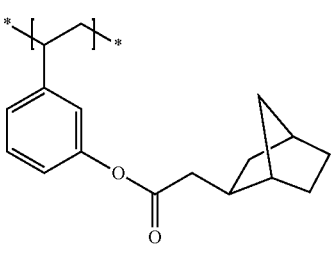

-continued
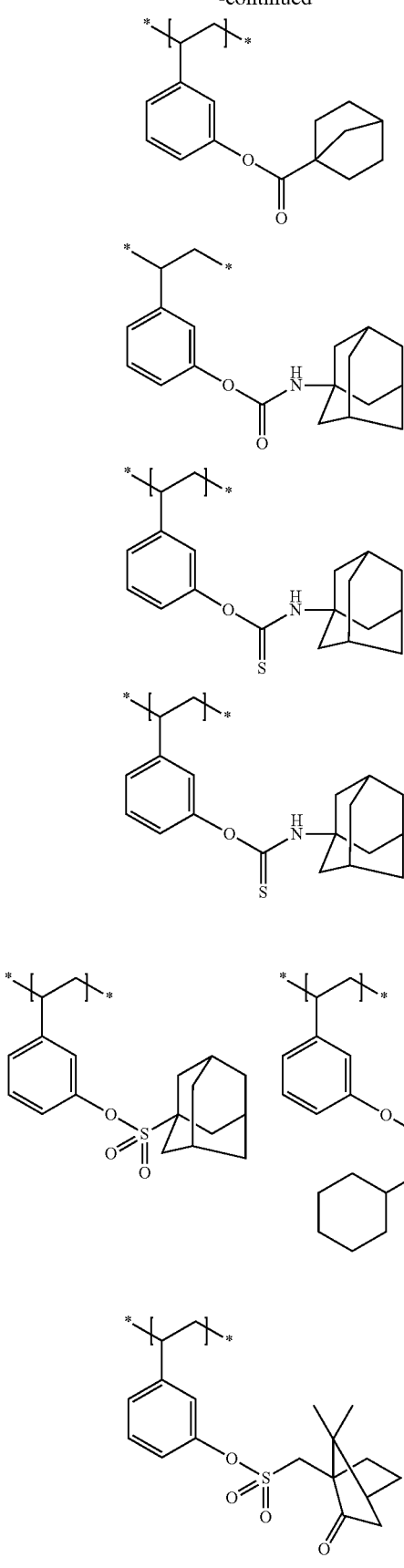
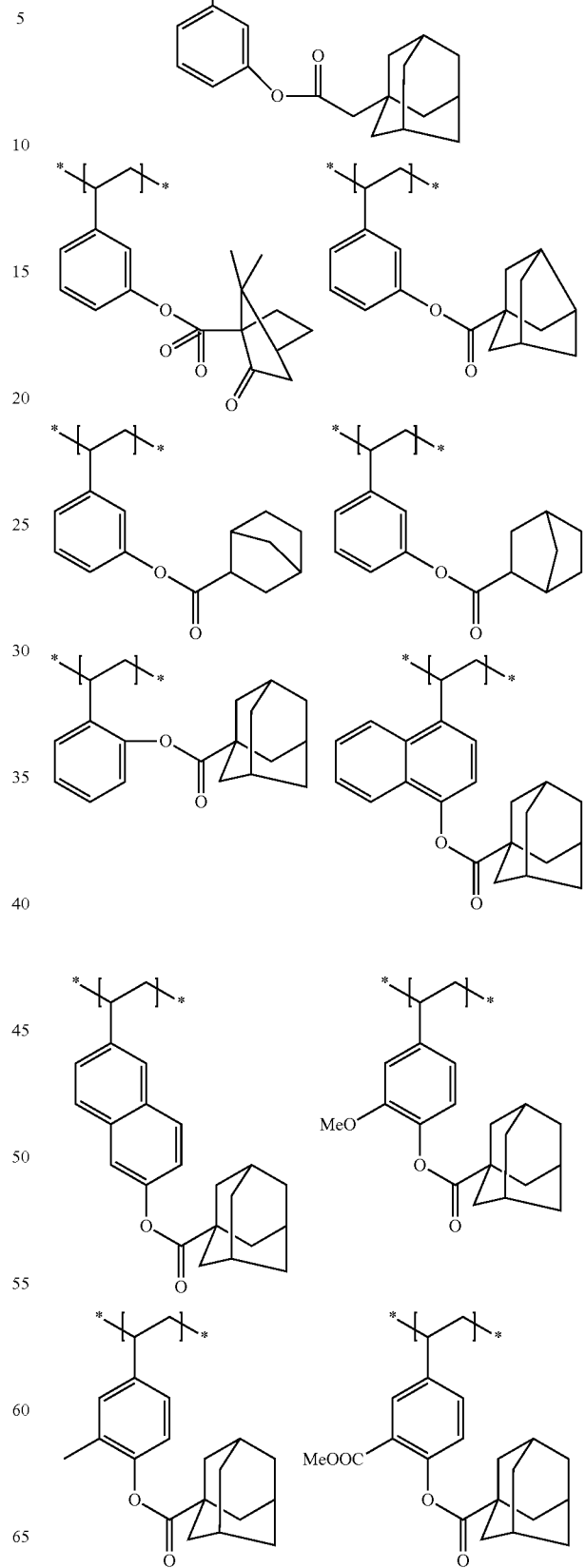

-continued

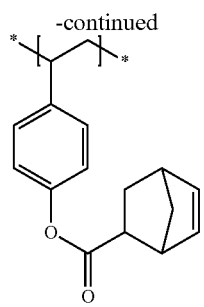

In the case where the resin (A) is a resin containing the repeating unit having "a structure where a hydrogen atom of the phenolic hydroxyl group is substituted by the above-mentioned group having a non-acid-decomposable hydrocarbon structure", the content of the repeating unit is preferably 1 mol % to 40 mol %, more preferably 2 mol % to 30 mol %, still more preferably 5 mol % to 20 mol %, and particularly preferably 10 mol % to 15 mol %, based on total repeating units constituting the resin (A).

The resin (A) may have a crosslinkable group, and preferably has a repeating unit containing a crosslinkable group.

Examples of the above-mentioned repeating unit containing a crosslinkable group may preferably include the following repeating unit (Q).

(a) Repeating unit (Q)

The repeating unit (Q) is a structure containing at least one methylol group which may have a substituent.

As used herein, the term "methylol group" is a group represented by the following General Formula (M), and in one embodiment of the present invention, it is preferably a hydroxymethyl group or an alkoxymethyl group.

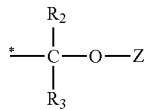

(M)

In the formula, $R_2$, $R_3$ and Z have the same definitions as in General Formula (Q-1) as described later.

First, General Formula (Q-1) will be described.

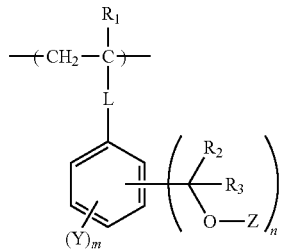

(Q-1)

In General Formula (Q-1), $R_1$ represents a hydrogen atom, a methyl group, or a halogen atom.

$R_2$ and $R_3$ represent a hydrogen atom, an alkyl group, or a cycloalkyl group.

L represents a divalent linking group or a single bond.

Y represents a monovalent substituent except for a methylol group.

Z represents a hydrogen atom or substituent.

m represents an integer of 0 to 4.

n represents an integer of 1 to 5.

m+n is 5 or less.

In the case where m is 2 or more, plural Y's may be the same as or different from each other.

In the case where n is 2 or more, plural $R_2$'s, $R_3$'s, and Z's may be the same as or different from each other.

Furthermore, any two or more of Y, $R_2$, $R_3$, and Z may be bonded to each other to form a ring structure. As used herein, the expression "any two or more of Y, $R_2$, $R_3$ and Z may be bonded to each other to form a ring structure" means that in the case where there are plural groups represented by the same symbols, the groups represented by the same symbols may be bonded to each other to form a ring structure, or the groups represented by different symbols may be bonded to each other to form a ring.

The methyl group represented by $R_1$ may have a substituent, and examples of the substituent may include halogen atoms such as a fluorine atom, a chlorine atom, a bromine atom, and an iodine atom, a hydroxyl group, and an isopropyl group. Examples of the methyl group which may have a substituent may include a methyl group, a trifluoromethyl group, and a hydroxymethyl group. Examples of the halogen atom of $R_1$ may include fluorine, chlorine, bromine, and iodine.

$R_1$ is preferably a hydrogen atom or a methyl group.

Examples of the alkyl group represented by $R_2$ and $R_3$ may include a linear or branched alkyl group having 1 to 10 carbon atoms, and examples of the cycloalkyl group may include a cycloalkyl group having 3 to 10 carbon atoms, and specifically a hydrogen atom, a methyl group, a cyclohexyl group, and a t-butyl group. The alkyl group and cycloalkyl group herein may have a substituent. Examples of the substituent may include the same ones described later as the substituent contained in the monovalent substituent of Y.

Examples of the divalent linking group represented by L may include a monocyclic or polycyclic aromatic ring having 6 to 18 carbon atoms, —C(=O)—, —O—C(=O)—, —CH$_2$—O—C(=O)—, a thiocarbonyl group, a linear or branched alkylene group (preferably having 1 to 10 carbon atoms, and more preferably 1 to 6 carbon atoms), a linear or branched alkenylene group (preferably having 2 to 10 carbon atoms, and more preferably 2 to 6 carbon atoms), a cycloalkylene group (preferably having 3 to 10 carbon atoms, and more preferably 3 to 6 carbon atoms), a sulfonyl group, —O—, —NH—, —S—, a cyclic lactone structure, or a divalent linking group of a combination thereof (preferably having 1 to 50 carbon atoms in total, more preferably 1 to 30 carbon atoms in total, and still more preferably 1 to 20 carbon atoms in total).

Preferred examples of the aromatic ring in L of General Formula (Q-1) include aromatic hydrocarbon rings having 6 to 18 carbon atoms which may have a substituent, such as a benzene ring, a naphthalene ring, an anthracene ring, a fluorene ring, and a phenanthrene ring; and aromatic heterocyclic rings containing a heterocyclic ring, such as a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, and a thiazole ring. Among them, a benzene ring and a naphthalene ring are preferred from the viewpoint of resolution, and a benzene ring is most preferred.

The divalent linking group represented by L may have a substituent, and examples of the substituent may include the substituents to be described later as the substituent contained in the monovalent substituent represented by Y.

Examples of the monovalent substituent represented by Y may include an alkyl group (which may be either linear or branched, and preferably has 1 to 12 carbon atoms), an alkenyl group (preferably having 2 to 12 carbon atoms), an alkynyl group (preferably having 2 to 12 carbon atoms), a cycloalkyl group (which may be either monocyclic or polycyclic and preferably has 3 to 12 carbon atoms), an aryl group (preferably having 6 to 18 carbon atoms), a hydroxy group, an alkoxy group, an ester group, an amido group, a urethane group, an ureido group, a thioether group, a sulfonamide group, a halogen atom, a haloalkyl group, and a sulfonic acid ester group. Preferred examples thereof may include an alkyl group, a cycloalkyl group, a halogen atom, a haloalkyl group, a hydroxy group, an alkoxy group, an aryloxy group, an ester group, and an aryl group, and more preferred examples thereof include an alkyl group, a halogen atom a hydroxy group, and an alkoxy group.

The monovalent substituent of Y may further have a substituent, and examples of the substituent may include a hydroxyl group, a halogen atom (for example, a fluorine atom), an alkyl group, a cycloalkyl group, an alkoxy group, a carboxyl group, an alkoxycarbonyl group, an aryl group, an alkoxyalkyl group, and a group formed by combining these groups, preferably having 8 or less carbon atoms.

In addition, when m is 2 or more, plural Y's may be bonded to each other via a single bond or a linking group to form a ring structure. Examples of the linking group in this case may include an ether bond, a thioether bond, an ester bond, an amido bond, a carbonyl group, and an alkylene group.

Examples of the halogen atom may include the same those as mentioned for the substituent which may be contained in the methyl group represented by $R_1$.

Examples of the haloalkyl group may include an alkyl group having 1 to 12 carbon atoms, and a cycloalkyl group, in each of which at least one or more hydrogen atoms are substituted with a fluorine atom, a chlorine atom, a bromine atom, and an iodine atom. Specific examples thereof may include a fluoromethyl group, a trifluoromethyl group, a pentafluoroethyl group, a heptafluoropropyl group, and an undecafluorocyclohexyl group.

Examples of the monovalent substituent represented by Z may include an alkyl group (which may be either linear or branched, and preferably has 1 to 12 carbon atoms), an alkenyl group (preferably having 2 to 12 carbon atoms), an alkynyl group (preferably having 2 to 12 carbon atoms), a cycloalkyl group (preferably having 3 to 8 carbon atoms), an aryl group (which may be either monocyclic or polycyclic, and preferably has 6 to 18 carbon atoms), a haloalkyl group, an alkanoyl group, an alkoxycarbonyl group, an aryloxycarbonyl group, an alkylsulfonyloxy group, an arylsulfonyloxy group, an alkylsulfonyl group, an arylsulfonyl group, a cyano group, an alkylthio group, an arylthio group, an alkoxyalkyl group and a heterocyclic group. Preferred examples thereof may include a hydrogen atom, an alkyl group, a cycloalkyl group, an alkanoyl group, an alkenyl group, a haloalkyl group, and an alkoxyalkyl group.

Preferred examples of the haloalkyl group include the same as mentioned for Y in General Formula (Q-1).

The alkanoyl group is preferably an alkanoyl group having 2 to 20 carbon atoms, and examples thereof may include an acetyl group, a propanoyl group, a butanoyl group, a trifluoromethylcarbonyl group, a pentanoyl group, a benzoyl group, a 1-naphthoyl group, a 2-naphthoyl group, a 4-methylsulfanylbenzoyl group, a 4-phenylsulfanylbenzoyl group, a 4-dimethylaminobenzoyl group, a 4-diethylaminobenzoyl group, a 2-chlorobenzoyl group, a 2-methylbenzoyl group, a 2-methoxybenzoyl group, a 2-butoxybenzoyl group, a 3-chlorobenzoyl group, a 3-trifluoromethylbenzoyl group, a 3-cyanobenzoyl group, a 3-nitrobenzoyl group, a 4-fluorobenzoyl group, a 4-cyanobenzoyl group, and a 4-methoxybenzoyl group.

The alkoxycarbonyl group is preferably an alkoxycarbonyl group having 2 to 20 carbon atoms, and examples thereof may include a methoxycarbonyl group, an ethoxycarbonyl group, a propoxycarbonyl group, a butoxycarbonyl group, a hexyloxycarbonyl group, an octyloxycarbonyl group, a decyloxycarbonyl group, an octadecyloxycarbonyl group, and a trifluoromethyloxycarbonyl group.

Examples of the aryloxycarbonyl group may include aryloxycarbonyl groups having 7 to 30 carbon atoms, for example, a phenoxycarbonyl group, a 1-naphthyloxycarbonyl group, a 2-naphthyloxycarbonyl group, a 4-methylsulfanylphenyloxycarbonyl group, a 4-phenylsulfanylphenyloxycarbonyl group, a 4-dimethylaminophenyloxycarbonyl group, a 4-diethylaminophenyloxycarbonyl group, a 2-chlorophenyloxycarbonyl group, a 2-methylphenyloxycarbonyl group, a 2-methoxyphenyloxycarbonyl group, a 2-butoxyphenyloxycarbonyl group, a 3-chlorophenyloxycarbonyl group, a 3-trifluoromethylphenyloxycarbonyl group, a 3-cyanophenyloxycarbonyl group, a 3-nitrophenyloxycarbonyl group, a 4-fluorophenyloxycarbonyl group, a 4-cyanophenyloxycarbonyl group, and a 4-methoxyphenyloxycarbonyl group.

The alkylsulfonyloxy group is preferably an alkylsulfonyloxy group having 1 to 20 carbon atoms, and examples thereof may include a methylsulfonyloxy group, an ethylsulfonyloxy group, a propylsulfonyloxy group, an isopropylsulfonyloxy group, a butylsulfonyloxy group, a hexylsulfonyloxy group, a cyclohexylsulfonyloxy group, an octylsulfonyloxy group, a 2-ethylhexylsulfonyloxy group, a decanoylsulfonyloxy group, a dodecanoylsulfonyloxy group, an octadecanoylsulfonyloxy group, a cyanomethylsulfonyloxy group, a methoxymethylsulfonyloxy group, and a perfluoroalkylsulfonyloxy group.

The arylsulfonyloxy group is preferably an arylsulfonyloxy group having 6 to 30 carbon atoms, and examples thereof may include a phenylsulfonyloxy group, a 1-naphthylsulfonyloxy group, a 2-naphthylsulfonyloxy group, a 2-chlorophenylsulfonyloxy group, a 2-methylphenylsulfonyloxy group, a 2-methoxyphenylsulfonyloxy group, a 2-butoxyphenylsulfonyloxy group, a 3-chlorophenylsulfonyloxy group, a 3-trifluoromethylphenylsulfonyloxy group, a 3-cyanophenylsulfonyloxy group, a 3-nitrophenylsulfonyloxy group, a 4-fluorophenylsulfonyloxy group, a 4-cyanophenylsulfonyloxy group, a 4-methoxyphenylsulfonyloxy group, a 4-methylsulfanylphenylsulfonyloxy group, a 4-phenylsulfanylphenylsulfonyloxy group, and a 4-dimethylaminophenylsulfonyloxy group.

The alkylsulfonyl group is preferably an alkylsulfonyl group having 1 to 20 carbon atoms, and examples thereof may include a methylsulfonyl group, an ethylsulfonyl group, a propylsulfonyl group, an isopropylsulfonyl group, a butylsulfonyl group, a hexylsulfonyl group, a cyclohexylsulfonyl group, an octylsulfonyl group, a 2-ethylhexylsulfonyl group, a decanoylsulfonyl group, a dodecanoylsulfonyl group, an octadecanoylsulfonyl group, a cyanomethylsulfonyl group, a methoxymethylsulfonyl group, and a perfluoroalkylsulfonyl group.

The arylsulfonyl group is preferably an arylsulfonyl group having 6 to 30 carbon atoms, and examples thereof may include a phenylsulfonyl group, a 1-naphthylsulfonyl group, a 2-naphthylsulfonyl group, a 2-chlorophenylsulfonyl group, a 2-methylphenylsulfonyl group, a 2-methoxyphenylsulfonyl group, a 2-butoxyphenylsulfonyl group, a 3-chlorophenylsulfonyl group, a 3-trifluoromethylphenylsulfonyl group, a 3-cyanophenylsulfonyl group, a 3-nitrophenylsulfonyl group, a 4-fluorophenylsulfonyl group, a 4-cyanophenylsulfonyl group, a 4-methoxyphenylsulfonyl group, a 4-methylsulfanylphenylsulfonyl group, a 4-phenylsulfanylphenylsulfonyl group, and a 4-dimethylaminophenylsulfonyl group.

Examples of the alkylthio group may include alkylthio groups having 1 to 30 carbon atoms, for example, a methylthio group, an ethylthio group, a propylthio group, an n-butylthio group, a trifluoromethylthio group, a hexylthio group, a t-butylthio group, a 2-ethylhexylthio group, a cyclohexylthio group, a decylthio group, and a dodecylthio group.

Examples of the arylthio group may include arylthio groups having 6 to 30 carbon atoms, for example, a phenylthio group, a 1-naphthylthio group, a 2-naphthylthio group, a tolylthio group, a methoxyphenylthio group, a naphthylthio group, a chlorophenylthio group, a trifluoromethylphenylthio group, a cyanophenylthio group, and a nitrophenylthio group.

Preferred examples of the heterocyclic group may include aromatic or aliphatic heterocyclic groups containing a nitrogen atom, an oxygen atom, a sulfur atom or a phosphorous atom, such as a thienyl group, a benzo[b]thienyl group, a naphtho[2,3-b]thienyl group, a thianthrenyl group, a furyl group, a pyranyl group, an isobenzofuranyl group, a chromenyl group, a xanthenyl group, a phenoxathiinyl group, a 2H-pyrrolyl group, a pyrrolyl group, an imidazolyl group, a pyrazolyl group, a pyridyl group, a pyrazinyl group, a pyrimidinyl group, a pyridazinyl group, an indolizinyl group, an isoindolyl group, a 3H-indolyl group, an indolyl group, a 1H-indazolyl group, a purinyl group, a 4H-quinolidinyl group, an isoquinolyl group, a quinolyl group, a phthalazinyl group, a naphthyridinyl group, a quinoxalinyl group, a quinazolinyl group, a cinnolinyl group, a pteridinyl group, a 4aH-carbazolyl group, a carbazolyl group, a β-carbolinyl group, a phenanthridinyl group, an acridinyl group, a perimidinyl group, a phenanthrolinyl group, a phenazinyl group, a phenarsazinyl group, an isothiazolyl group, a phenothiazinyl group, an isoxazolyl group, a furazanyl group, a phenoxazinyl group, an isochromanyl group, a chromanyl group, a pyrrolidinyl group, a pyrrolinyl group, an imidazolidinyl group, an imidazolinyl group, a pyrazolidinyl group, a pyrazolinyl group, a piperidyl group, a piperazinyl group, an indolinyl group, an isoindolinyl group, a quinuclidinyl group, a tetrahydropyrimidinyl group, a tetrahydro-2-pyrimidinonyl group, a triazinyl group, a morpholinyl group, and a thioxanthryl group.

n preferably represents an integer of 1 to 4, more preferably an integer of 2 to 4, and particularly preferably 2 or 3, m is preferably 0 or 1.

Moreover, the repeating unit (Q) represented by General Formula (Q-1) is preferably a repeating unit represented by the following General Formula (2) or (3).

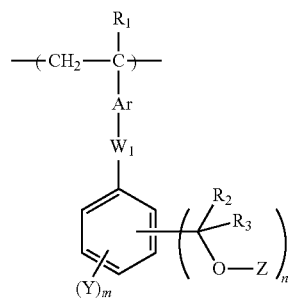

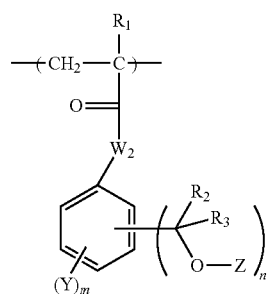

In General Formulae (2) and (3), $R_1$, $R_2$, $R_3$, Y, Z, m, and n are as defined in General Formula (Q-1).

Ar represents an aromatic ring.

$W_1$ and $W_2$ represent a divalent linking group or a single bond.

Specific examples of $R_1$, $R_2$, $R_3$, Y, Z, m, and n may include the same as those mentioned in General Formula (Q-1), respectively, and the preferred ranges thereof are also the same.

Specific examples of the aromatic ring represented by Ar may include the same as the specific examples in the case where L in General Formula (Q-1) is an aromatic ring, and the preferred ranges thereof are also the same.

Examples of the divalent linking group represented by $W_1$ and $W_2$ may include a monocyclic or polycyclic aromatic hydrocarbon ring having 6 to 18 carbon atoms which may have a substituent, —C(=O)—, —O—C(=O)—, —CH$_2$—O—C(=O)—, a thiocarbonyl group, a linear or branched alkylene group (preferably having 1 to 10 carbon atoms, and more preferably 1 to 6 carbon atoms), a linear or branched alkenylene group (preferably having 2 to 10 carbon atoms, and more preferably 2 to 6 carbon atoms), a cycloalkylene group (preferably having 3 to 10 carbon atoms, and more preferably 5 to 10 carbon atoms), a sulfonyl group, —O—, —NH—, —S—, a cyclic lactone structure, or a divalent linking group of a combination thereof.

Furthermore, the repeating unit (Q) represented by General Formula (Q-1) is more preferably represented by the following General Formula (2') or (3').

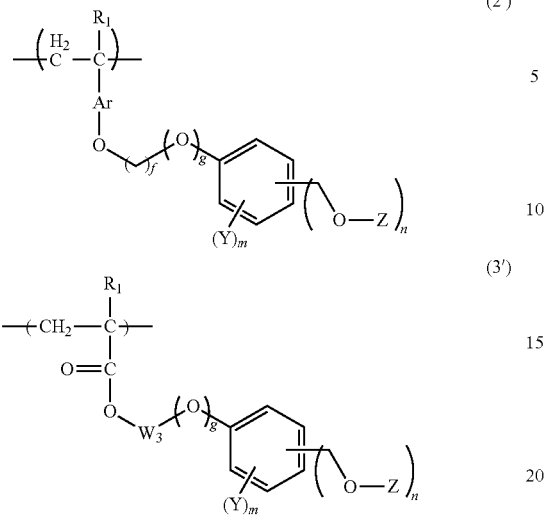

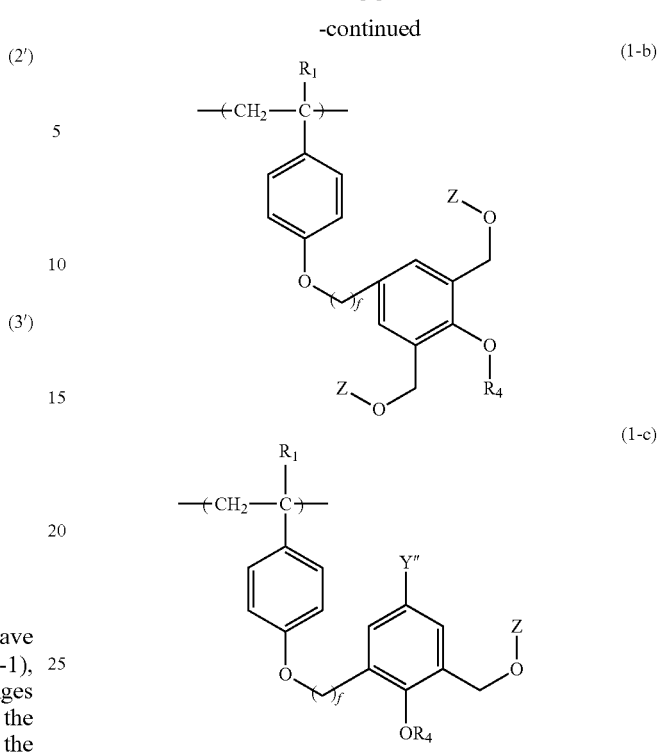

In General Formulae (2') and (3'), $R_1$, Y, Z, m and n have the same definitions as the groups in General Formula (Q-1), respectively, and specific examples and the preferred ranges thereof are also the same. Ar in General Formula (2') has the same definition as Ar in General Formula (2), and the preferred ranges thereof are also the same.

$W_3$ in General Formula (3') is a divalent linking group. Examples of the divalent linking group represented by $W_3$ may include a monocyclic or polycyclic aromatic hydrocarbon ring having 6 to 18 carbon atoms which may have a substituent, —C(=O)—, a linear or branched alkylene group (preferably having 1 to 10 carbon atoms, and more preferably 1 to 6 carbon atoms), a cycloalkylene group (preferably having 3 to 10 carbon atoms, and more preferably 5 to 10 carbon atoms), —O—, a cyclic lactone structure, or a divalent linking group of a combination thereof.

In General Formula (2'), f is an integer of 0 to 6, preferably an integer of 0 to 3, and more preferably an integer of 1 to 3.

In General Formulae (2') and (3'), g is 0 or 1.

Furthermore, General Formula (2') is particularly preferably represented by any one of the following General Formulae (1-a) to (1-c). The repeating unit (Q) is particularly preferably a repeating unit represented by any one of the following General Formulae (1-a) to (1-c), or a repeating unit represented by General Formula (3').

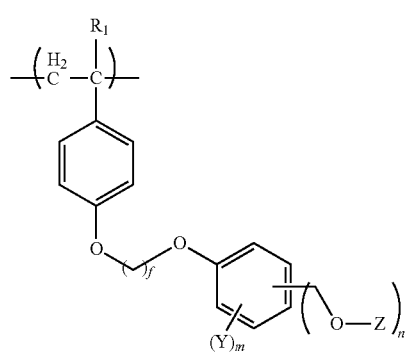

$R_1$, Y, and Z in General Formulae (1-a) to (1-c) have the same definitions as the groups in General Formula (Q-1), respectively, and the specific examples and the preferred ranges thereof are also the same.

In General Formulae (1-b) to (1-c),

Y" represents a hydrogen atom or a monovalent substituent. Examples of the monovalent substituent may include the same as the monovalent substituent represented by Y as described above. However, Y" may be a methylol group.

$R_4$ represents a hydrogen atom or a monovalent substituent. Specific examples of the monovalent substituent may include the same as those in the case where Z in General Formula (Q-1) is a monovalent substituent.

f is an integer of 1 to 6. The preferred range thereof is as mentioned in General Formula (2').

m is 0 or 1 and n is an integer of 1 to 3.

In General Formulae (1-b) and (1-c), examples of $R_4$ may include a hydrogen atom, an alkyl group (which may be either linear or branched and preferably has 1 to 12 carbon atoms), an alkenyl group (preferably having 2 to 12 carbon atoms), an alkynyl group (preferably having 2 to 12 carbon atoms), a cycloalkyl group (preferably having 3 to 8 carbon atoms), an aryl group (which may be either monocyclic or polycyclic and preferably has 6 to 18 carbon atoms), a haloalkyl group, an alkanoyl group, an alkoxycarbonyl group, an aryloxycarbonyl group, an alkylsulfonyloxy group, an arylsulfonyloxy group, an alkylsulfonyl group, an arylsulfonyl group, a cyano group, an alkylthio group, an arylthio group, and a heterocyclic group. Preferable examples thereof include a hydrogen atom, an alkyl group, a cycloalkyl group, and an alkanoyl group.

Specific examples of the haloalkyl group, the alkanoyl group, the alkoxycarbonyl group, the aryloxycarbonyl group, the alkylsulfonyloxy group, the arylsulfonyloxy group, the alkylsulfonyl group, the arylsulfonyl group, the cyano group, the alkylthio group, the arylthio group, and the heterocyclic group are the same as those for Z in General Formula (Q-1), and the preferred ranges thereof are also the same.

The content of the repeating unit (Q) is preferably 5 mol % to 50 mol %, more preferably 5 mol % to 40 mol %, still more preferably 5 mol % to 20 mol %, and particularly preferably 5 mol % to 15 mol %, based on the total repeating units included in the resin (A) from the viewpoints of crosslinking efficiency and developability.

Specific examples of the repeating unit (Q) may include the following structures.

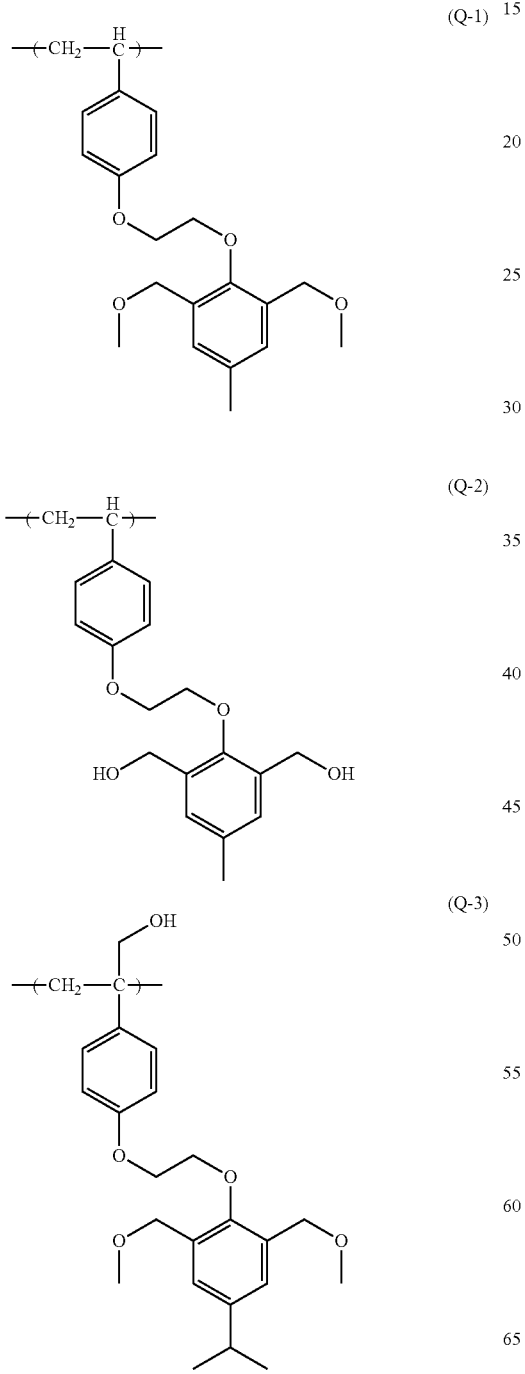

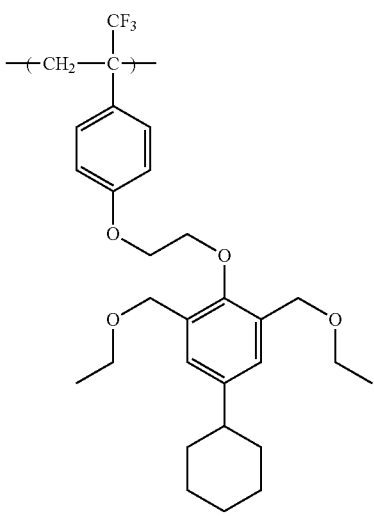

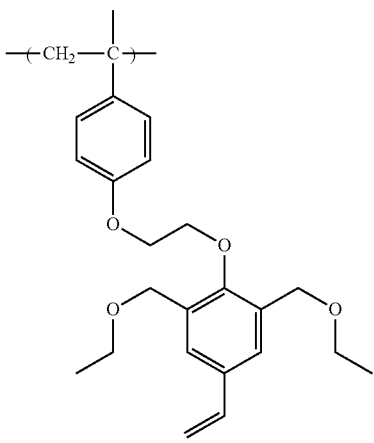

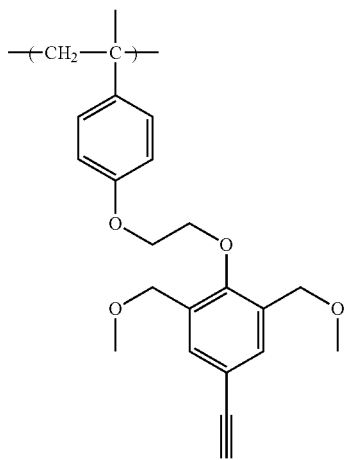

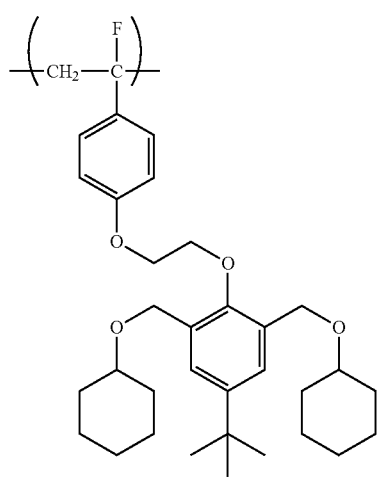
(Q-7)
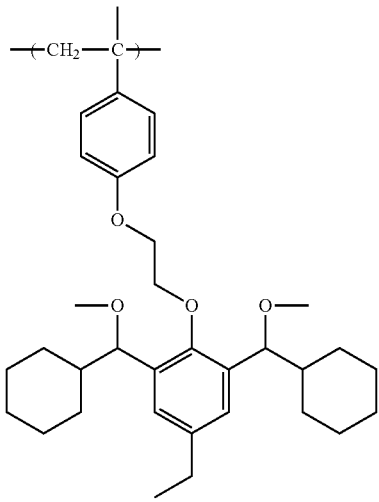
(Q-10)
(Q-8)
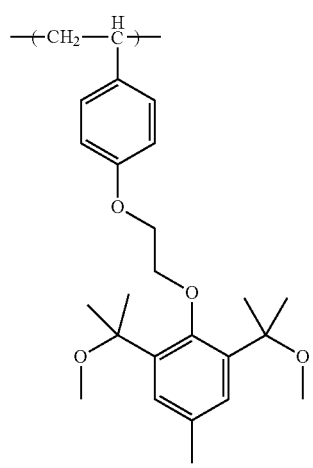
(Q-11)
(Q-9)
(Q-12)

-continued
(Q-13)
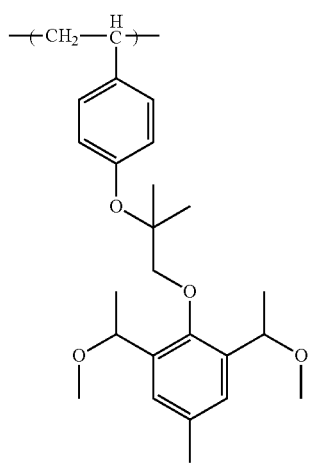
(Q-14)
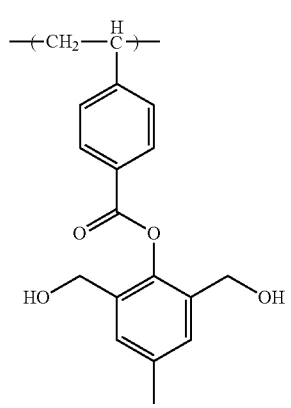
(Q-15)
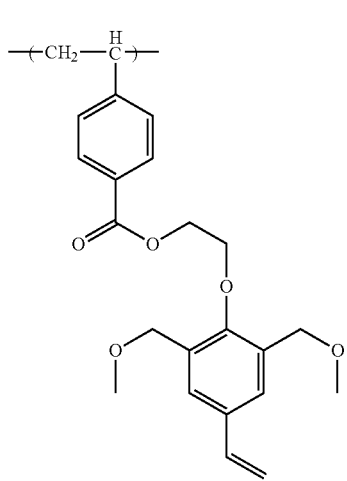
(Q-16)
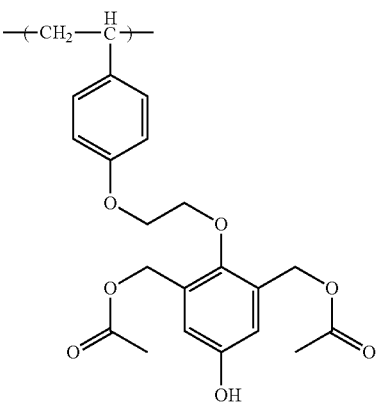
(Q-17)
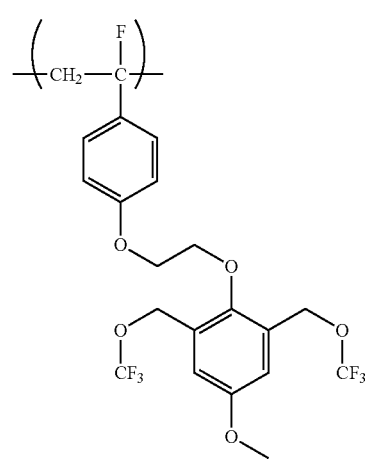
(Q-18)
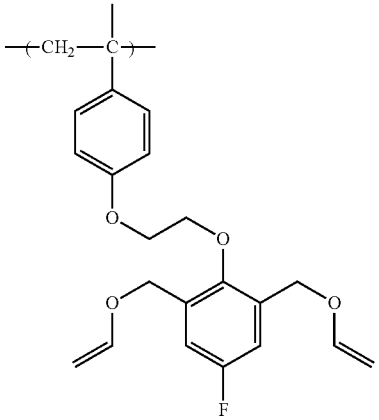

(Q-19)
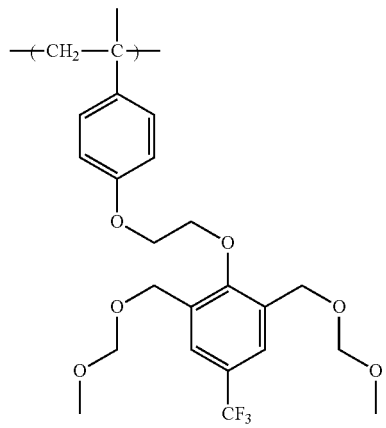
(Q-20)
(Q-21)
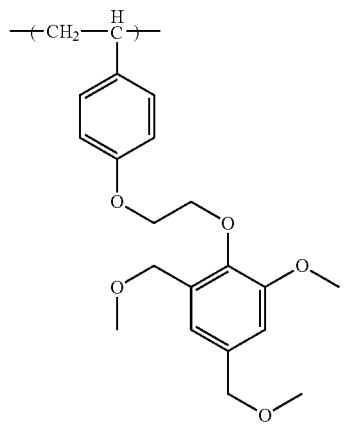
(Q-22)
(Q-23)
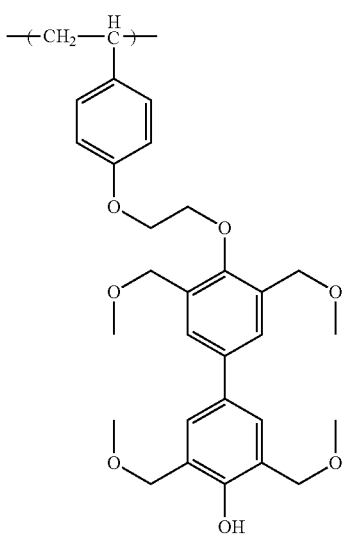
(Q-24)
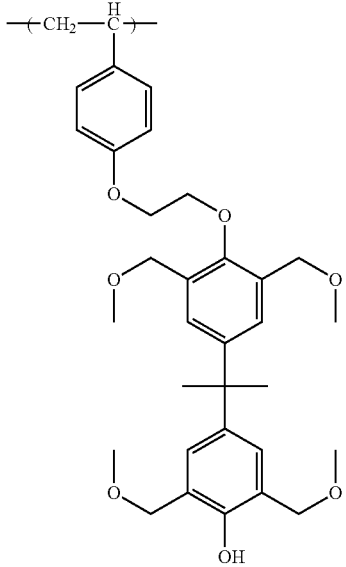

(Q-25) 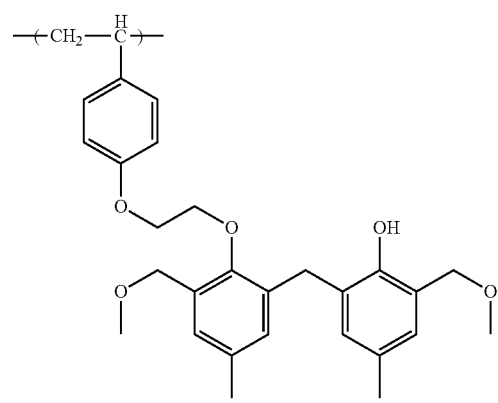
(Q-26) 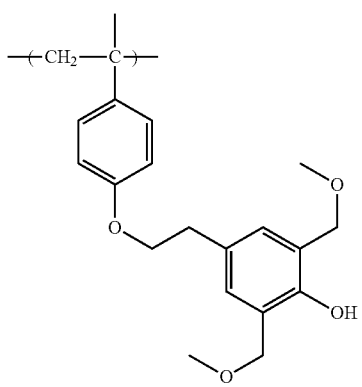
(Q-27) 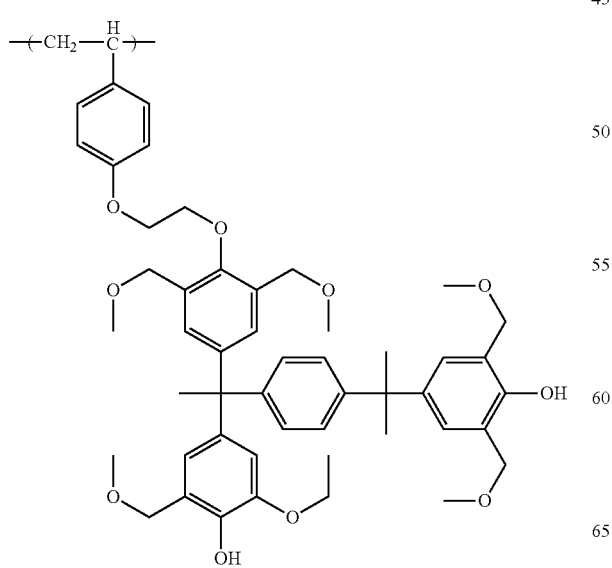
(Q-28) 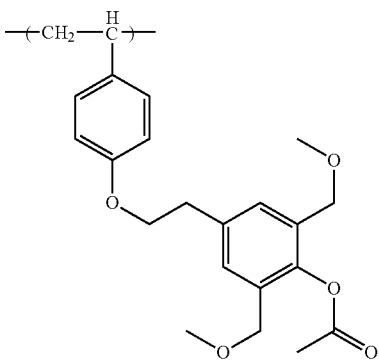
(Q-29) 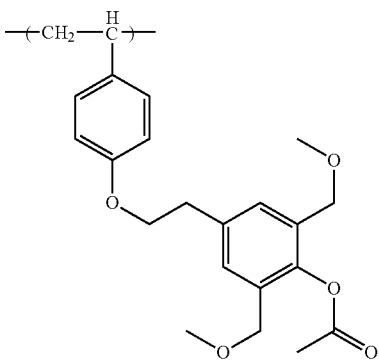
(Q-30) 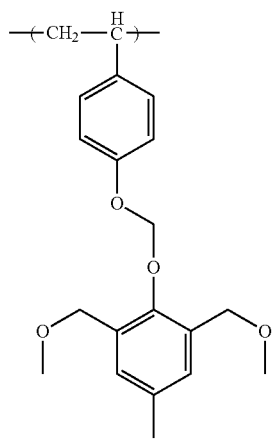
(Q-31) 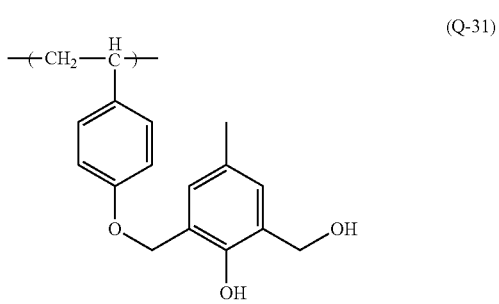

(Q-32)
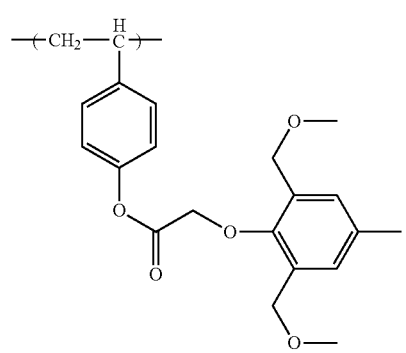
(Q-33)
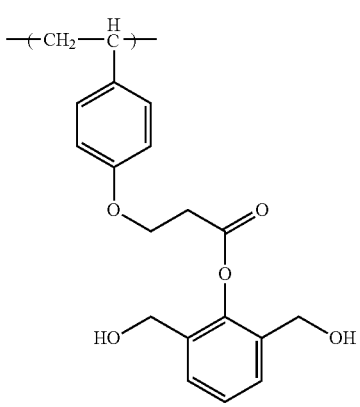
(Q-34)
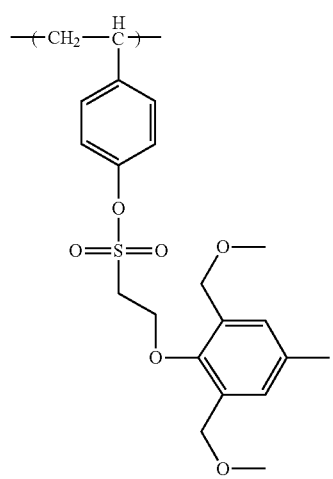
(Q-35)
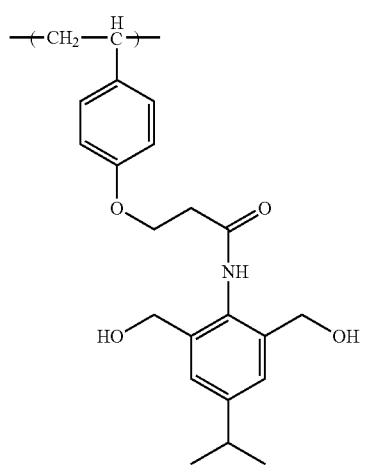
(Q-36)
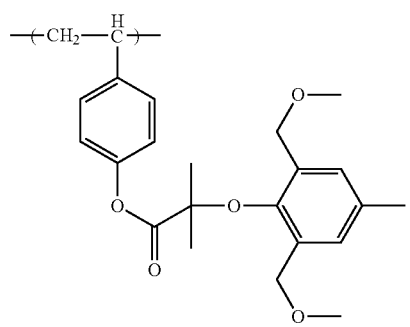
(Q-37)
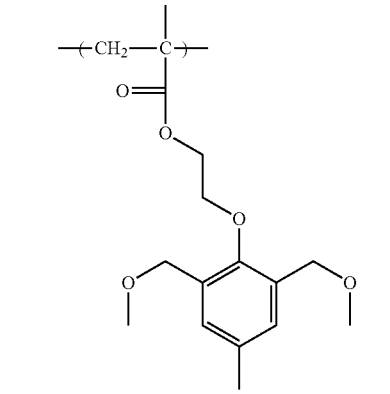
(Q-38)
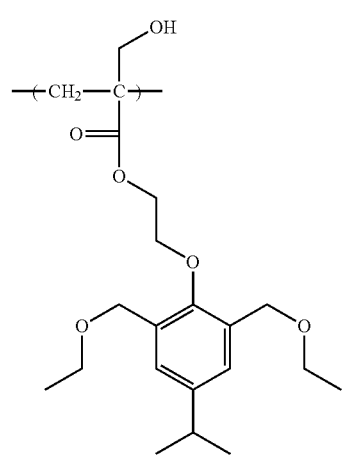

(Q-39) 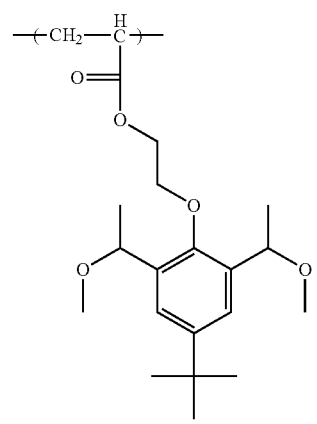
(Q-40) 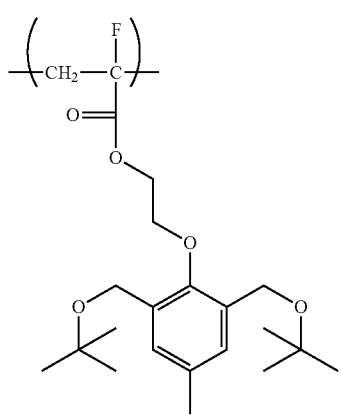
(Q-41) 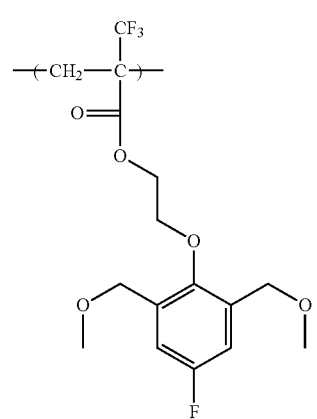
(Q-42) 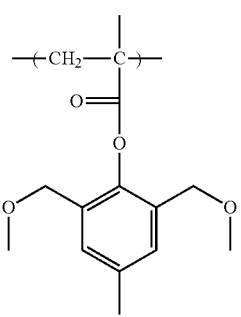
(Q-43) 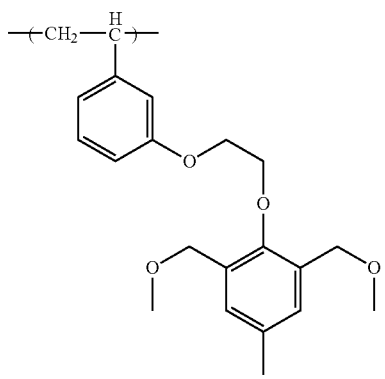
(Q-44) 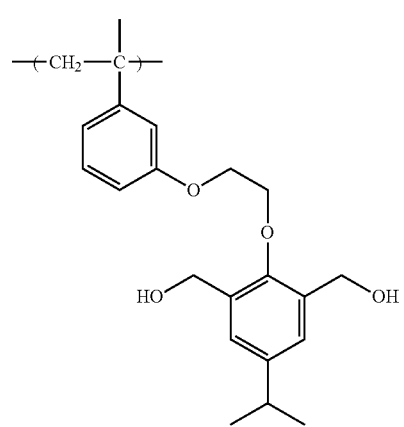
(Q-45) 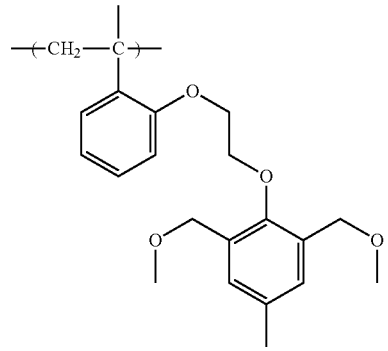
(Q-46) 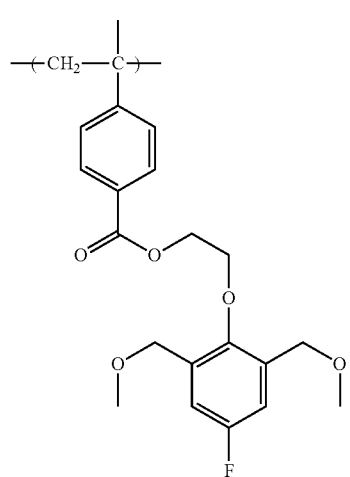

(Q-47) 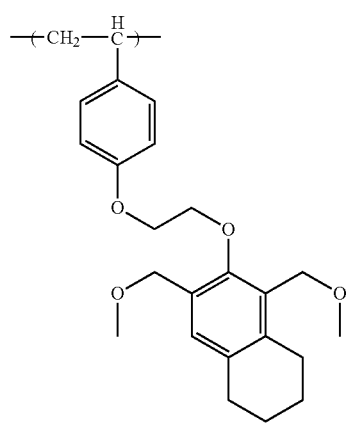
(Q-48) 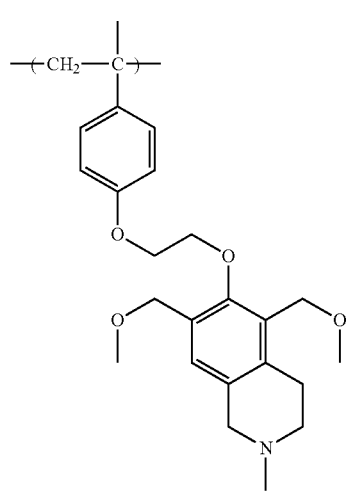
(Q-49)
(Q-50) 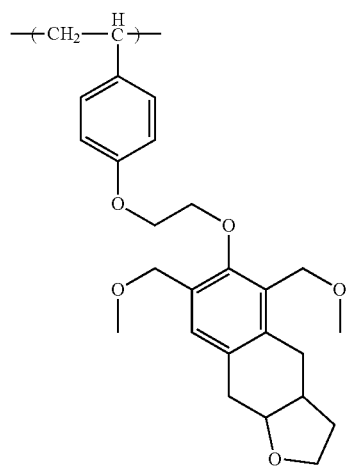
(Q-51) 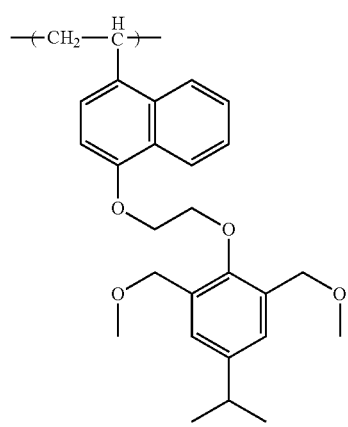
(Q-52) 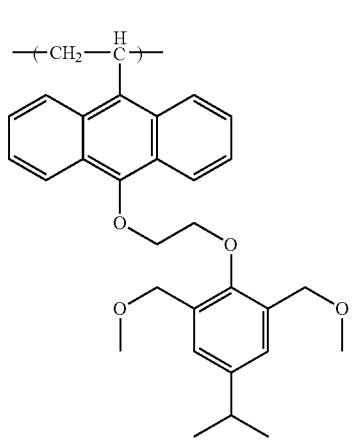

(Q-53)
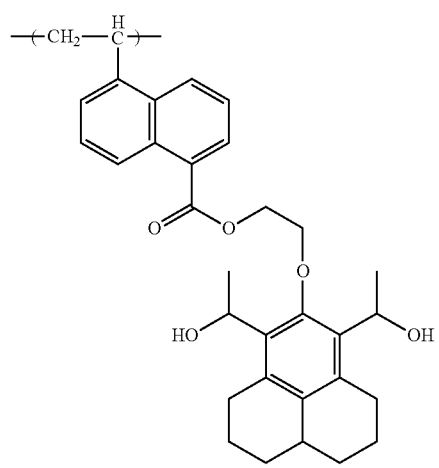
(Q-56)
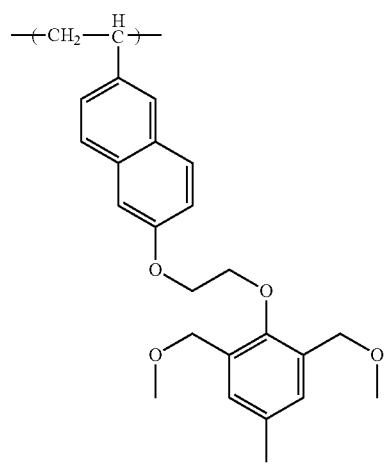
(Q-54)
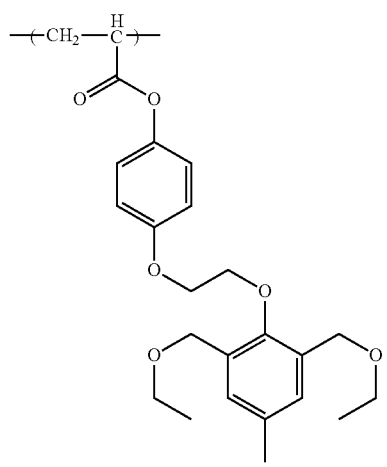
(Q-57)
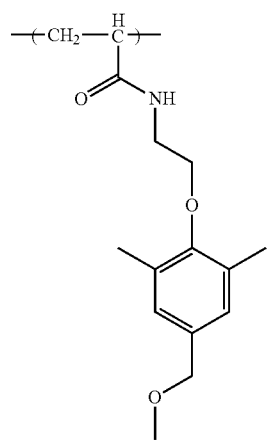
(Q-55)
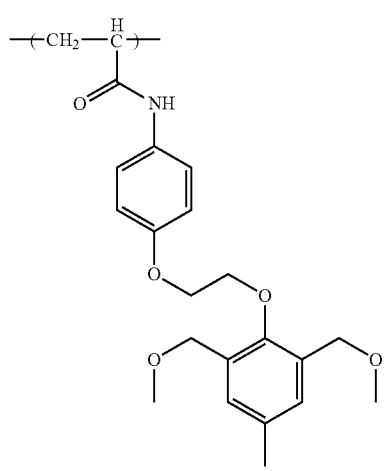
(Q-58)
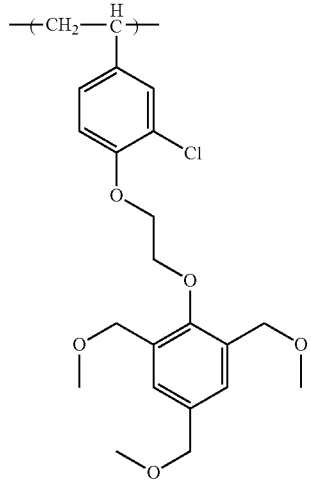

-continued
(Q-59)
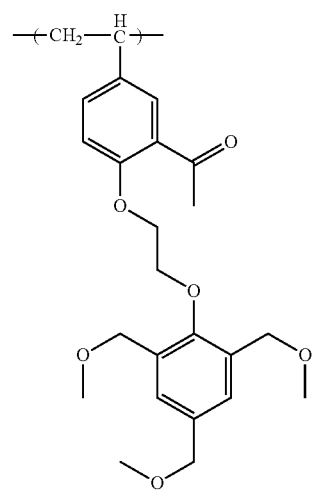
(Q-60)
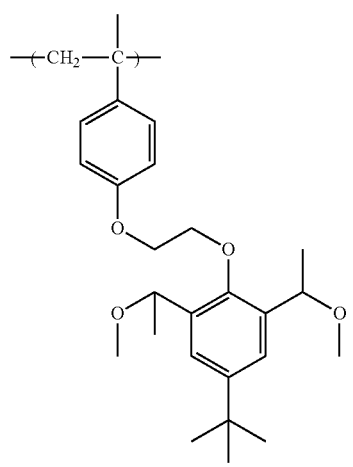
(Q-61)
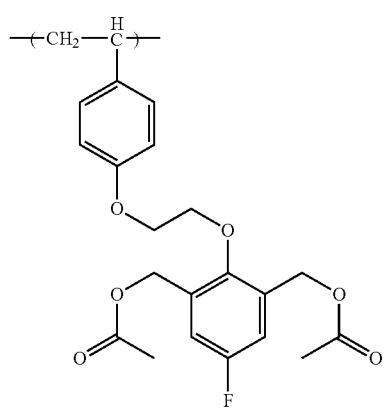
-continued
(Q-62)
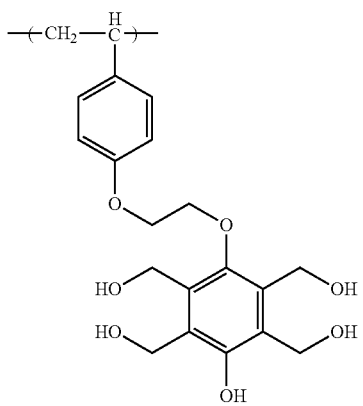
(Q-63)
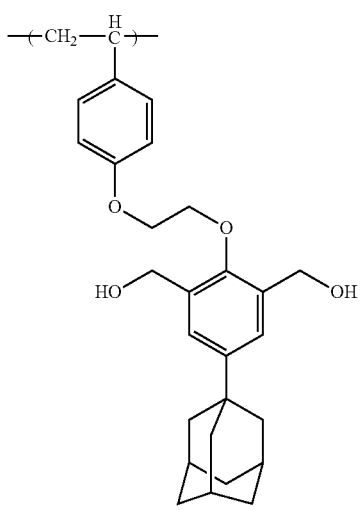
(Q-64)
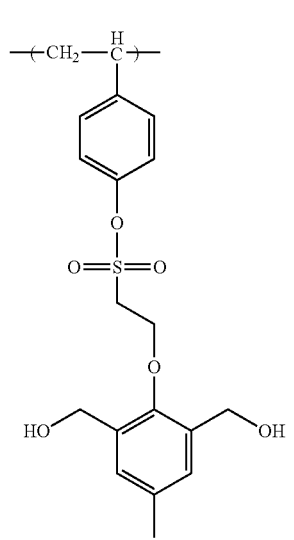

(Q-65)
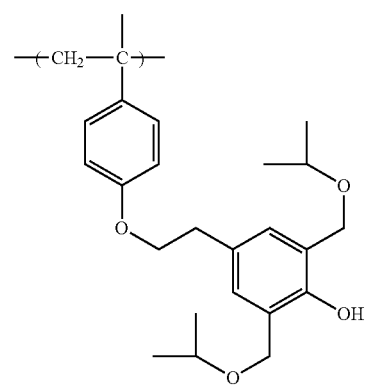
(Q-68)
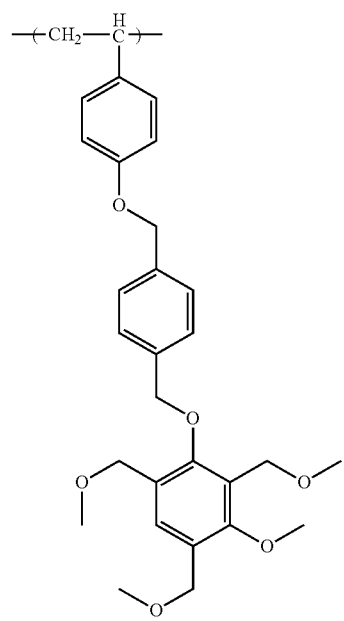
(Q-66)
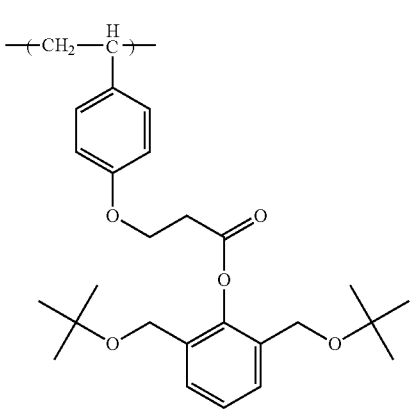
(Q-69)
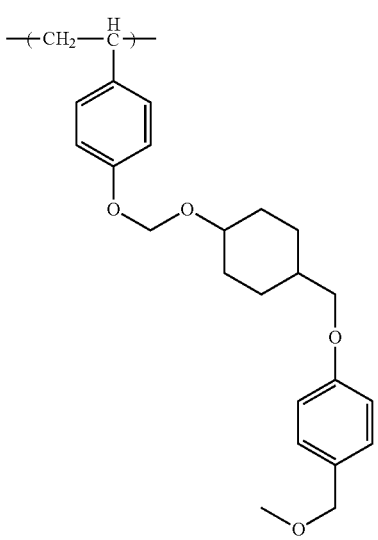
(Q-67)
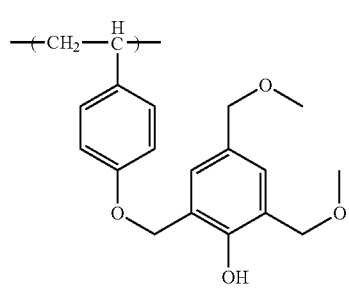
(Q-70)
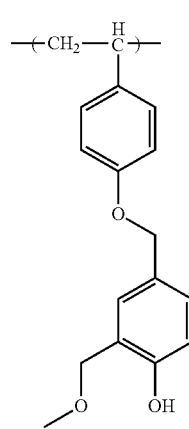

(Q-71)
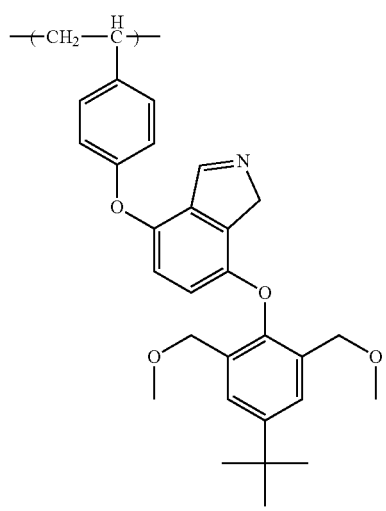
(Q-72)
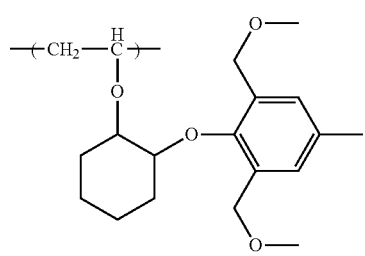
(Q-73)
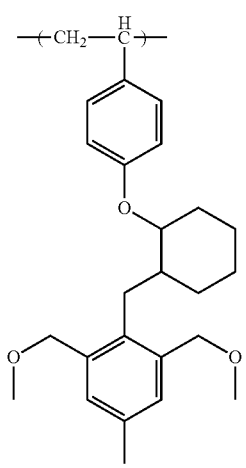
(Q-74)
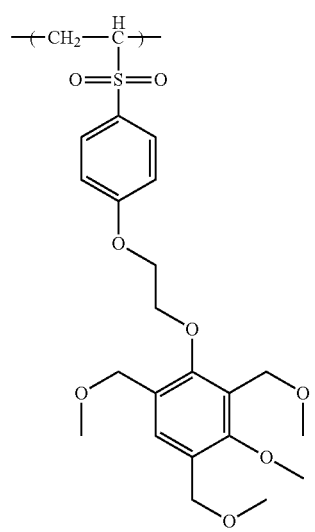
(Q-75)
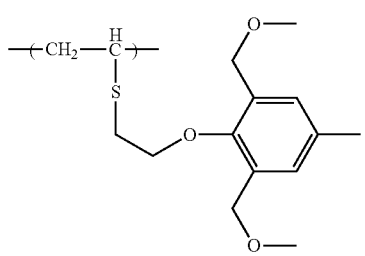
(Q-76)
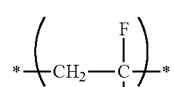
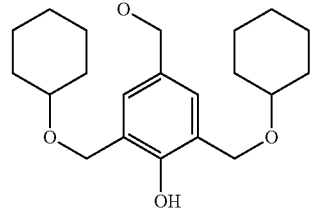
(Q-77)
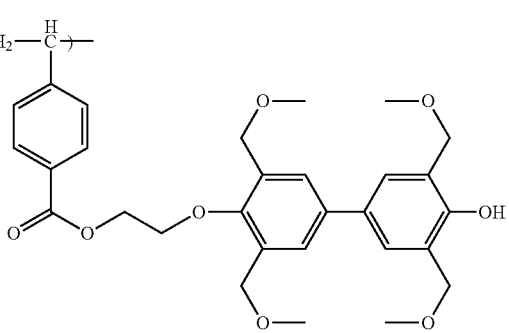

(Q-78) 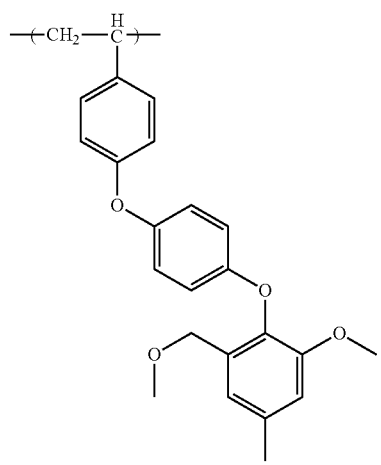
(Q-79) 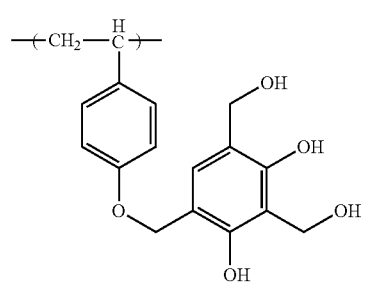
(Q-80) 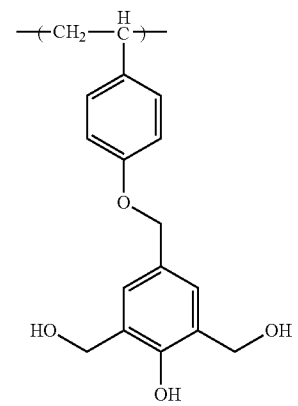
(Q-81) 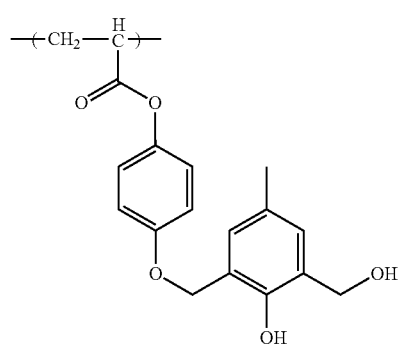
(Q-89) 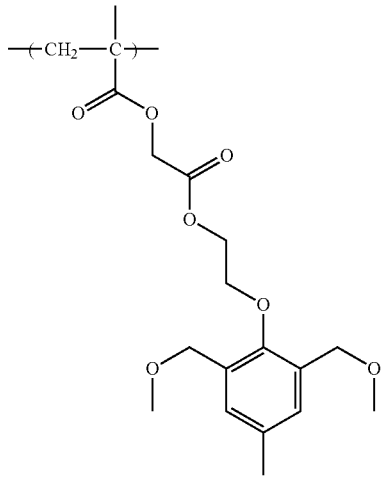
(Q-90) 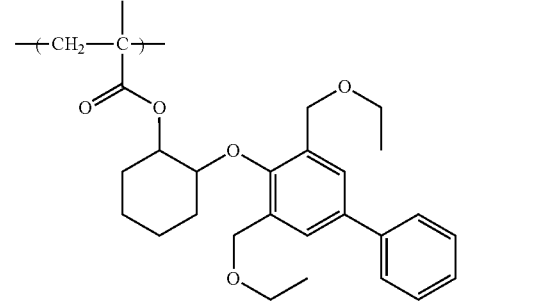
(Q-91) 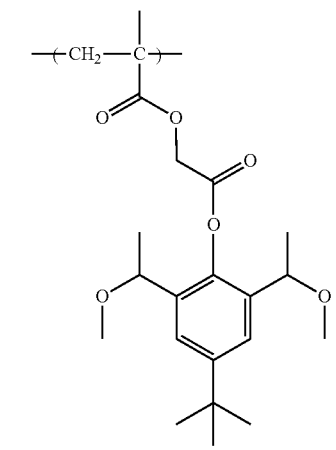
(Q-92) 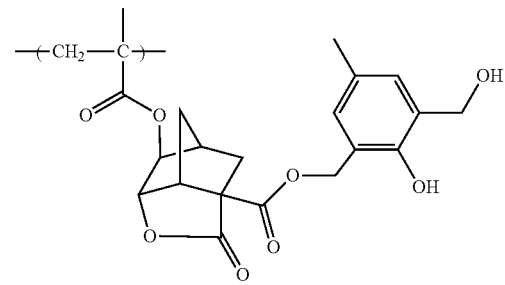

(Q-93)
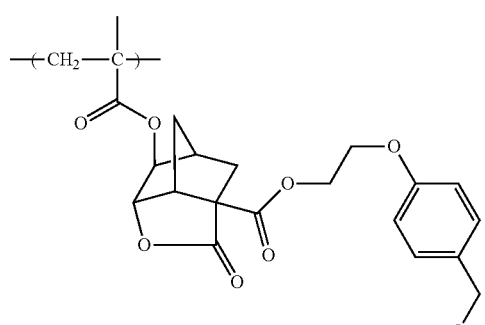
(Q-94)
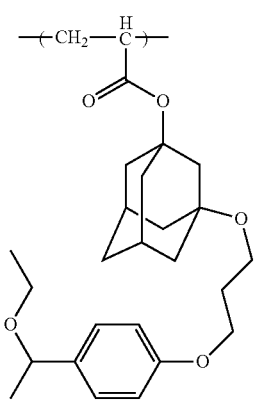
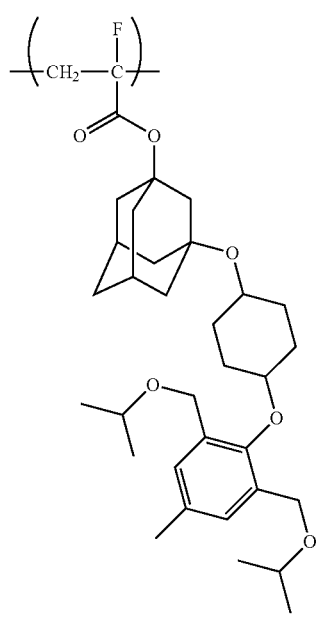
(Q-96)
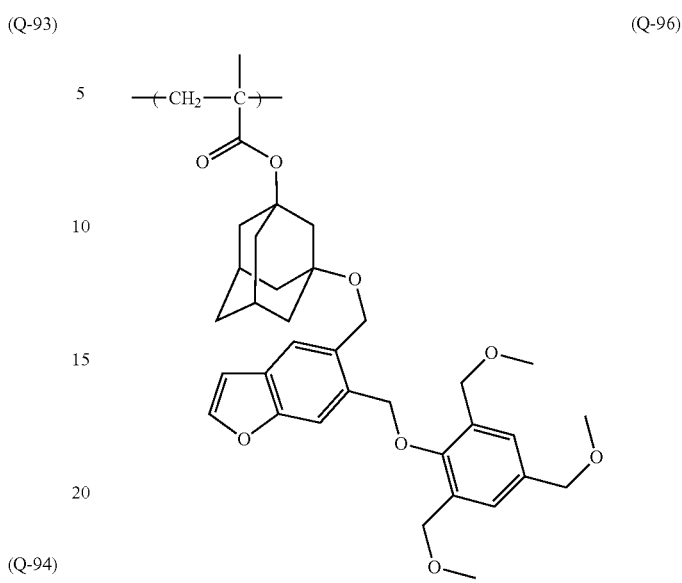
(Q-97)
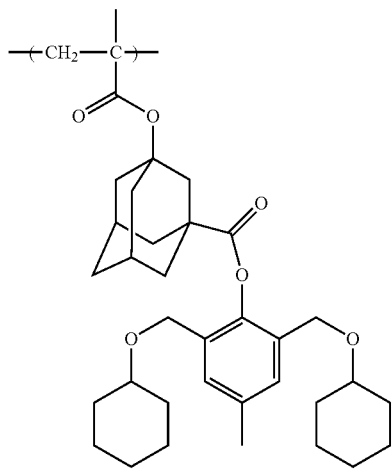
(Q-98)
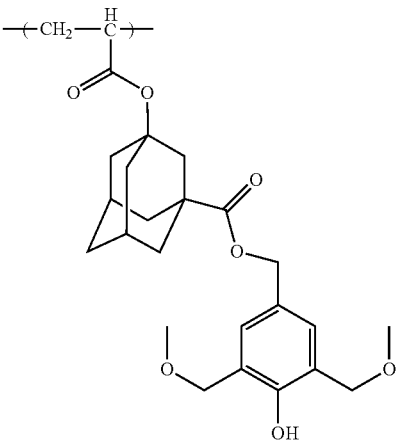

(Q-99) 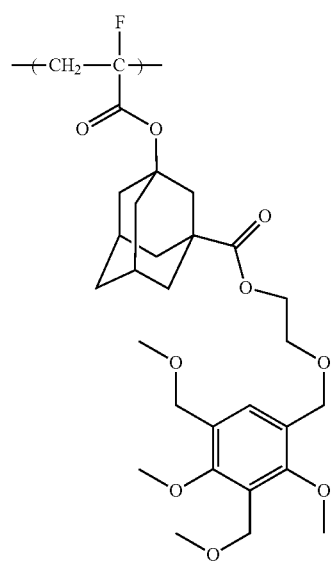
(Q-100) 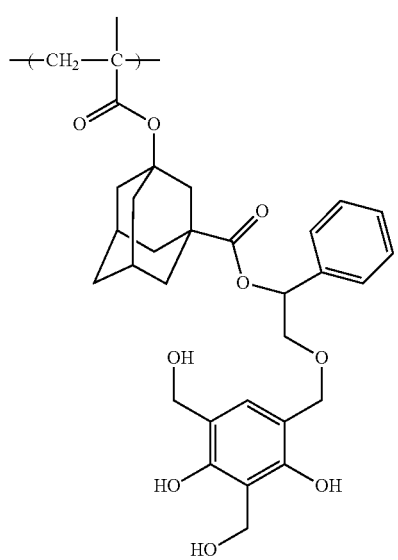
(Q-101) 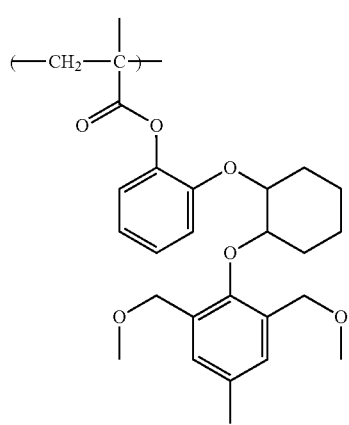
(Q-102) 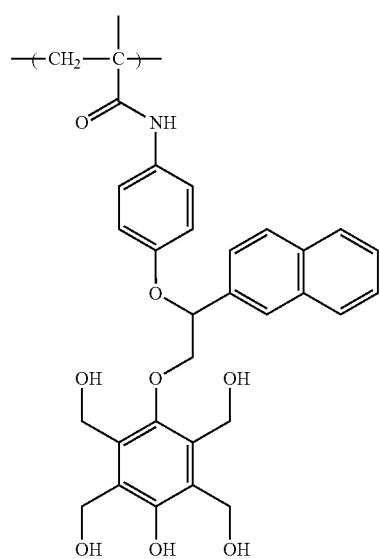
(Q-103) 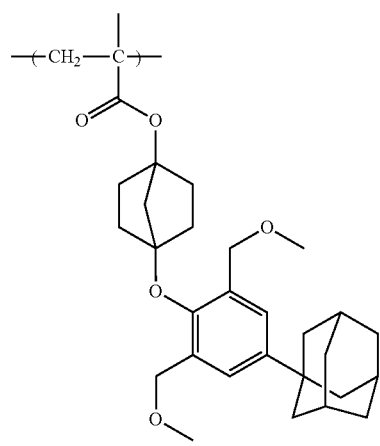
(Q-104) 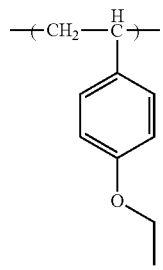

(Q-105)
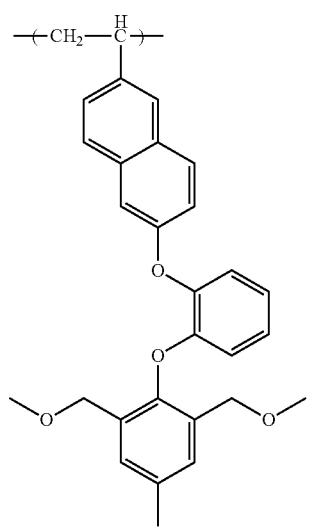
(A-106)
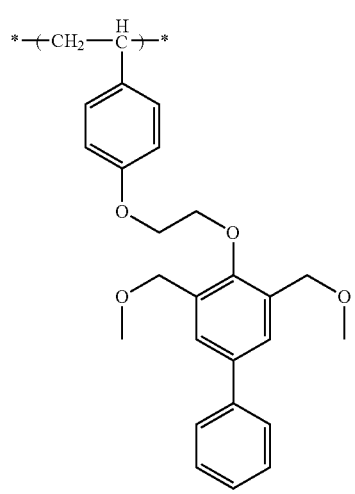
(A-107)
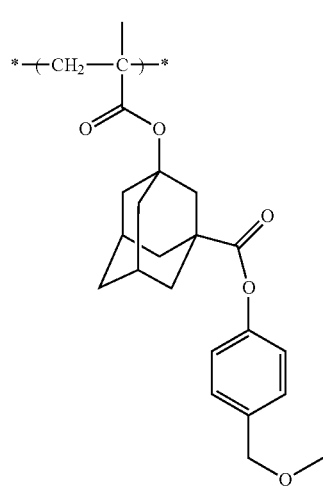
(A-108)
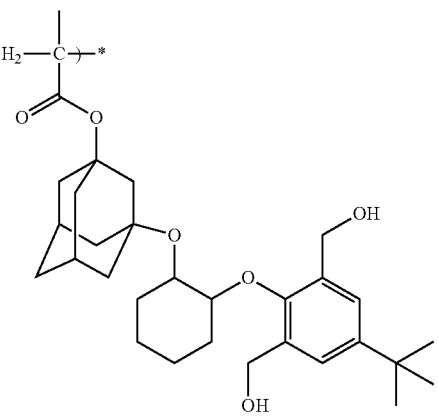
(A-109)
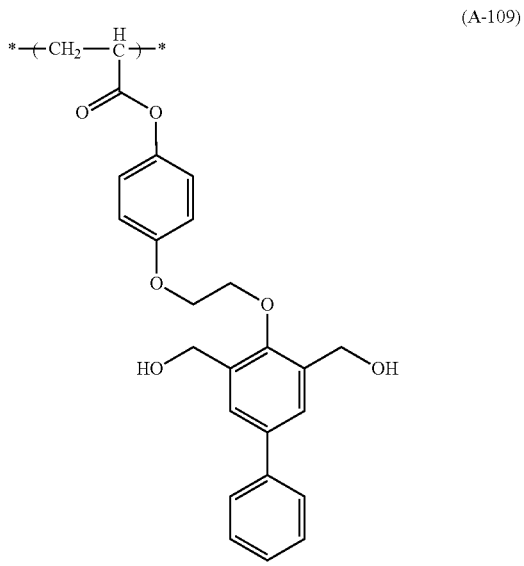
(A-110)
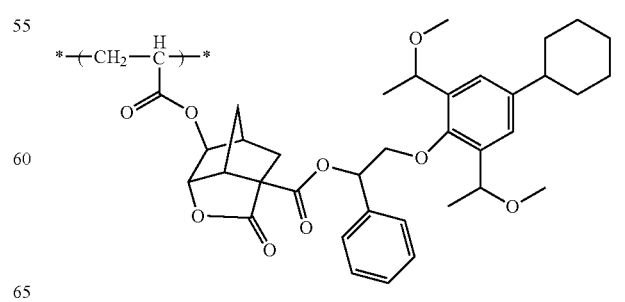

(A-111)

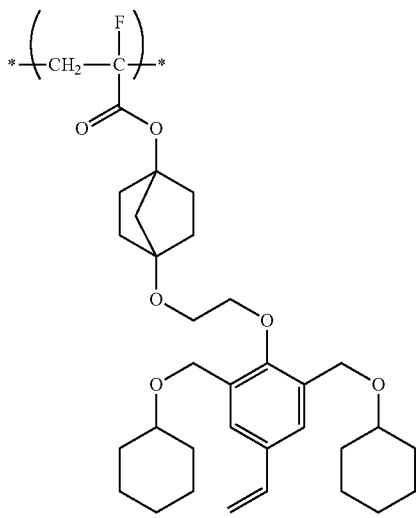

(b) Repeating Unit represented by General Formula (1-1) or (1-2)

Preferred examples of the above-mentioned repeating unit having a crosslinkable group may also include repeating units represented by the following General Formula (1-1) or (1-2).

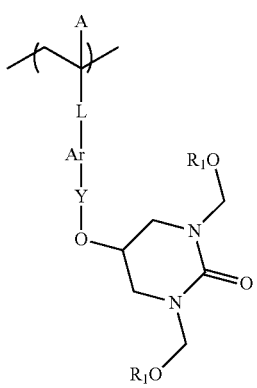
(1-1)

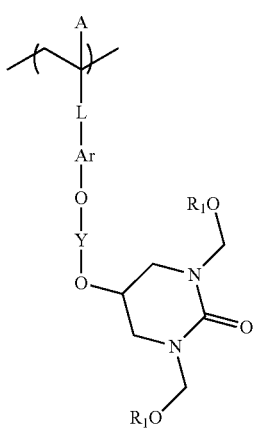
(1-2)

In General Formulae (1-1) and (1-2), A represents a hydrogen atom, a fluorine atom, a methyl group or a trifluoromethyl group. $R_1$ represents a hydrogen atom, or a liner, branched or cyclic monovalent hydrocarbon group having 1 to 6 carbon atoms. L represents a single bond or a divalent linking group. Ar represents a divalent aromatic ring group. Y represents a single bond or a divalent linking group.

A is preferably a hydrogen atom or a methyl group.

The divalent linking group represented by L may have a substituent, and specific examples of the divalent linking group represented by L and of the substituent which the divalent linking group may have are the same as those for L in General Formula (1).

L is preferably a single bond.

Specific examples and preferred examples of the aromatic ring represented by Ar are the same as the specific examples and preferred examples in the case where L in General Formula (1) is an aromatic ring.

Examples of the divalent linking group represented by Y may include a monocyclic or polycyclic aromatic ring having 6 to 18 carbon atoms, —C(=O)—, —O—C(=O)—, —CH$_2$—O—C(=O)—, a thiocarbonyl group, a linear or branched alkylene group (preferably having 1 to 10 carbon atoms, and more preferably 1 to 6 carbon atoms), a linear or branched alkenylene group (preferably having 2 to 10 carbon atoms, and more preferably 2 to 6 carbon atoms), a cycloalkylene group (preferably having 3 to 10 carbon atoms, and more preferably 3 to 6 carbon atoms), a sulfonyl group, —O—, —NH—, —S—, a cyclic lactone structure, or a divalent linking group of a combination thereof (preferably having 1 to 50 carbon atoms in total, more preferably 1 to 30 carbon atoms in total, and still more preferably 1 to 20 carbon atoms in total).

Y is preferably an ethylene group or a methylene carbonyl group.

Further, in General Formulae (1-1) and (1-2), $R_1$ represents a hydrogen atom, or a linear, branched or cyclic monovalent hydrocarbon group having 1 to 6 carbon atoms. Specific examples of the linear, branched or cyclic monovalent hydrocarbon group having 1 to 6 carbon atoms may preferably include alkyl groups such as a methyl group, an ethyl group, a propyl group, a butyl group, a pentyl group, a hexyl group, structural isomers thereof, a cyclopentyl group, and a cyclohexyl group. Particularly preferred is a methyl group. If the number of carbon atoms is higher than 6, crosslinkability may be lowered.

Preferred specific examples of the repeating unit represented by General Formulae (1-1) and (1-2) include the following repeating units, but are not limited thereto.

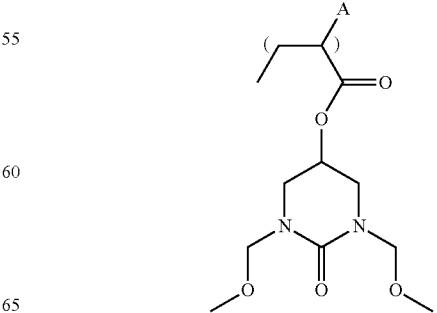

79
-continued
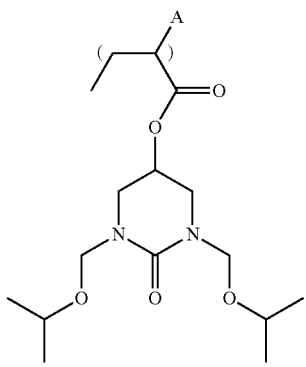
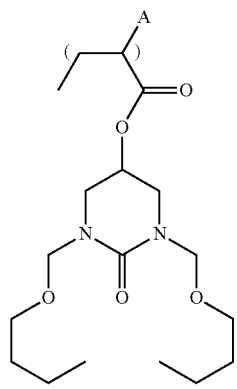
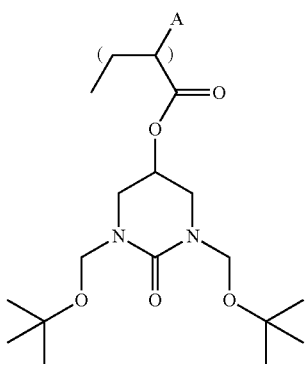
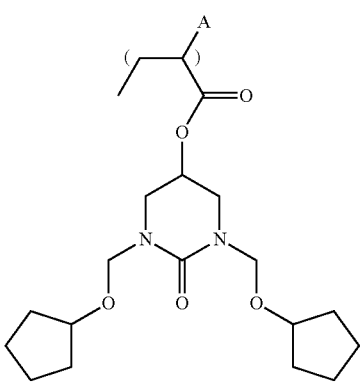
80
-continued
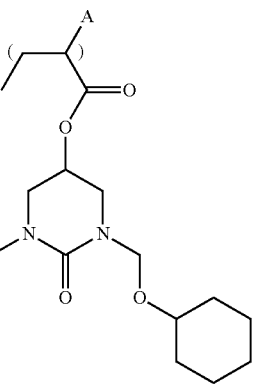
(In the formulae, A is as defined above.)
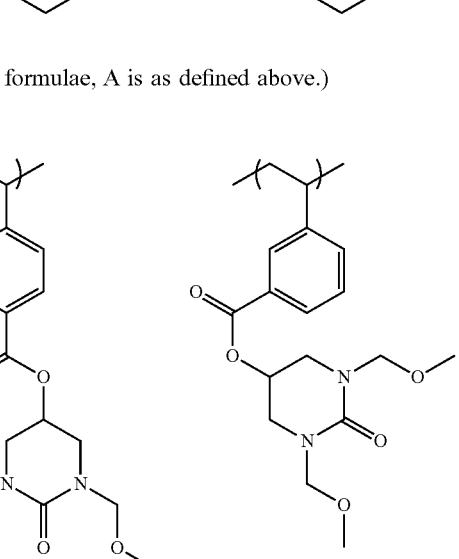
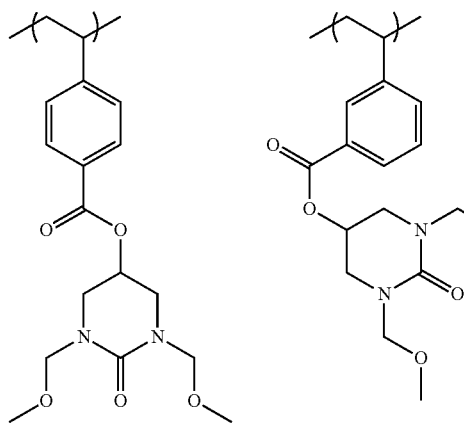
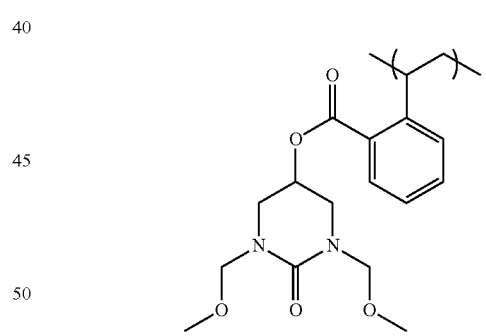
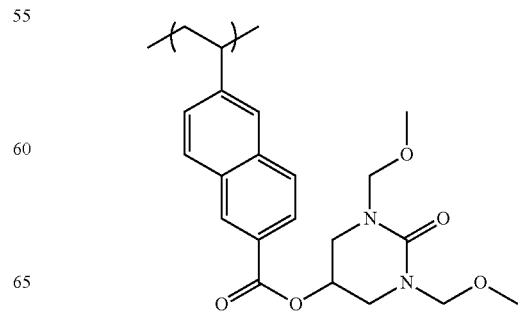

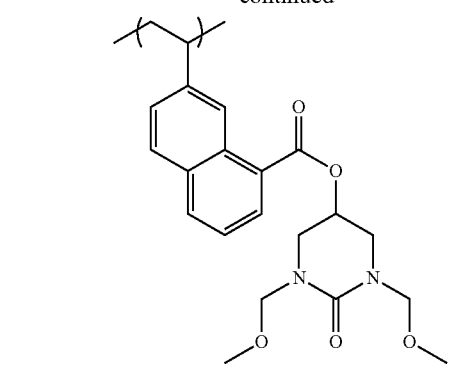
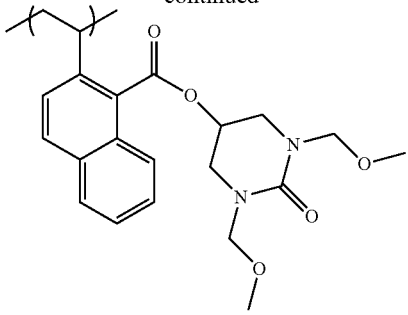
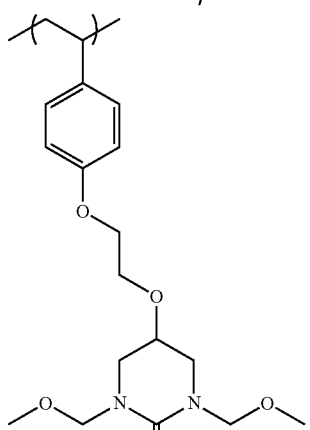
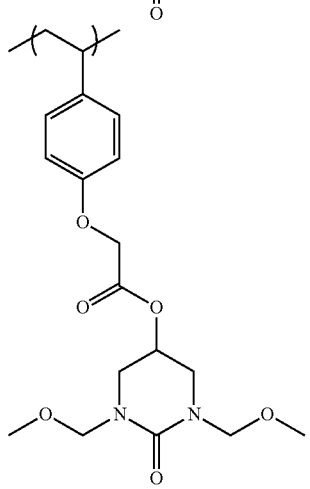

The resin (A) may or may not contain the repeating unit represented by General Formula (1-1) or (1-2) but in the case of containing them, the content of the repeating units is generally 1 mol % to 30 mol %, preferably 1 mol % to 20 mol %, more preferably 2 mol % to 10 mol %, and still more preferably 5 mol % to 10 mol %, based on total repeating units in the resin (A).

From the viewpoint of improving at least one of resolution, roughness characteristics, or EL (exposure latitude), the resin (A) preferably contains a repeating unit (A1) having a structural moiety capable of decomposing upon irradiation with actinic rays or radiation to generate an acid on the side chain (hereinafter referred to also as "acid-generating structure (a)").

It is also preferred that the resin (A) contains a repeating unit represented by the following General Formula (5), as the repeating unit (A1) having a structural moiety capable of decomposing upon irradiation with actinic rays or radiation to generate an acid on the side chain. Further, in the composition as one embodiment relating to the present invention, it is preferred that the acid-generating structure (a) of the resin (A) and the later-described compound (B) are the same component.

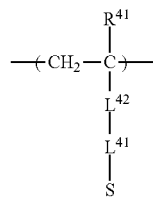

(5)

$R^{41}$ represents a hydrogen atom or a methyl group. $L^{41}$ represents a single bond or a divalent linking group. $L^{42}$ represents a divalent linking group. S represents a structural moiety capable of decomposing upon irradiation with actinic rays or radiation to generate an acid on the side chain.

$R^{41}$ is a hydrogen atom or a methyl group as described above and is preferably a hydrogen atom.

Examples of the divalent linking group of $L^{41}$ and $L^{42}$ may include an alkylene group, a cycloalkylene group, an arylene group, —O—, —$SO_2$—, —CO—, —N(R)—, —S—, —CS—, and a combination of two or more thereof, and a linking group having a total number of 20 or less carbon atoms is preferred. Here, R represents an aryl group, an alkyl group or cycloalkyl group.

The divalent linking group of $L^{42}$ is preferably an arylene group, and preferred examples of the group may include an arylene group having 6 to 18 carbon atoms (more preferably 6 to 10 carbon atoms) such as phenylene group, tolylene group and naphthylene group, and a divalent aromatic ring group containing a heterocyclic ring such as thiophene, furan, pyrrole, benzothiophene, benzofuran, benzopyrrole, triazine, imidazole, benzimidazole, triazole, thiadiazole, and thiazole.

The alkylene group of $L^{41}$ and $L^{42}$ is preferably an alkylene group having 1 to 12 carbon atoms, such as methylene group, ethylene group, propylene group, butylene group, hexylene group, octylene group, and dodecanylene group.

The cycloalkylene group of $L^{41}$ and $L^{42}$ is preferably a cycloalkylene group having 5 to 8 carbon atoms, such as cyclopentylene group and cyclohexylene group.

The arylene group of $L^{41}$ and $L^{42}$ is preferably an arylene group having 6 to 14 carbon atoms, such as phenylene group and naphthylene group.

These alkylene group, cycloalkylene group, and arylene group may further have a substituent. Examples of the substituent may include an alkyl group, a cycloalkyl group, an aryl group, an amino group, an amido group, a ureido group, a urethane group, a hydroxy group, a carboxy group, a halogen atom, an alkoxy group, a thioether group, an acyl group, an acyloxy group, an alkoxycarbonyl group, a cyano group, and a nitro group.

The acid-generating structure (a) preferably has a sulfonium salt structure or an iodonium salt structure (more preferably a sulfonium salt structure), and more preferably an ionic structural moiety containing a sulfonium salt or an iodonium salt (still more preferably an ionic structural moiety containing a sulfonium salt). More specifically, the acid-generating structure (a) is preferably a group represented by the following General Formula (PZI) or (PZII).

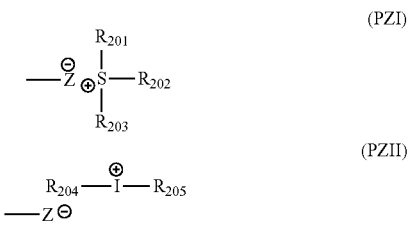

In General Formula (PZI),
each of $R_{201}$ to $R_{203}$ independently represents an organic group.

The number of carbon atoms in the organic group as $R_{201}$ to $R_{203}$ is generally 1 to 30, and preferably 1 to 20.

Two members of $R_{201}$ to $R_{203}$ may be bonded to form a ring structure, and the ring may contain an oxygen atom, a sulfur atom, an ester bond, an amido bond or a carbonyl group. Examples of the group formed by bonding of two members of $R_{201}$ to $R_{203}$ may include an alkylene group (for example, butylene group, pentylene group). When a repeating unit where two members of $R_{201}$ to $R_{203}$ are bonded to form a ring structure is used, it can be preferably expected that the exposure machine can be kept from contamination by a decomposition product during exposure.

$Z^-$ represents an acid anion generated resulting from decomposition upon irradiation with actinic rays or radiation and is preferably a non-nucleophilic anion. Examples of the non-nucleophilic anion may include sulfonate anion, carboxylate anion, sulfonylimide anion, bis(alkylsulfonyl)imide anion, and tris(alkylsulfonyl)methyl anion.

The non-nucleophilic anion is an anion having an extremely low ability of causing a nucleophilic reaction, and this anion can suppress the decomposition with aging due to the intramolecular nucleophilic reaction. Thanks to this anion, the aging stability of the resin and in turn, the aging stability of the composition are enhanced.

Examples of the organic group of $R_{201}$ to $R_{203}$ may include an aryl group, an alkyl group, a cycloalkyl group, a cycloalkenyl group, and an indolyl group. Here, in the cycloalkyl group and the cycloalkenyl group, at least one of carbon atoms forming the ring may be a carbonyl carbon.

At least one of $R_{201}$, $R_{202}$, or $R_{203}$ is preferably an aryl group, and it is more preferred that those three members are all an aryl group.

The aryl group in $R_{201}$, $R_{202}$, and $R_{203}$ is preferably a phenyl group or a naphthyl group, and more preferably a phenyl group.

The alkyl group, cycloalkyl group, and cycloalkenyl group of $R_{201}$, $R_{202}$ and $R_{203}$ are preferably a linear or branched alkyl group having 1 to 10 carbon atoms (for example, a methyl group, an ethyl group, a propyl group, a butyl group, a pentyl group), a cycloalkyl group having 3 to 10 carbon atoms (for example, a cyclopentyl group, a cyclohexyl group, a norbornyl group), and a cycloalkenyl group having 3 to 10 carbon atoms (for example, a pentadienyl group, a cyclohexenyl group).

The organic group as $R_{201}$, $R_{202}$, and $R_{203}$, such as aryl group, alkyl group, cycloalkyl group, cycloalkenyl group, and indolyl group, may further have a substituent. Examples of the substituent include, but are not limited to, a nitro group, a halogen atom such as a fluorine atom (preferably a fluorine atom), a carboxyl group, a hydroxyl group, an amino group, a cyano group, an alkyl group (preferably having 1 to 15 carbon atoms), an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms), an arylthio group (preferably having 6 to 14 carbon atoms), a hydroxyalkyl group (preferably having 1 to 15 carbon atoms), an alkylcarbonyl group (preferably having 2 to 15 carbon atoms), a cycloalkylcarbonyl group (preferably having 4 to 15 carbon atoms), an arylcarbonyl group (preferably having 7 to 14 carbon atoms), a cycloalkenyloxy group (preferably having 3 to 15 carbon atoms), and a cycloalkenylalkyl group (preferably having 4 to 20 carbon atoms).

In the cycloalkyl group and cycloalkenyl group as the substituent which may be substituted on each of the groups of $R_{201}$, $R_{202}$, and $R_{203}$, at least one of carbon atoms forming the ring may be a carbonyl carbon.

The substituent which may be substituted on each of the groups of $R_{201}$, $R_{202}$ and $R_{203}$ may further have a substituent, and examples of this further substituent are the same as examples of the substituent which may be substituted on each of the groups of $R_{201}$, $R_{202}$, and $R_{203}$, but an alkyl group and a cycloalkyl group are preferred.

The preferred structure in the case where at least one of $R_{201}$, $R_{202}$, or $R_{203}$ is not an aryl group includes cation structures such as compounds illustrated in paragraphs "0046" and "0047" of JP2004-233661A, compounds illustrated in paragraphs "0040" to "0046" of JP2003-35948A, Compounds (I-1) to (I-70) illustrated in US2003/0224288A, and Compounds (IA-1) to (IA-54) and (IB-1) to (IB-24) illustrated in US2003/0077540A.

In General Formula (PZII), each of $R_{204}$ and $R_{205}$ independently represents an aryl group, an alkyl group, or a cycloalkyl group. These aryl, alkyl, and cycloalkyl groups are the same as the aryl, alkyl, and cycloalkyl groups of $R_{201}$ to $R_{203}$ in the compound (PZI).

The aryl group of $R_{204}$ and $R_{205}$ may be an aryl group having a heterocyclic structure containing an oxygen atom, a nitrogen atom, or a sulfur atom. Examples of the aryl group having a heterocyclic structure include a pyrrole residue (a group formed by removing one hydrogen atom from a pyrrole), a furan residue (a group formed by removing one hydrogen atom from a furan), a thiophene residue (a group formed by removing one hydrogen atom from a thiophene), an indole residue (a group formed by removing one hydrogen atom from an indole), a benzofuran residue (a group formed by removing one hydrogen atom from a benzofuran), and a benzothiophene residue (a group formed by removing one hydrogen atom from a benzothiophene).

The aryl group, alkyl group, and cycloalkyl group of $R_{204}$ and $R_{205}$ may have a substituent. Examples of the substituent include those of the substituent which the aryl group, alkyl group, and cycloalkyl group of $R_{201}$ to $R_{203}$ in the compound (PZI) may have.

$Z^-$ represents an acid anion generated resulting from decomposition upon irradiation with actinic rays or radiation and is preferably a non-nucleophilic anion, and examples thereof are the same as those for $Z^-$ in General Formula (PZI).

Preferred specific examples of the acid-generating structure (a) include the specific examples described in paragraphs "0145" to "0148" of JP2013-80002A.

The acid-generating structure (a) is more preferably a group represented by the following General Formula (6).

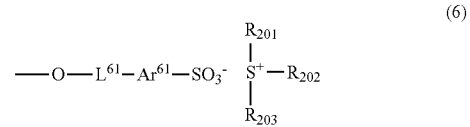

In the formula, $L^{61}$ represents a divalent linking group, and $Ar^{61}$ represents an arylene group. $R_{201}$, $R_{202}$, and $R_{203}$ have the same definitions as $R_{201}$, $R_{202}$, and $R_{203}$ in General Formula (PZI), respectively.

Examples of the divalent linking group of $L^{61}$ include an alkylene group, a cycloalkylene group, —O—, —SO$_2$—, —CO—, —N(R)—, —S—, —CS—, and a combination thereof. Here, R represents an aryl group, an alkyl group, or cycloalkyl group. The total number of carbon atoms in the divalent linking group of $L^{61}$ is preferably 1 to 15, and more preferably 1 to 10.

The alkylene group of $L^{61}$ is preferably an alkylene group having 1 to 12 carbon atoms, such as a methylene group, an ethylene group, a propylene group, a butylene group, a hexylene group, an octylene group, and a dodecanylene group.

The cycloalkylene group of $L^{61}$ is preferably a cycloalkylene group having 5 to 8 carbon atoms, such as a cyclopentylene group and a cyclohexylene group.

The group as $L^{61}$ is preferably a carbonyl group, a methylene group, *—CO—(CH$_2$)$_n$—O—, *—CO—(CH$_2$)$_n$—O—CO—, *—(CH$_2$)$_n$—COO—, *—(CH$_2$)$_n$—CONR—, or *—CO—(CH$_2$)$_n$—NR—, and particularly preferably a carbonyl group, *—CH$_2$—COO—, *—CO—CH$_2$—O—, *—CO—CH$_2$—O—CO—, *—CH$_2$—CONR—, or *—CO—CH$_2$—NR—. Here, n represents an integer of 1 to 10, n is preferably an integer of 1 to 6, more preferably an integer of 1 to 3, and most preferably 1. Also, * indicates a connecting site on the main chain side, that is, a connecting site to the O atom in the formulae.

$Ar^{61}$ represents an arylene group and may have a substituent. The substituent which $Ar^{61}$ may have is an alkyl group (preferably having 1 to 8 carbon atoms, and more preferably 1 to 4 carbon atoms), an alkoxy group (preferably having 1 to 8 carbon atoms, and more preferably 1 to 4 carbon atoms), or a halogen atom (preferably a fluorine atom, a chlorine atom, a bromine atom, or an iodine atom, and more preferably a fluorine atom). The aromatic ring of $Ar^{61}$ may be an aromatic hydrocarbon ring (for example, a benzene ring or a naphthalene ring) or an aromatic heterocyclic ring (for example, a quinoline ring), and preferably has 6 to 18 carbon atoms and more preferably 6 to 12 carbon atoms.

$Ar^{61}$ is preferably an unsubstituted arylene group or an arylene group substituted with an alkyl group or a fluorine atom, and more preferably a phenylene group or a naphthylene group.

Specific examples and preferred examples of $R_{201}$, $R_{202}$, and $R_{203}$ are the same as those described for $R_{201}$, $R_{202}$, and $R_{203}$ in General Formula (PZI).

The synthesis method of the monomer corresponding to the repeating unit (A1) having a structural moiety capable of decomposing upon irradiation with actinic rays or radiation to generate an acid on the side chain is not particularly limited, but, for example, in the case of an onium structure, includes a method of synthesizing the monomer by exchanging an acid anion having a polymerizable unsaturated bond corresponding to the repeating unit with a halide of a known onium salt.

More specifically, a metal ion salt (for example, sodium ion or potassium ion) or ammonium salt (such as ammonium or triethylammonium salt) of an acid having a polymerizable unsaturated bond corresponding to the repeating unit and an onium salt having a halogen ion (such as chloride ion, bromide ion, or iodide ion) are stirred in the presence of water or methanol to perform an anion exchange reaction, and the reaction product is subjected to separation and washing operations with an organic solvent such as dichloromethane, chloroform, ethyl acetate, methyl isobutyl ketone, and tetrahydroxyfuran, and water, whereby the desired monomer corresponding to the repeating unit represented by General Formula (5) can be synthesized.

The monomer can also be synthesized by stirring the compounds above in the presence of an organic solvent separable from water, such as dichloromethane, chloroform, ethyl acetate, methyl isobutyl ketone, and tetrahydroxyfuran, and water to perform an anion exchange reaction, and then subjecting the reaction product to separation and washing operations with water.

Furthermore, the repeating unit (A1) having a structural moiety capable of decomposing upon irradiation with actinic rays or radiation to generate an acid on the side chain can also be synthesized by introducing an acid anion moiety into the side chain by a polymer reaction and introducing an onium salt through salt exchange.

Specific examples of the repeating unit (A1) having a structural moiety capable of decomposing upon irradiation with actinic rays or radiation to generate an acid on the side chain include specific examples described in paragraphs "0168" to "0210" of JP2013-80002A.

The content of the repeating unit (A1) having a structural moiety capable of decomposing upon irradiation with actinic rays or radiation to generate an acid on the side chain in the resin (A) is preferably 1 mol % to 40 mol %, more preferably 2 mol % to 30 mol %, and particularly preferably 4 mol % to 25 mol %, based on total repeating units in the resin (A).

Preferably, the resin (A) used in the present invention further has the following repeating unit (hereinafter, also referred to as "other repeating unit") as a repeating unit other than the above described repeating unit.

Examples of a polymerizable monomer for forming these other repeating units may include styrene, alkyl-substituted styrene, alkoxy-substituted styrene, halogen-substituted styrene, O-alkylated styrene, O-acylated styrene, hydrogenated hydroxystyrene, a maleic anhydride, an acrylic acid derivative (for example, acrylic acid or acrylic acid ester), a methacrylic acid derivative (for example, methacrylic acid or methacrylic acid ester), N-substituted maleimide, acrylonitrile, methacrylonitrile, vinyl naphthalene, vinyl anthracene, and indene which may have a substituent.

The resin (A) may or may not have these other repeating units. In the case where the resin (A) has these other repeating units, the content of these other repeating units in the resin (A) is generally 1 mol % to 30 mol %, preferably 1 mol % to 20 mol %, more preferably 2 mol % to 10 mol %, and still more preferably 5 mol % to 10 mol %, based on the total repeating units constituting the resin (A).

The resin (A) may be synthesized by a known method such as a radical polymerization method, an anionic polymerization method, or a living radical polymerization method (for example, an iniferter method). For example, in the anionic polymerization method, vinyl monomers are dissolved in an appropriate organic solvent, and reacted usually under a cooling condition by using a metal compound (for example, butyllithium) as an initiator, whereby the polymer can be obtained.

As the resin (A), a polyphenol compound produced by a condensation reaction of an aromatic ketone or aromatic aldehyde and a compound containing 1 to 3 phenolic hydroxyl groups (see, for example, JP2008-145539A), a calixarene derivative (see, for example, JP2004-18421A), a Noria derivative (see, for example, JP2009-222920A), and a polyphenol derivative (see, for example, JP2008-94782A) can also be applied, and these may be modified by a polymer reaction to synthesize the resin.

The resin (A) is preferably synthesized by modifying a polymer synthesized by a radical polymerization or anionic polymerization method, through a polymer reaction.

The weight average molecular weight of the resin (A) is preferably 1,000 to 200,000, more preferably 2,000 to 50,000, and still more preferably 2.000 to 15,000.

The polydispersity (molecular weight distribution) (Mw/Mn) of the resin (A) is preferably 2.0 or less, and from the viewpoint of enhancing the sensitivity and resolution, the polydispersity thereof is preferably 1.0 to 1.80, more preferably 1.0 to 1.60, and most preferably 1.0 to 1.20. The use of living polymerization such as living anionic polymerization is preferred because the obtained polymer compound may have a uniform polydispersity (molecular weight distribution). The weight average molecular weight (Mw), number average molecular weight (Mn), and polydispersity (Mw/Mn) of the resin are defined as values in terms of polystyrene by GPC (solvent: tetrahydrofuran, column: TSK gel Multipore HXL-M manufactured by Tosoh Corporation, column temperature: 40° C., flow velocity: 1.0 mL/min, detector: RI) measurement.

The content of the resin (A) in the composition of the present invention is preferably 30 mass % to 95 mass %, more preferably 40 mass % to 90 mass %, and particularly preferably 50 mass % to 85 mass %, based on the total solid content of the composition.

Specific examples of the resin (A) will be shown below, but the present invention is not limited thereto.

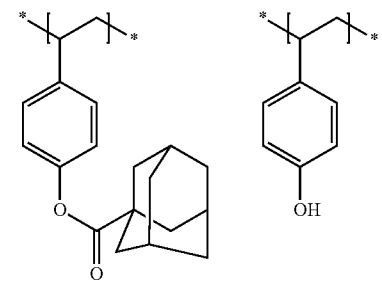

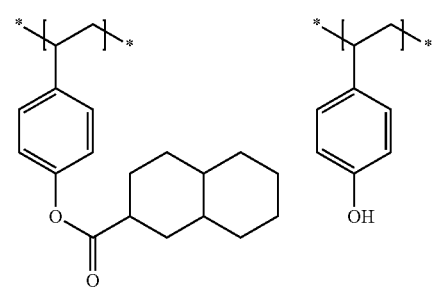

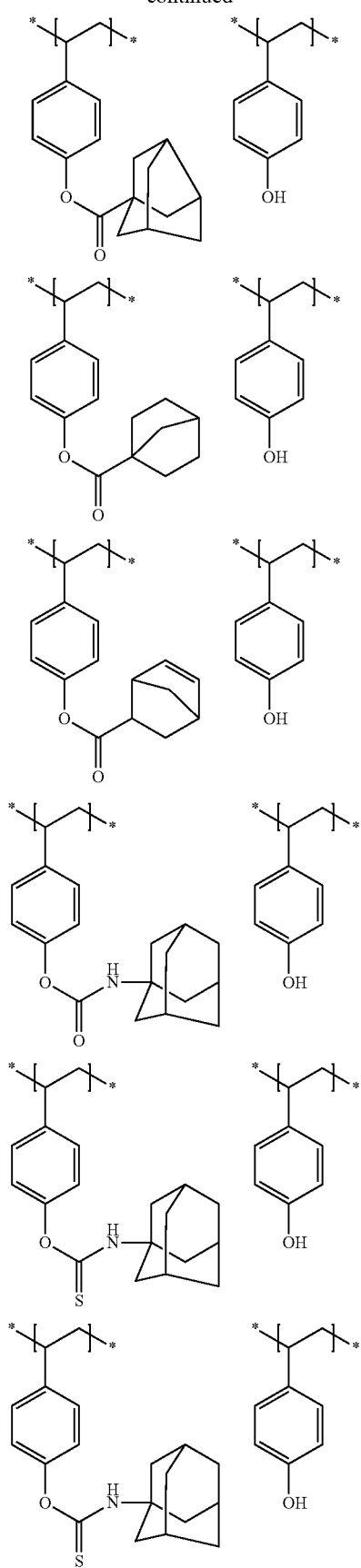
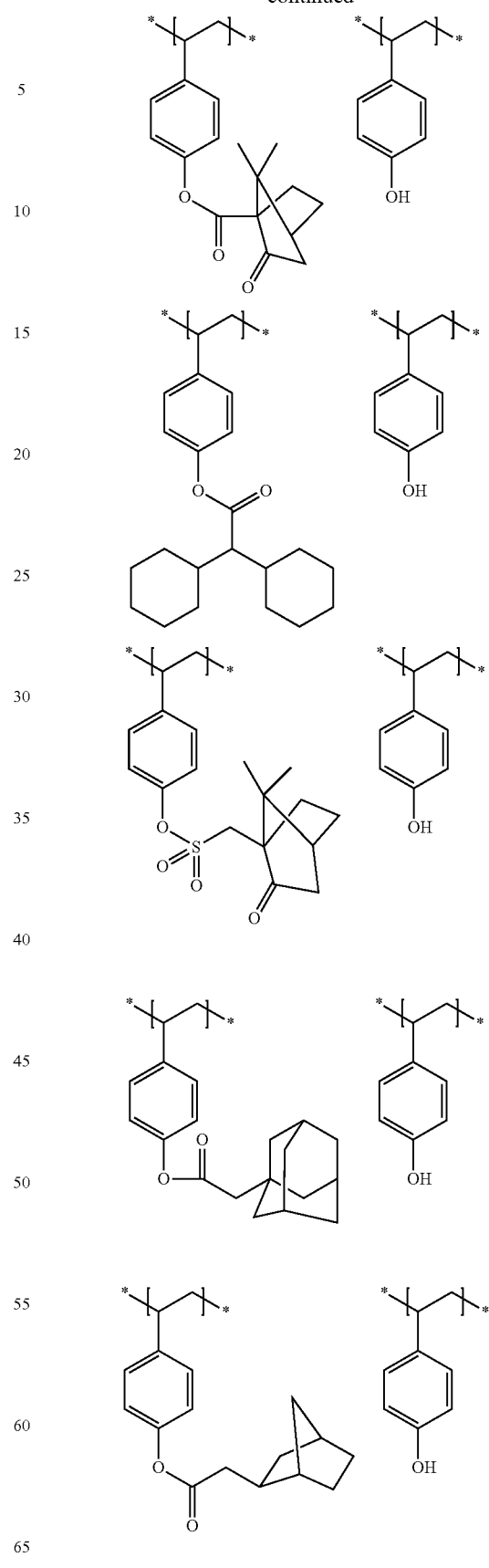

-continued
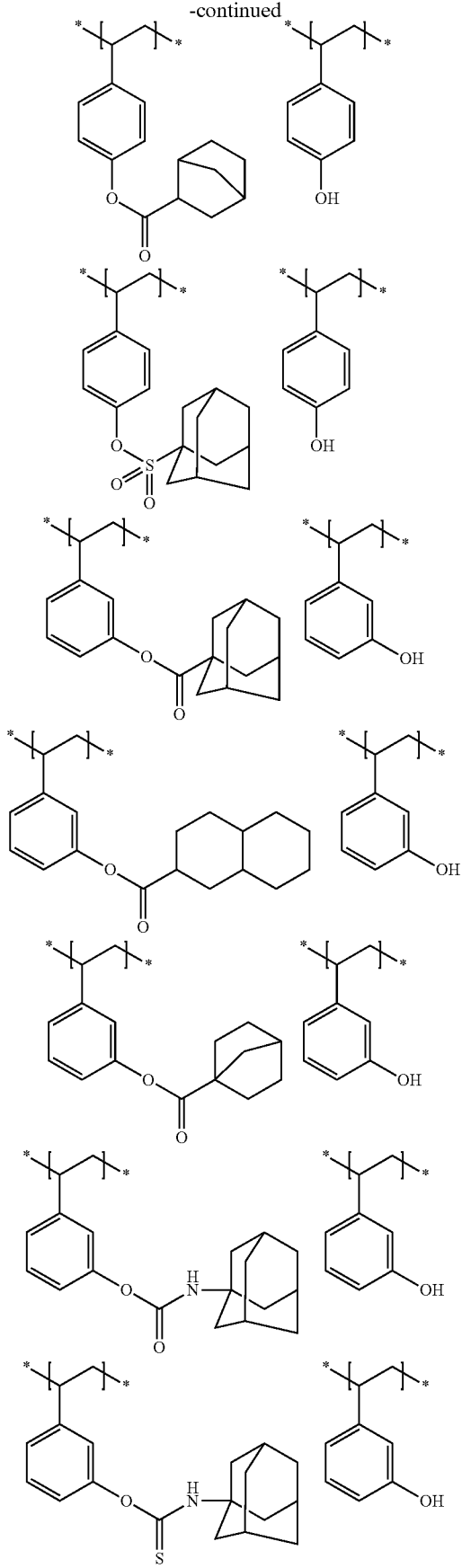
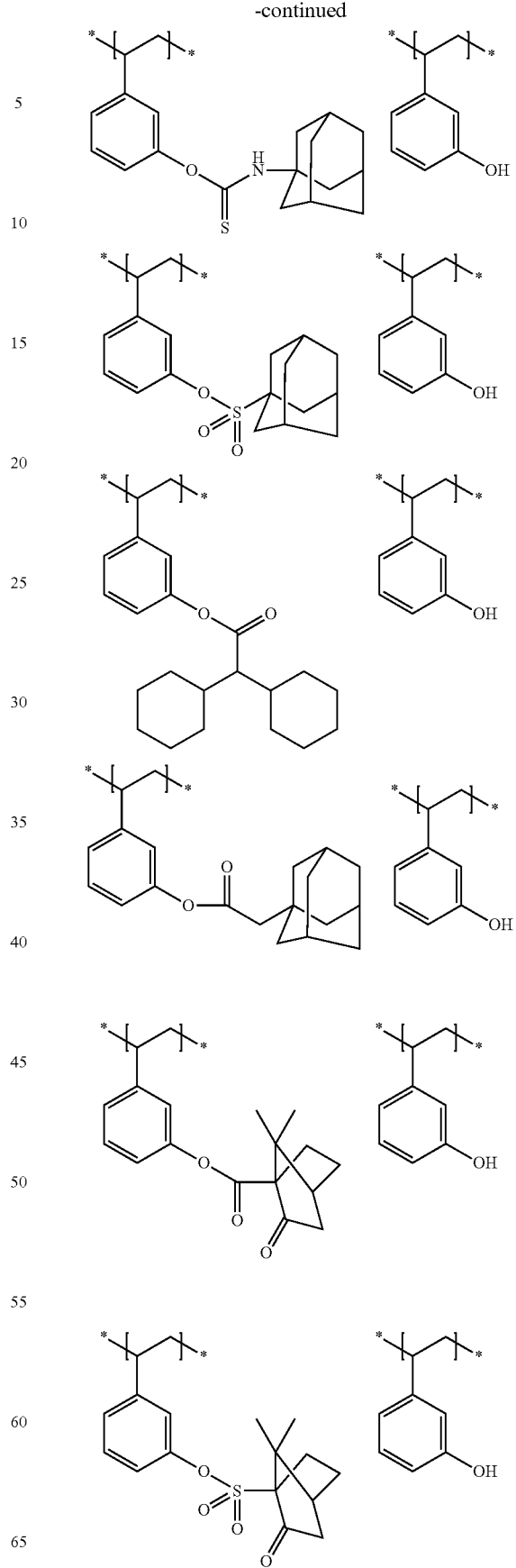

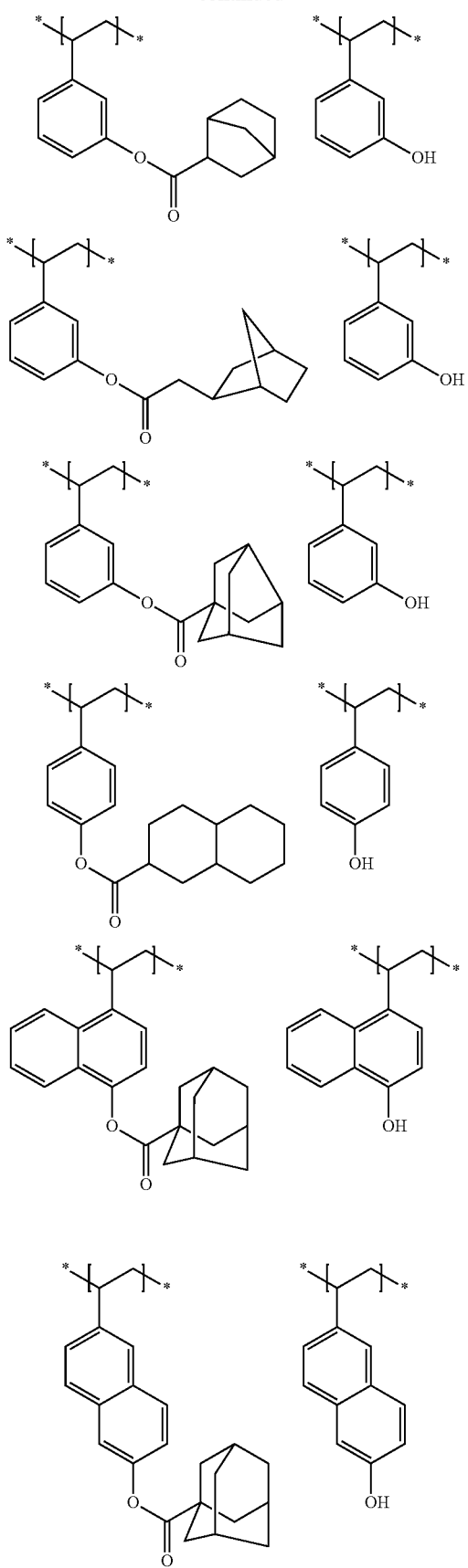
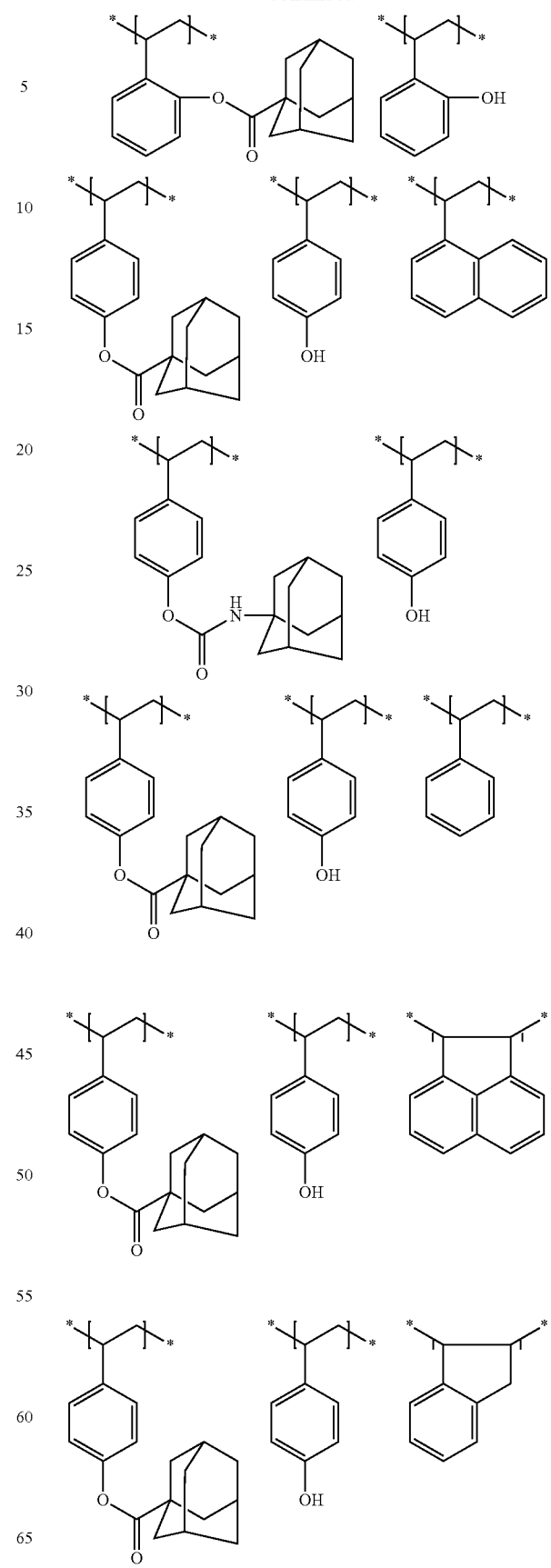

-continued
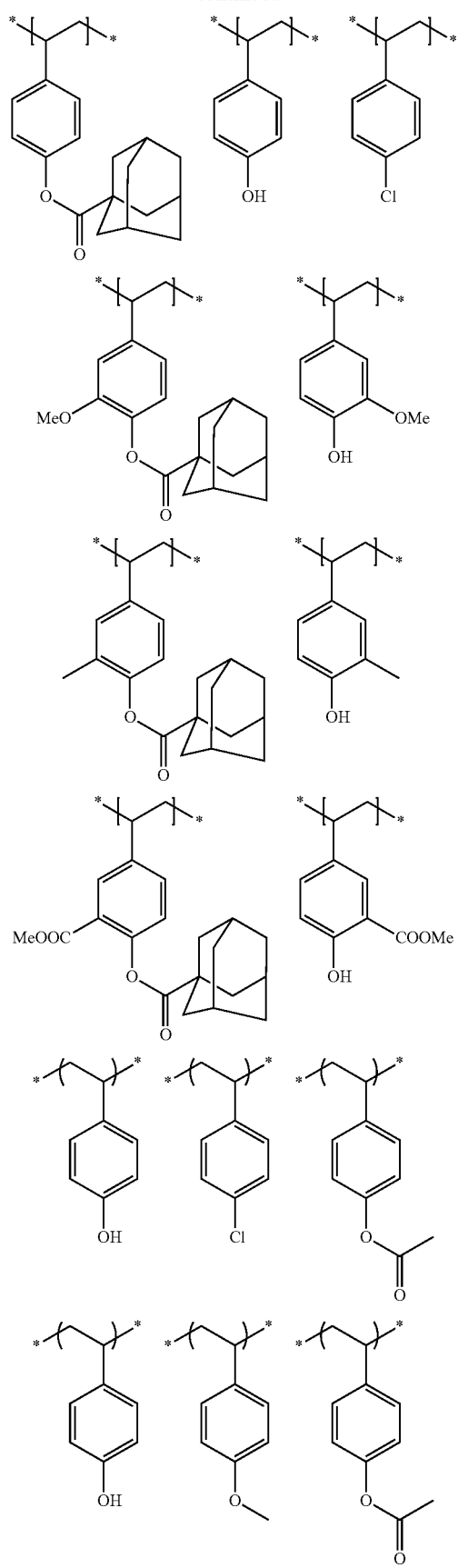
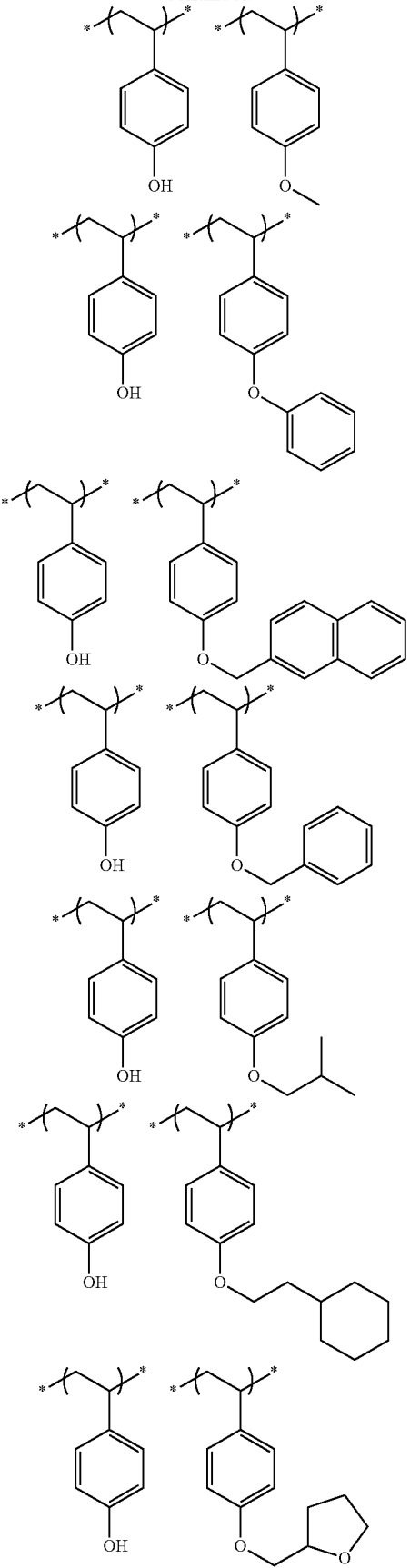

97
-continued
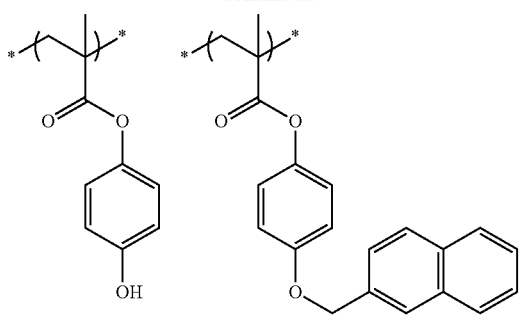
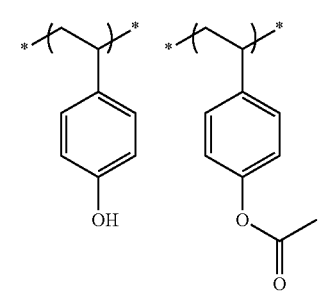
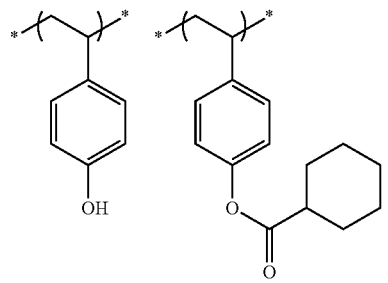
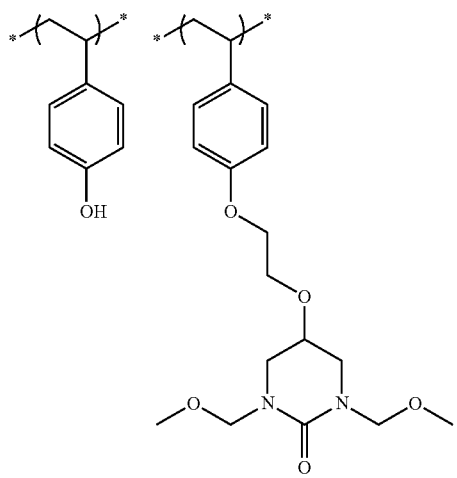
98
-continued
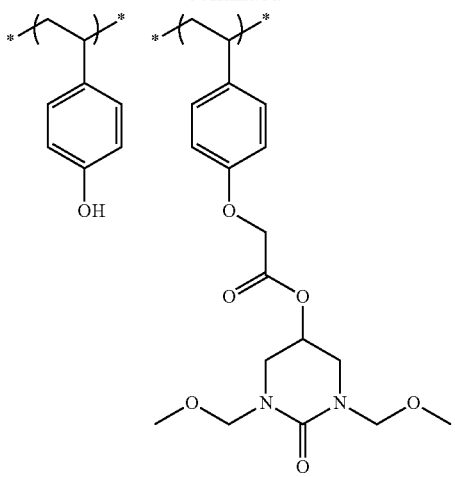
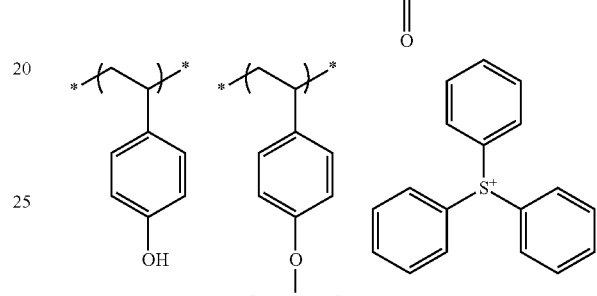
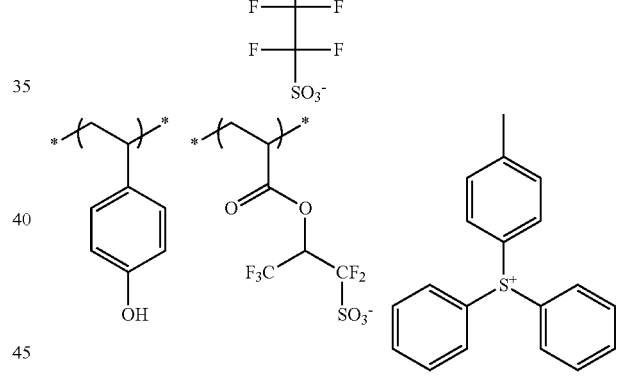
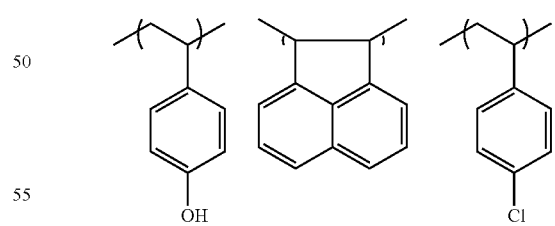
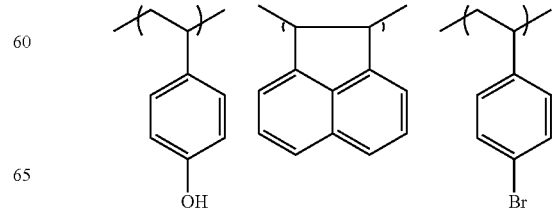

99
-continued
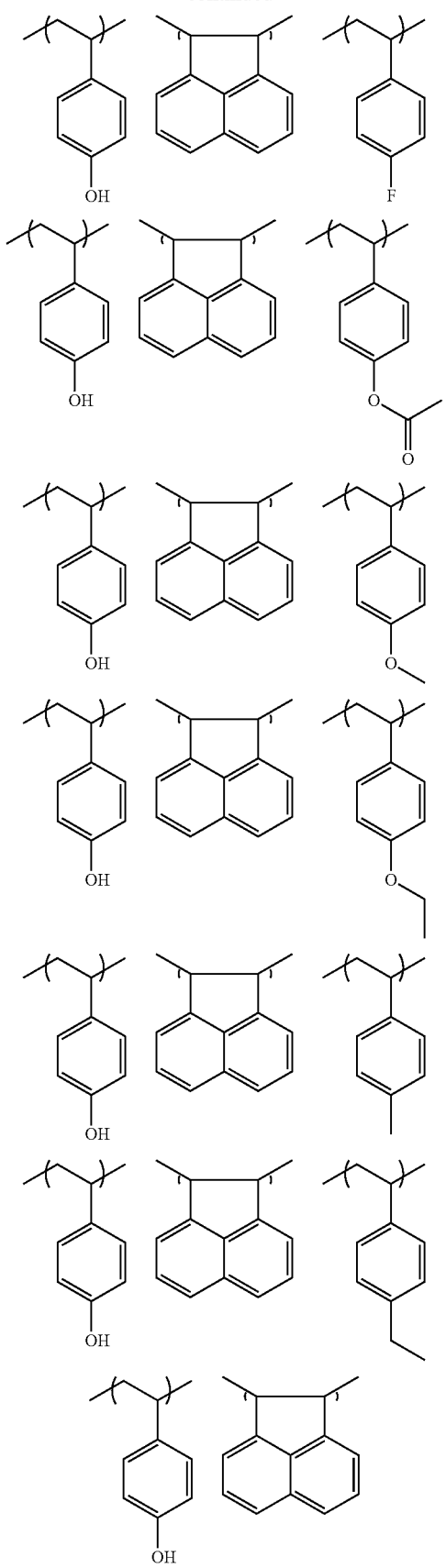
100
-continued
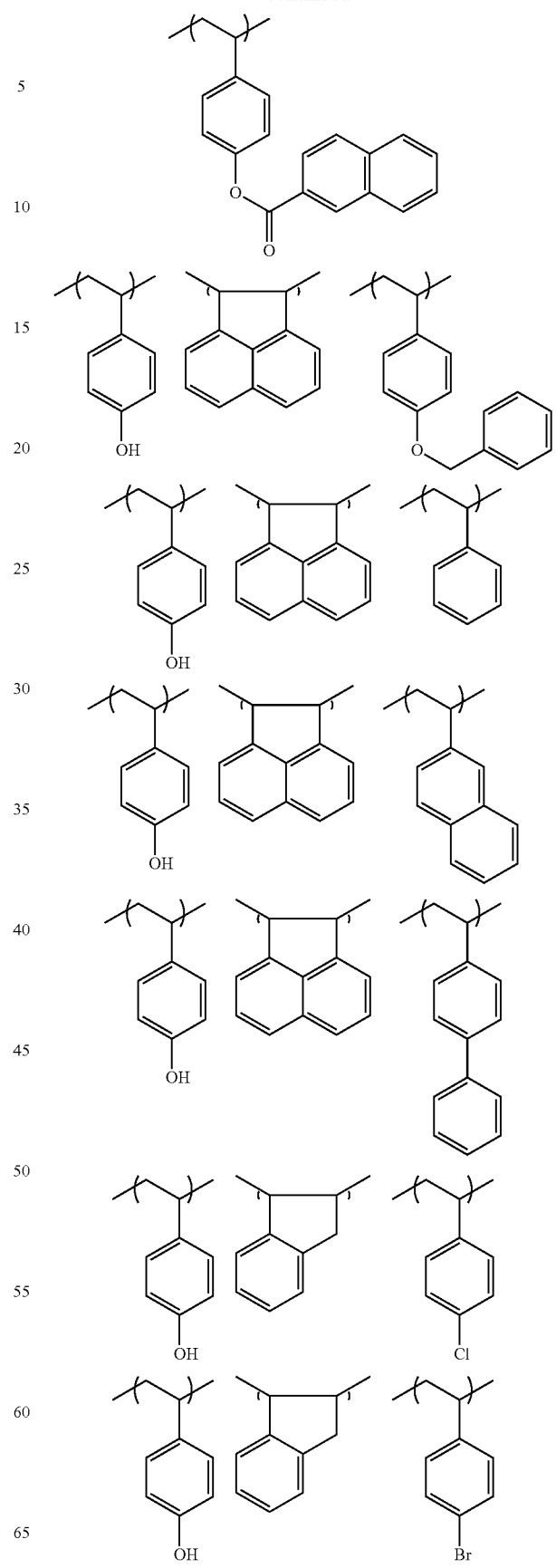

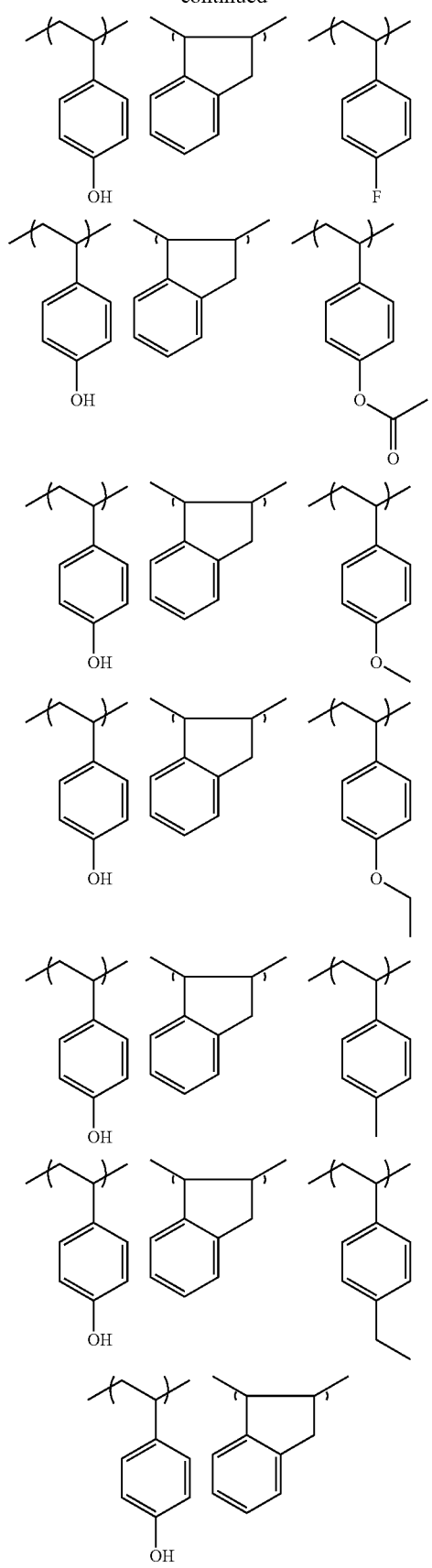
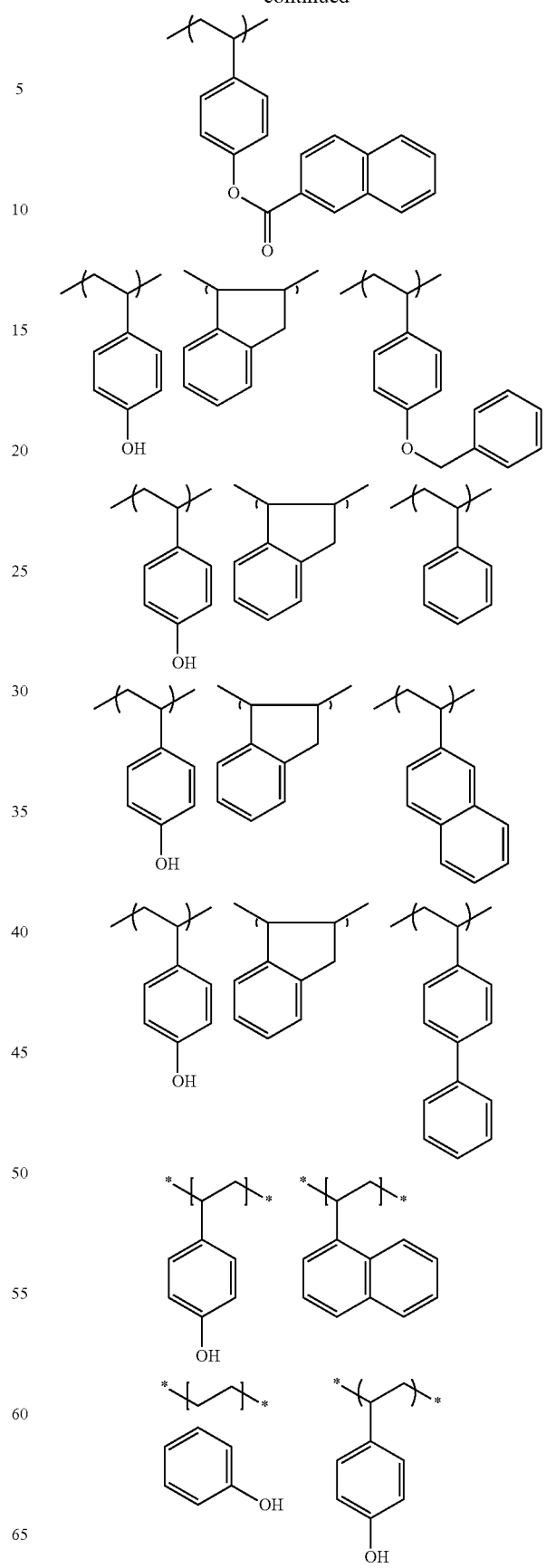

-continued

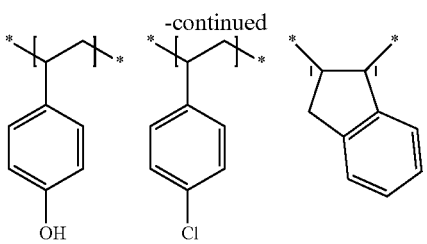

<Compound Capable of Generating Acid Upon Irradiation with Actinic Rays or Radiation>

The composition of the present invention may contain a compound capable of generating an acid upon irradiation with actinic rays or radiation (hereinafter, simply referred to as an "acid generator" or "compound (B)").

A preferred embodiment of the acid generator is an onium compound. Examples of the onium compound include a sulfonium salt, an iodonium salt, and a phosphonium salt.

Another preferred embodiment of the acid generator is a compound capable of generating a sulfonic acid, an imide acid, or a methide acid upon irradiation with actinic rays or radiation. Examples of the acid generator in this embodiment include a sulfonium salt, an iodonium salt, a phosphonium salt, oxime sulfonate, and imidosulfonate.

The acid generator for use in the present invention is not limited to a low molecular weight compound, and a compound where a group capable of generating an acid upon irradiation with actinic rays or radiation is introduced into the main or side chain of a polymer compound may also be used. Furthermore, in the case where, as described above, a group capable of generating an acid upon irradiation with actinic rays or radiation is present in a repeating unit serving as a copolymerization component of the alkali-soluble resin (A) for use in the present invention, the acid generator (B) as a molecule different from the alkali-soluble resin (A) of the present invention may not be contained in the composition.

The acid generator is preferably a compound capable of generating an acid upon irradiation with an electron beam or extreme ultraviolet rays.

In the present invention, the onium compound is preferably a sulfonium compound represented by the following General Formula (7) or an iodonium compound represented by General Formula (8).

In General Formulae (7) and (8), each of $R_{a1}$, $R_{a2}$, $R_{a3}$, $R_{a4}$, and $R_{a5}$ independently represents an organic group.

$X^-$ represents an organic anion.

Hereinafter, the sulfonium compound represented by General Formula (7) and the iodonium compound represented by General Formula (8) will be described in more detail.

Each of $R_{a1}$ to $R_{a3}$ in General Formula (7) and $R_{a4}$ and $R_{a5}$ in General Formula (8) independently represents an organic group, but each of at least one of $R_{a1}$, $R_{a2}$, or $R_{a3}$ and at least one of $R_{a4}$ or $R_{a5}$ is preferably an aryl group. The aryl group is preferably a phenyl group or a naphthyl group, and more preferably a phenyl group.

Examples of the organic anion of $X^-$ in General Formulae (7) and (8) include a sulfonate anion, a carboxylate anion, a bis(alkylsulfonyl)amide anion, and a tris(alkylsulfonyl)methide anion. The organic anion is preferably an organic anion represented by the following General Formula (9), (10), or (11), and more preferably an organic anion represented by the following General Formula (9).

In General Formulae (9), (10), and (11), each of $Rc_1$, $Rc_2$, $Rc_3$, and $Rc_4$ represents an organic group.

The organic anion of $X^-$ corresponds to a sulfonic acid, an imide acid, or a methide acid which is an acid generated upon irradiation with actinic rays or radiation such as an electron beam and extreme ultraviolet rays.

Examples of the organic group of $Rc_1$ to $Rc_4$ include an alkyl group, a cycloalkyl group, an aryl group, and a group formed by combining a plurality of such groups. Among these organic groups, more preferred are an alkyl group substituted with a fluorine atom or a fluoroalkyl group at the 1-position, a cycloalkyl group substituted with a fluorine atom or a fluoroalkyl group, and a phenyl group substituted with a fluorine atom or a fluoroalkyl group. A plurality of organic groups of $Rc_2$ to $Rc_4$ may be linked together to form a ring, and as for the group having a plurality of linked organic groups, an alkylene group substituted with a fluorine atom or a fluoroalkyl group is preferred. By containing the fluorine atom or the fluoroalkyl group, the acidity of the acid generated by light irradiation is increased, thereby improving the sensitivity. Meanwhile, it is preferred that a terminal group does not contain a fluorine atom as a substituent.

Further, in one embodiment of the present invention, the acid generator is preferably a compound capable of generating an acid represented by the following General Formula (IIIB) or (IVB) upon irradiation with actinic rays or radiation. Since the acid generator is a compound capable of generating an acid represented by the following General Formula (IIIB) or (IVB), which contains a cyclic organic group, it is possible to achieve superior resolution and roughness performance. In addition, improving effects of the PEB temperature dependency can be further enhanced by the synergistic effect with the crosslinking agent (C).

The organic anion of $X^-$ can be an anion capable of generating an organic acid represented by the following General Formula (IIIB) or (IVB).

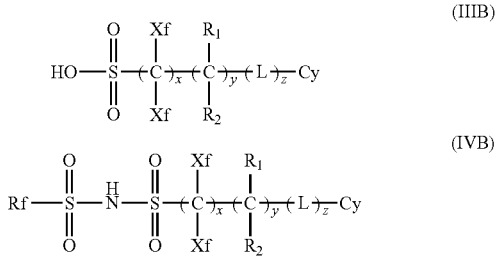

In the general formulae,
each Xf independently represents a fluorine atom or an alkyl group substituted with at least one fluorine atom.
Each of $R_1$ and $R_2$ independently represents a hydrogen atom or an alkyl group.
Each L independently represents a divalent linking group.
Cy represents a cyclic organic group.
Rf represents a fluorine atom-containing group.
x represents an integer of 1 to 20.
y represents an integer of 0 to 10.
z represents an integer of 0 to 10.

Xf is a fluorine atom or an alkyl group which is substituted with at least one fluorine atom. This alkyl group preferably has 1 to 10 carbon atoms, and more preferably 1 to 4 carbon atoms. The alkyl group substituted with at least one fluorine atom is preferably a perfluoroalkyl group.

Xf is preferably a fluorine atom or a perfluoroalkyl group having 1 to 4 carbon atoms. Xf is more preferably a fluorine atom or $CF_3$. In particular, it is preferred that both Xf's are a fluorine atom.

Each of $R_1$ and $R_2$ independently represents a hydrogen atom, or an alkyl group.

The alkyl group as $R_1$ and $R_2$ may have a substituent and preferably has 1 to 4 carbon atoms. $R_1$ and $R_2$ are preferably a hydrogen atom.

L represents a divalent linking group. Examples of the divalent linking group may include —COO—, —OCO—, —CONH—, —NHCO—, —CO—, —O—, —S—, —SO—, —SO$_2$—, an alkylene group (preferably having 1 to 6 carbon atoms), a cycloalkylene group (preferably having 3 to 10 carbon atoms), an alkenylene group (preferably having 2 to 6 carbon atoms), and a divalent linking group of combination of a plurality of these. Among these, preferred is —COO—, —OCO—, —CONH—, —NHCO—, —CO—, —O—, —SO$_2$—, a —COO-alkylene group-, an —OCO-alkylene group-, a —CONH-alkylene group-, or an —NHCO-alkylene group- and more preferred is —COO—, —OCO—, —CONH—, —SO$_2$—, a —COO-alkylene group-, or an —OCO-alkylene group-.

Cy represents a cyclic organic group. Examples of the cyclic organic group may include an alicyclic group, an aryl group, and a heterocyclic group.

The alicyclic group may be monocyclic or polycyclic. The monocyclic alicyclic group may be a monocyclic cycloalkyl group such as a cyclopentyl group, a cyclohexyl group, or a cyclooctyl group. The polycyclic alicyclic group may be a polycyclic cycloalkyl group such as a norbornyl group, a tricyclodecanyl group, a tetracyclodecanyl group, a tetracyclododecanyl group, or an adamantyl group. Among them, an alicyclic group with a bulky structure having 7 or more carbon atoms such as a norbornyl group, a tricyclodecanyl group, a tetracyclodecanyl group, a tetracyclododecanyl group, or an adamantyl group is preferred from the viewpoints of inhibiting diffusivity into the film during post exposure bake (PEB) process and improving a mask error enhancement factor (MEEF).

The aryl group may be monocyclic or polycyclic. Examples of the aryl group may include a phenyl group, a naphthyl group, a phenanthryl group, and an anthryl group. Among them, a naphthyl group showing a relatively low light absorbance at 193 nm is preferred.

The heterocyclic group may be monocyclic or polycyclic, but a polycyclic heterocyclic group may further inhibit diffusion of an acid. Also, the heterocyclic group may have aromaticity or may not have aromaticity. Examples of the heterocycle having aromaticity may include a furan ring, a thiophene ring, a benzofuran ring, a benzothiophene ring, a dibenzofuran ring, a dibenzothiophene ring, and a pyridine ring. Examples of the heterocycle having no aromaticity may include a tetrahydropyran ring, a lactone ring, a sultone ring, and a decahydroisoquinoline ring. As the heterocycle in the heterocyclic group, a furan ring, a thiophene ring, a pyridine ring, or a decahydroisoquinoline ring is particularly preferred. Also, examples of the lactone ring and the sultone ring may include the lactone structure and the sultone structure exemplified for the resin (A).

The cyclic organic group may have a substituent. Examples of the substituent may include an alkyl group (which may be either linear or branched, and preferably has 1 to 12 carbon atoms), a cycloalkyl group (which may be monocyclic, polycyclic or spirocyclic, and preferably has 3 to 20 carbon atoms), an aryl group (preferably having 6 to 14 carbon atoms), a hydroxyl group, an alkoxy group, an ester group, an amido group, a urethane group, an ureido group, a thioether group, a sulfonamido group, and a sulfonic acid ester group. Incidentally, the carbon constituting the cyclic organic group (the carbon contributing to the ring formation) may also be a carbonyl carbon.

x is preferably 1 to 8, more preferably 1 to 4, and particularly preferably 1. y is preferably 0 to 4, and more preferably 0. z is preferably 0 to 8, more preferably 0 to 4, and still more preferably 1.

Examples of the fluorine atom-containing group represented by Rf may include an alkyl group having at least one fluorine atom, a cycloalkyl group having at least one fluorine atom and an aryl group having at least one fluorine atom.

These alkyl group, cycloalkyl group, and aryl group may be substituted by a fluorine atom or may be substituted by another fluorine atom-containing substituent. In the case where Rf is a cycloalkyl group having at least one fluorine atom or an aryl group having at least one fluorine atom, examples of the another fluorine-containing substituent include an alkyl group substituted with at least one fluorine atom.

Also, these alkyl group, cycloalkyl group, and aryl group may be further substituted by a fluorine atom-free substituent. Examples of this substituent include those not containing a fluorine atom out of those described above for Cy.

Examples of the alkyl group having at least one fluorine atom represented by Rf are the same as those described above as the alkyl group substituted with at least one fluorine atom represented by Xf. Examples of the cycloalkyl group having at least one fluorine atom represented by Rf include a perfluorocyclopentyl group and a perfluorocyclohexyl group. Examples of the aryl group having at least one fluorine atom represented by Rf include a perfluorophenyl group.

In the general formula, a particularly preferred embodiment is an embodiment in which x is 1, two Xf's are a fluorine atom, y is 0 to 4, all of $R_1$ and $R_2$ are a hydrogen atom, and z is 1. Such an embodiment has a small number of fluorine atoms, exhibits difficulty) in localization on the surface during the resist film formation, and shows readily uniform dispersion into the resist film.

Also, in the present invention, in view of suppressing diffusion of an acid generated by exposure into a non-exposed area, thereby improving a resolution or a pattern profile, the compound (B) which generates an acid is preferably a compound which generates an acid with a volume of 130 Å$^3$ or more (more preferably, a sulfonic acid), more preferably a compound which generates an acid with a volume of 190 Å$^3$ or more (more preferably, a sulfonic acid), still more preferably a compound which generates an acid with a volume of 270 Å$^3$ or more (more preferably, a sulfonic acid), and particularly preferably a compound which generates an acid with a volume of 400 Å$^3$ or more (more preferably, a sulfonic acid). Meanwhile, in view of the sensitivity or the coating solvent solubility, the volume is preferably 2,000 Å$^3$ or less, and more preferably 1,500 Å$^3$ or less. The value of the volume was obtained using, "Win-MOPAC" manufactured by FUJITSU LIMITED. That is, the "accessible volume" of each acid may be calculated by, first, inputting a chemical structure of an acid according to each case, determining the most stable conformation of each acid by a molecular force field calculation using a MM3 method with an initial structure of this structure, and then performing a molecular orbital calculation using a PM3 method for the most stable conformation.

A particularly preferred acid generator in the present invention will be exemplified as below. Also, some examples are given calculated values of volume (unit: Å$^3$). Meanwhile, the value calculated herein is a volume value of an acid in which a proton is bound to an anion moiety.

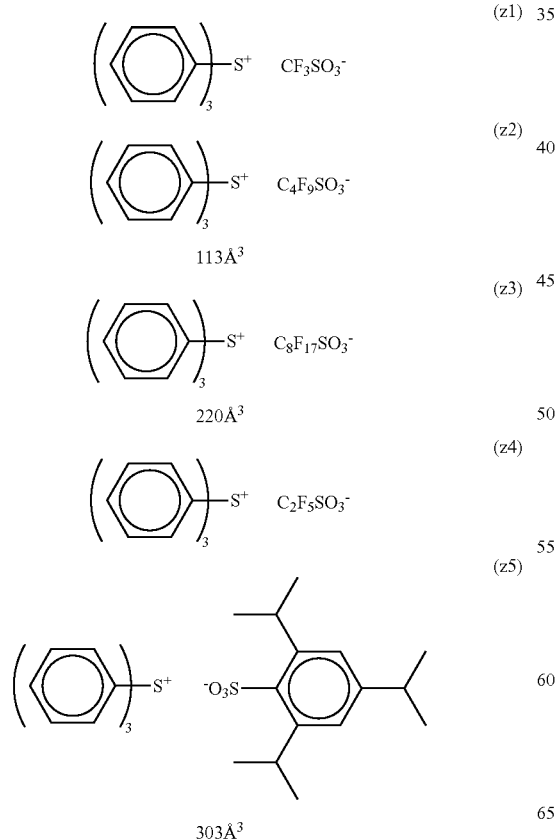

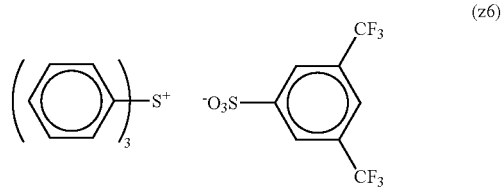

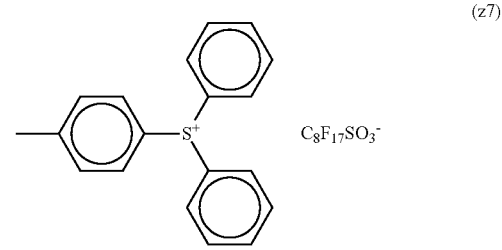

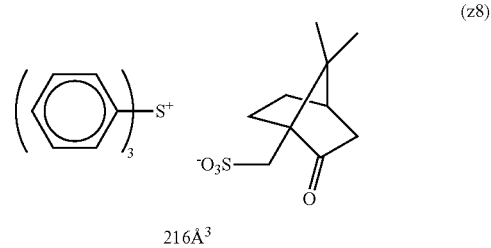

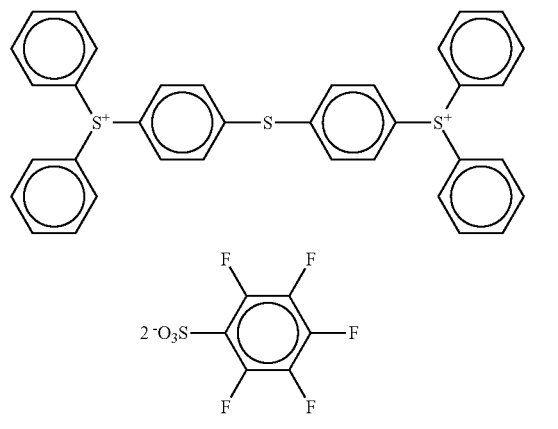

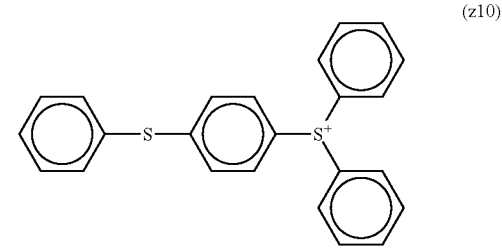

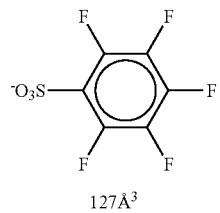

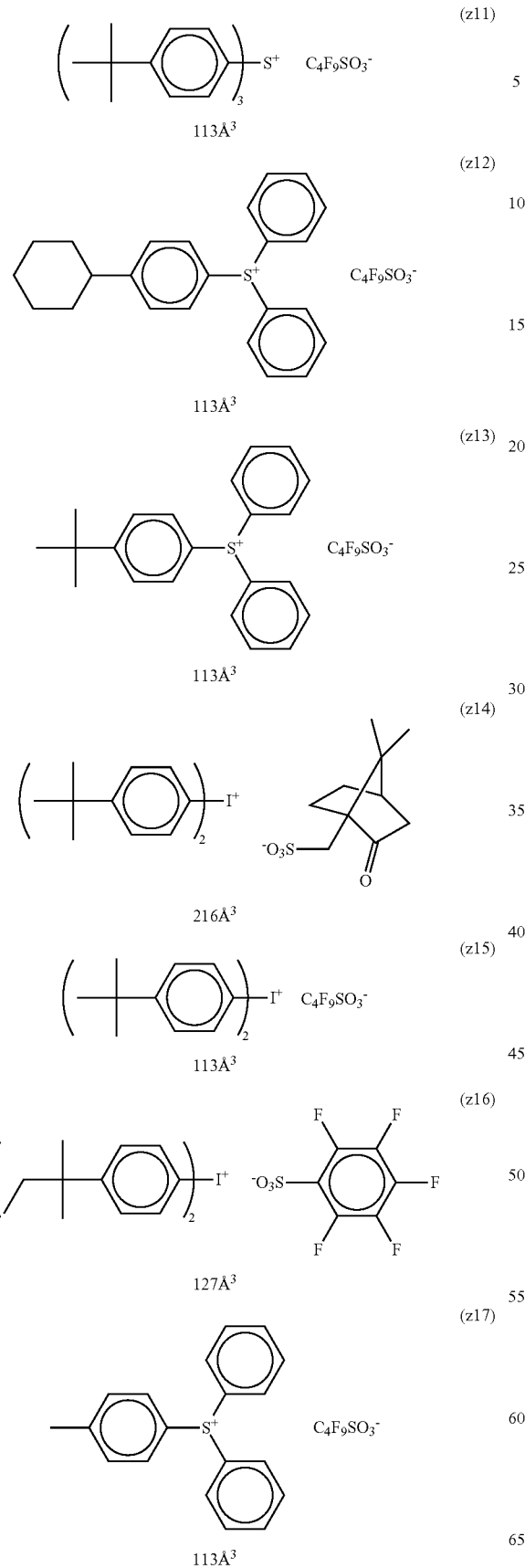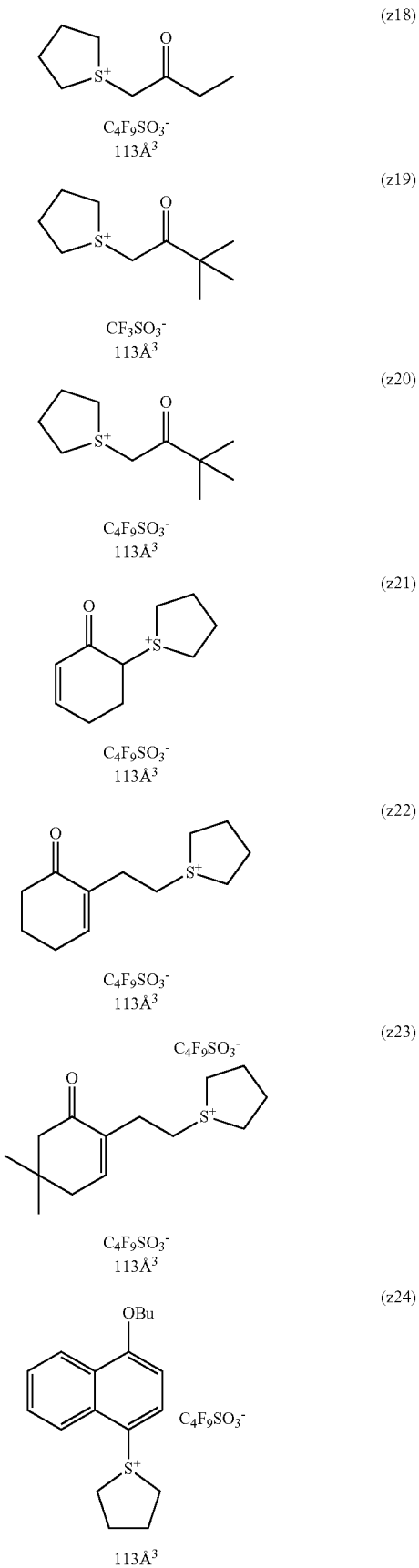

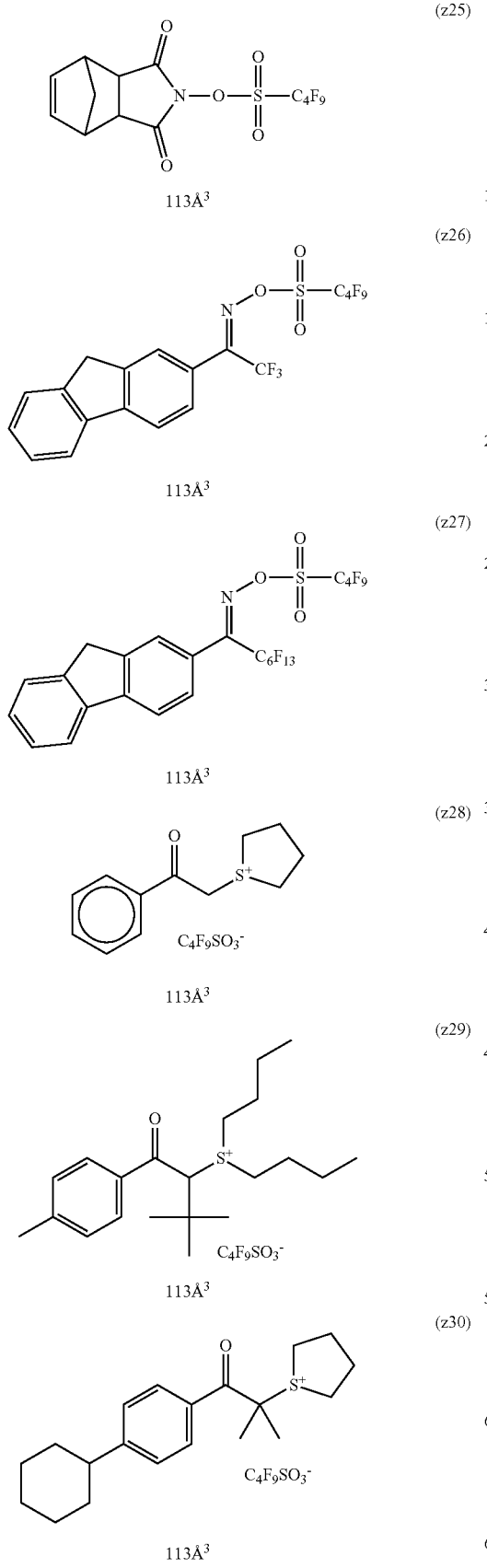
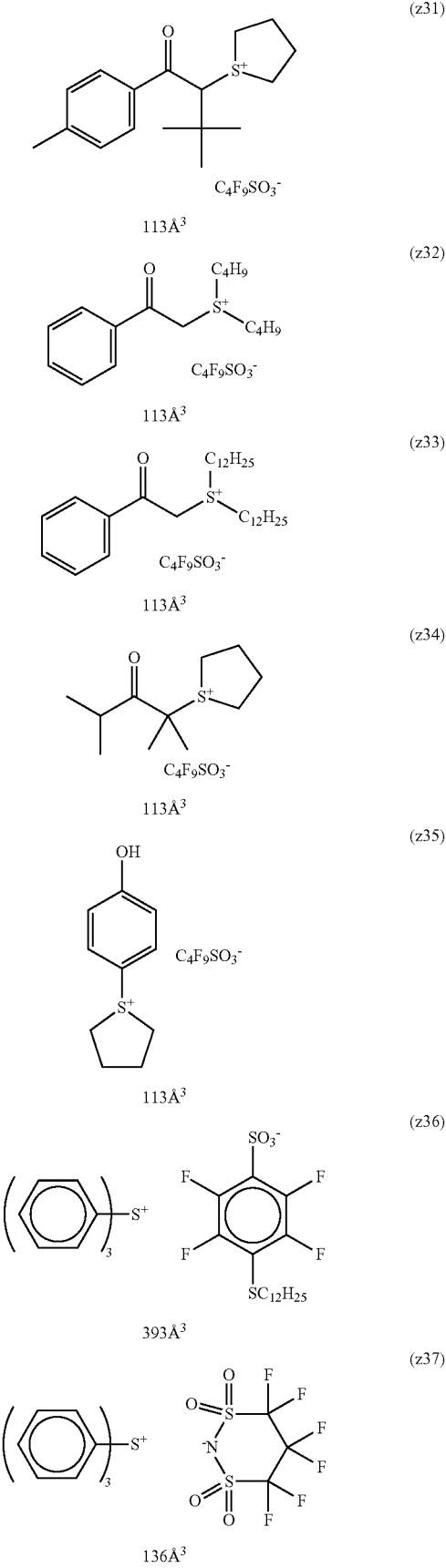

-continued
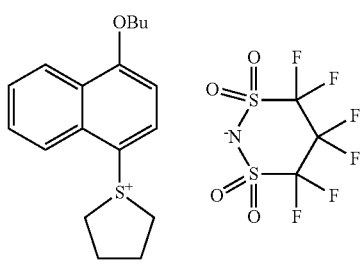
(z38)
136Å³
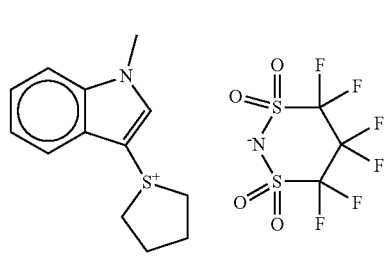
(z39)
136Å³
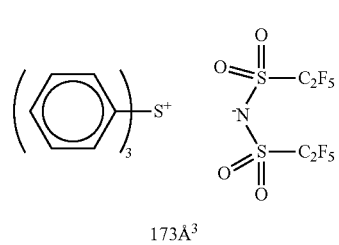
(z40)
173Å³
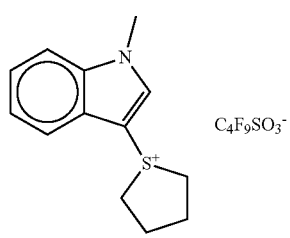
(z41)
113Å³
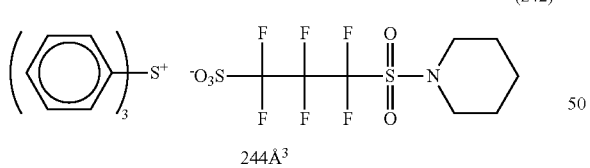
(z42)
244Å³
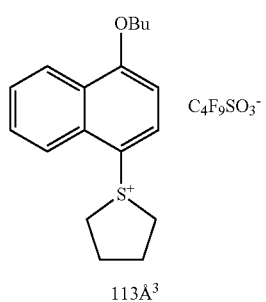
(z43)
113Å³
-continued
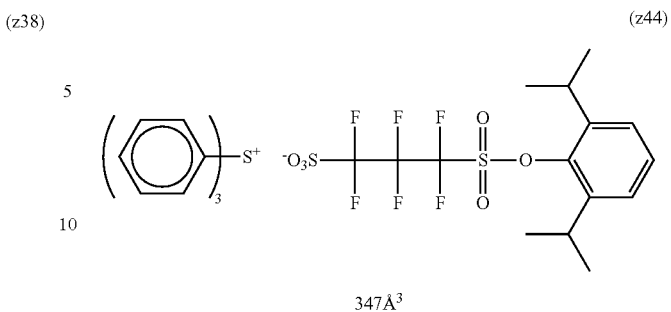
(z44)
347Å³
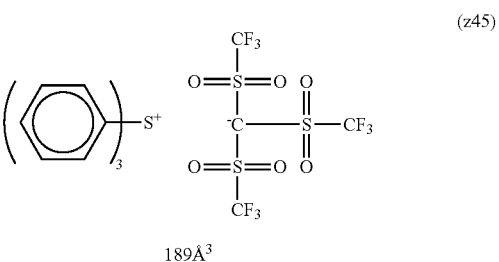
(z45)
189Å³
(z46)
136Å³
(z47)
113Å³
(z48)
186Å³

(z49)
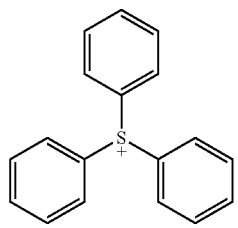 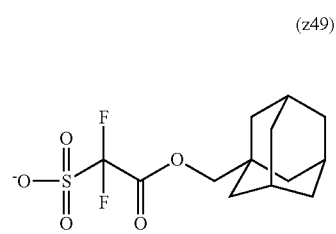
271Å³
(z53)
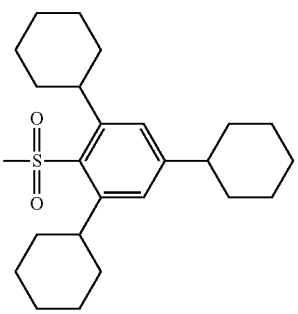
437Å³
(z50)
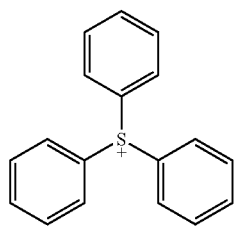 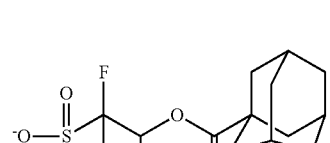
291Å³
(z54)
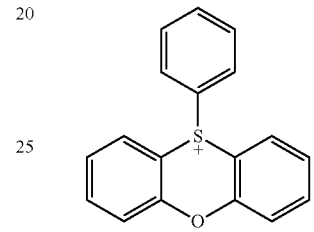
303Å³
(z51)
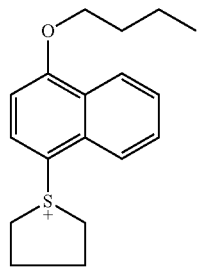 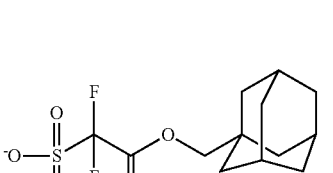
271Å³
(z55)
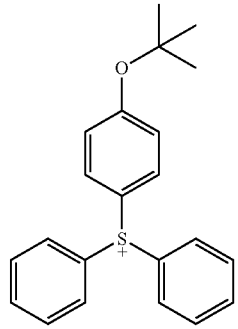
303Å³
(z52)
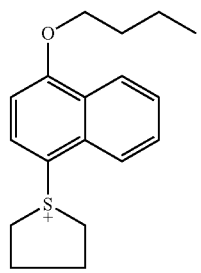 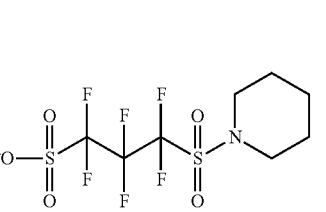
244Å³
(z56)
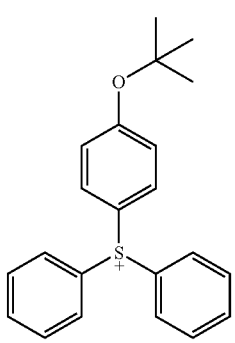
437Å³

-continued
(z57)
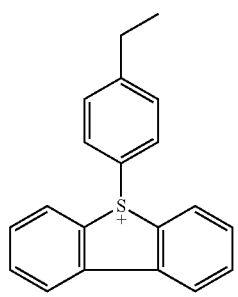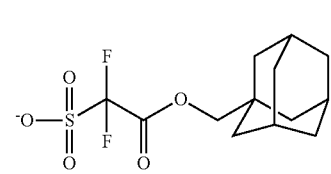
271Å³
(z58)
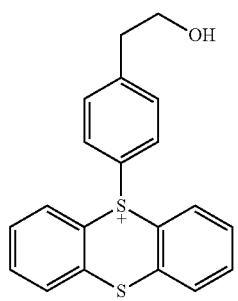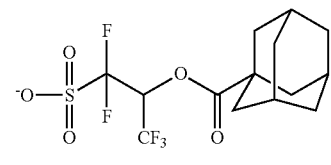
291Å³
(z59)
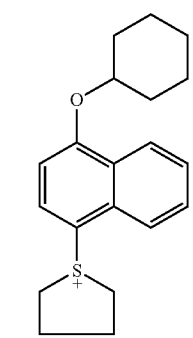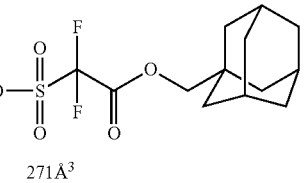
271Å³
(z60)
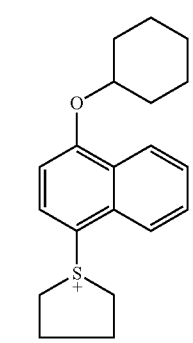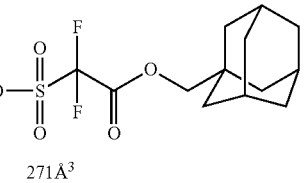
244Å³
-continued
(z61)
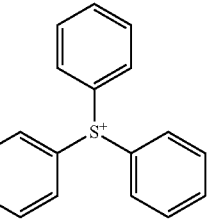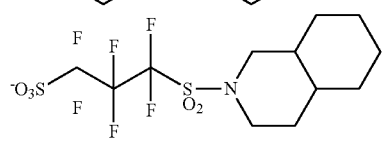
311Å³
(z62)
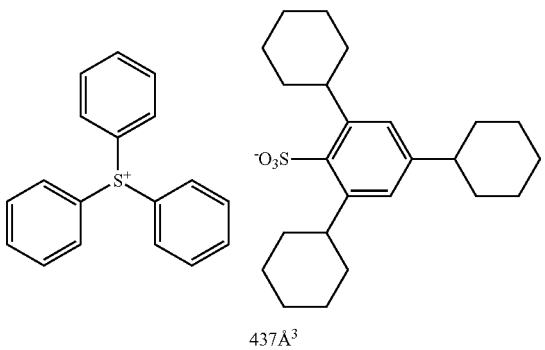
437Å³
(z63)
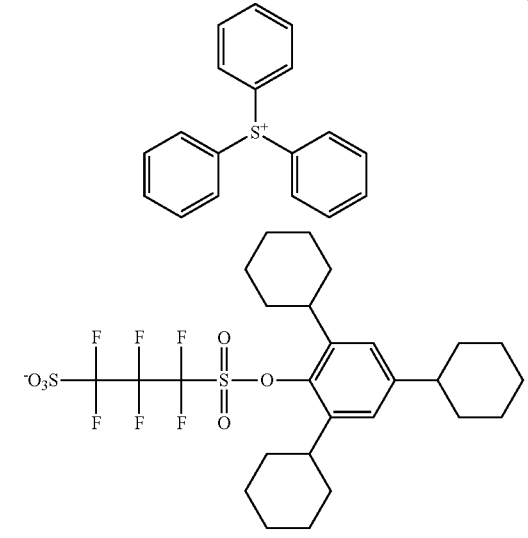
535Å³
(z64)
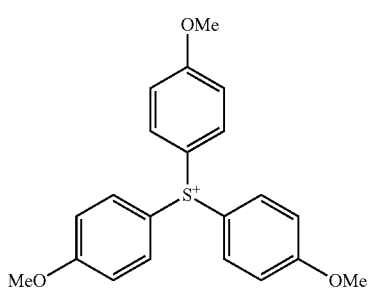

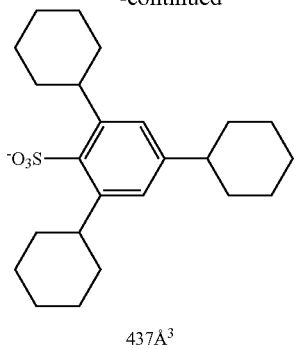

437Å³

(z65)

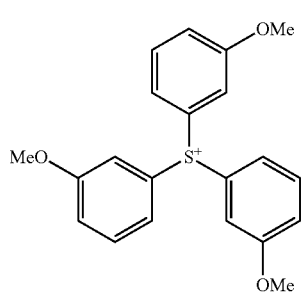

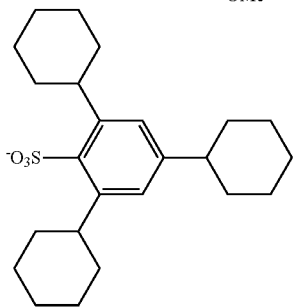

437Å³

(z66)

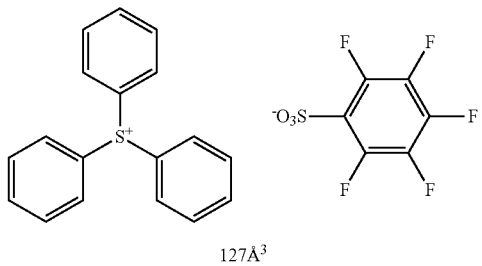

127Å³

As the acid generator (preferably an onium compound) for use in the present invention, a polymer-type acid generator where a group capable of generating an acid upon irradiation with actinic rays or radiation (photoacid-generating group) is introduced into the main or side chain of a polymer compound may also be used, and this acid generator is described as a repeating unit having a photoacid-generating group in connection with the alkali-soluble resin (A).

The content of the acid generator in the composition is preferably 0.1 mass % to 35 mass %, more preferably 0.5 mass % to 30 mass %, and still more preferably 2.5 mass % to 25 mass %, based on the total solid content of the actinic ray-sensitive or radiation-sensitive resin composition.

The acid generator may be used alone or in combination of two or more thereof.

<Another Crosslinking Agent>

As described before, the composition of the present invention may further contain a compound having two or more hydroxymethyl groups or alkoxymethyl groups within the molecule (hereinafter referred to also as "crosslinking agent (C-1)"), as another crosslinking agent other than the crosslinking agent (C) of the present invention.

Examples of the preferred crosslinking agent (C-1) include hydroxymethylated or alkoxymethylated phenol compounds, alkoxymethylated melamine-based compounds, alkoxymethyl glycoluril-based compounds, and alkoxymethylated urea-based compounds. Examples of the compound (C-1) as the particularly preferred crosslinking agent include a phenol derivative having a molecular weight of 1,200 or less and containing, within the molecule, three to five benzene rings and a total of two or more hydroxymethyl groups or alkoxymethyl groups, a melamine-formaldehyde derivative having at least two free N-alkoxymethyl groups, and an alkoxymethyl glycoluril derivative. The alkoxymethyl group is preferably a methoxymethyl group or an ethoxymethyl group.

Among the crosslinking agents, a phenol derivative having a hydroxymethyl group may be obtained by reacting a corresponding phenol compound having no hydroxymethyl group with formaldehyde in the presence of a base catalyst. Also, a phenol derivative having an alkoxymethyl group may be obtained by reacting a corresponding phenol derivative having a hydroxymethyl group with an alcohol in the presence of an acid catalyst.

Among the phenol derivatives synthesized as described above, a phenol derivative having an alkoxymethyl group is particularly preferred in view of the sensitivity and storage stability.

Other preferred examples of the crosslinking agent further include compounds having an N-hydroxymethyl group or an N-alkoxymethyl group, such as alkoxymethylated melamine-based compounds, alkoxymethyl glycoluril-based compounds, and alkoxymethylated urea-based compounds.

As for such compounds, hexamethoxymethylmelamine, hexaethoxymethylmelamine, tetramethoxymethyl glycoluril, 1,3-bismethoxymethyl-4,5-bismethoxyethyleneurea, and bismethoxymethylurea may be exemplified, which are disclosed in EP0133216A, DE3634671B, DE3711264B, and EP0212482A.

Among these crosslinking agents, particularly preferred are those illustrated below.

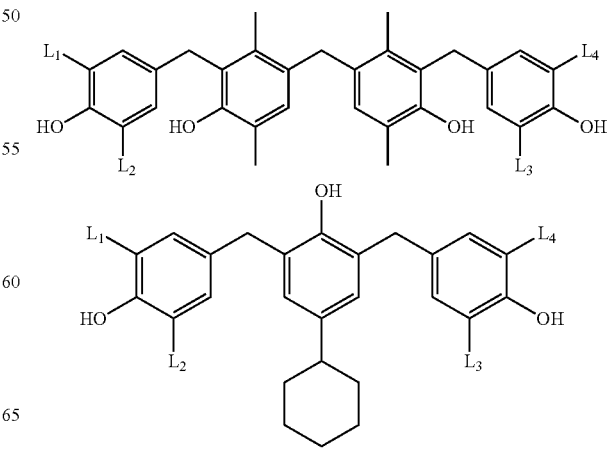

-continued

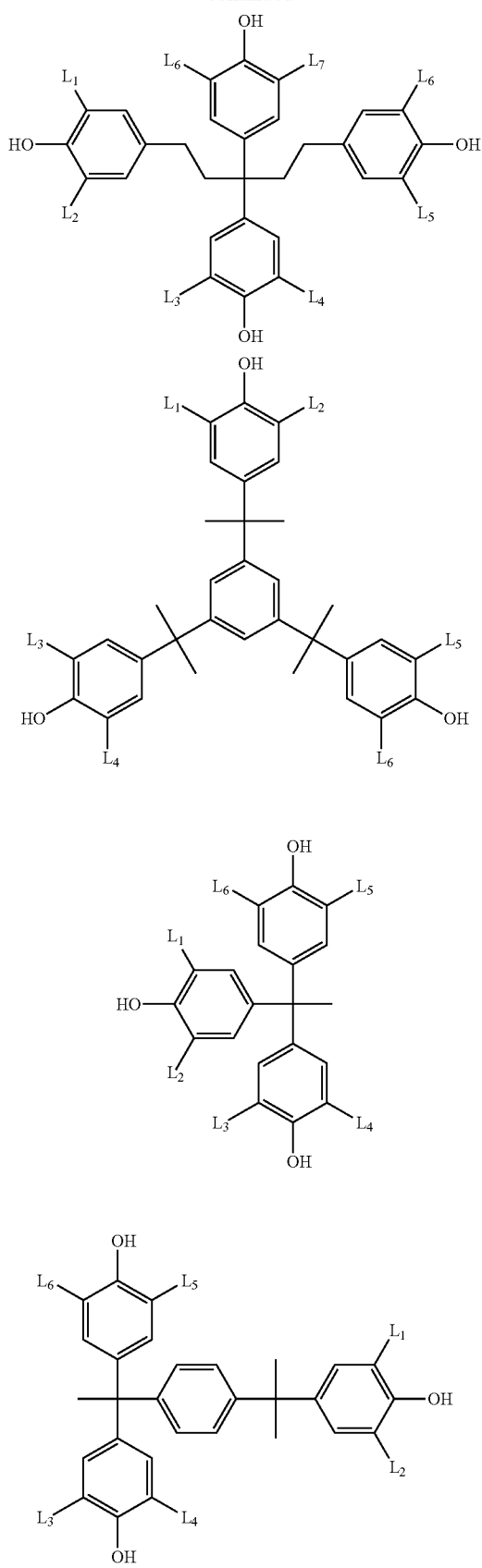

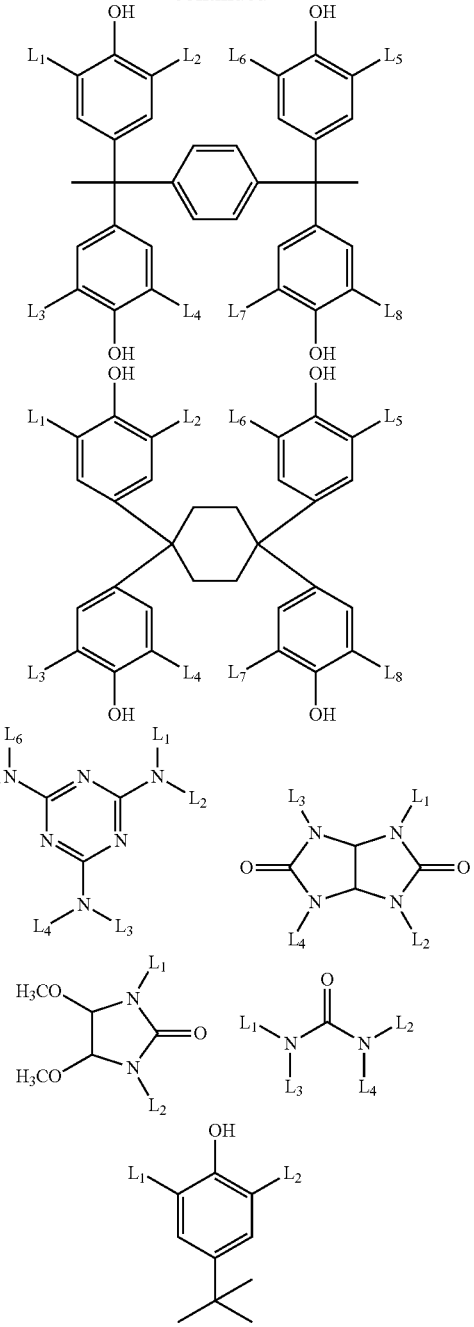

In the formulae, each of $L_1$ to $L_8$ independently represents a hydrogen atom, a hydroxymethyl group, a methoxymethyl group, an ethoxymethyl group, or an alkyl group having 1 to 6 carbon atoms.

In the case where the composition of the present invention contains another crosslinking agent, the amount thereof to be added is preferably, for example, 50 mass % or less, more preferably 1 mass % to 50 mass %, and still more preferably 1 mass % to 20 mass %, based on the crosslinking agent (C) of the present invention.

<Basic Compound>

The composition of the present invention preferably contains a basic compound, in addition to the components described above, as an acid scavenger. By using the basic compound, the change of performance with aging from exposure to post bake may be reduced. The basic compound is preferably an organic basic compound, and more specific examples thereof include aliphatic amines, aromatic amines, heterocyclic amines, a nitrogen-containing compound having a carboxyl group, a nitrogen-containing compound having a sulfonyl group, a nitrogen-containing compound having a hydroxyl group, a nitrogen-containing compound having a hydroxyphenyl group, an alcoholic nitrogen-containing compound, amide derivatives, and imide derivatives. An amine oxide compound (preferably having a methyleneoxy unit and/or an ethyleneoxy unit, for example, compounds described in JP2008-102383A) and an ammonium salt (preferably a hydroxide or a carboxylate: more specifically, a tetraalkylammonium hydroxide typified by tetrabutylammonium hydroxide is preferred in view of LER) may also be appropriately used.

Furthermore, a compound whose basicity is increased by the action of an acid may also be used as a kind of the basic compound.

Specific examples of the amines may include tri-n-butylamine, tri-n-pentylamine, tri-n-octylamine, tri-n-decylamine, triisodecylamine, dicyclohexylmethylamine, tetradecylamine, pentadecylamine, hexadecylamine, octadecylamine, didecylamine, methyloctadecylamine, dimethylundecylamine, N,N-dimethyldodecylamine, methyldioctadecylamine, N,N-dibutylaniline, N,N-dihexylaniline, 2,6-diisopropylaniline, 2,4,6-tri(t-butyl)aniline, triethanolamine, N,N-dihydroxyethylaniline, tris(methoxyethoxyethyl)amine, the compounds exemplified in column 3, line 60 et seq. of U.S. Pat. No. 6,040,112A, 2-[2-{2-(2,2-dimethoxy-phenoxyethoxy)ethyl}-bis-(2-methoxyethyl)]-amine, and compounds (C1-1) to (C3-3) exemplified in paragraph "0066" of US2007/0224539A1. Examples of the compound having a nitrogen-containing heterocyclic structure may include 2-phenylbenzimidazole, 2,4,5-triphenylimidazole, N-hydroxyethylpiperidine, bis(1,2,2,6,6-pentamethyl-4-piperidyl) sebacate, 4-dimethylaminopyridine, antipyrine, hydroxyantipyrine, 1,5-diazabicyclo[4.3.0]nona-5-ene, 1,8-diazabicyclo[5.4.0]-undeca-7-ene, and tetrabutylammonium hydroxide.

In addition, a photodecomposable basic compound (a compound which initially exhibits basicity due to the action of the basic nitrogen atom as a base but decomposes upon irradiation with actinic rays or radiation to generate a zwitterionic compound having a basic nitrogen atom and an organic acid moiety and resulting from neutralization thereof in the molecule, is reduced in or deprived of the basicity; for example, onium salts described in JP3577743B, JP2001-215689A, JP2001-166476A, JP2008-102383A, and JP2013-64970A), and a photobase generator (for example, compounds described in JP2010-243773A) may also be appropriately used.

Among these basic compounds, an ammonium salt is preferred in view of improving resolution.

In the present invention, the basic compound may be used alone or in combination of two or more thereof.

The content of the basic compound used in the present invention is preferably 0.01 mass % to 10 mass %, more preferably 0.03 mass % to 5 mass %, and particularly preferably 0.05 mass % to 3 mass %, based on the total solid content of the composition of the present invention.

<Surfactant>

The composition of the present invention may contain a surfactant in order to further improve the coatability. The surfactant is not particularly limited, but examples thereof may include a nonionic surfactant such as polyoxyethylene alkyl ethers, polyoxyethylene alkylallyl ethers, polyoxyethylene-polyoxypropylene block copolymers, sorbitan fatty acid esters, and polyoxyethylene sorbitan fatty acid esters, a fluorine-based surfactant such as MEGAFACE F171 (manufactured by DIC Corporation), FLORAD FC430 (manufactured by Sumitomo 3M Limited), SURFYNOL E1004 (manufactured by Asahi Glass Co., Ltd.), and PF656 and PF6320 (manufactured by OMNOVA Solutions Inc.) and an organosiloxane polymer.

In the case where the actinic ray-sensitive or radiation-sensitive resin composition contains a surfactant, the amount of the surfactant used is preferably 0.0001 mass % to 2 mass %, and more preferably 0.0005 mass % to 1 mass %, based on the total amount of the composition (excluding the solvent).

<Organic Carboxylic Acid>

The composition of the present invention preferably contains an organic carboxylic acid, in addition to the components described above. Examples of the organic carboxylic acid compound may include an aliphatic carboxylic acid, an alicyclic carboxylic acid, an unsaturated aliphatic carboxylic acid, an oxycarboxylic acid, an alkoxycarboxylic acid, a ketocarboxylic acid, a benzoic acid derivative, a phthalic acid, a terephthalic acid, an isophthalic acid, a 2-naphthoic acid, a 1-hydroxy-2-naphthoic acid, and a 2-hydroxy-3-naphthoic acid. However, when the electron beam exposure is performed in vacuum, the organic carboxylic acid may vaporize from the resist film surface to contaminate the inside of a lithography chamber. Thus, a preferred compound is an aromatic organic carboxylic acid, and above all, for example, a benzoic acid, a 1-hydroxy-2-naphthoic acid, and a 2-hydroxy-3-naphthoic acid are preferred.

The blending amount of the organic carboxylic acid is preferably in the range of 0.01 parts by mass to 10 parts by mass, more preferably 0.01 parts by mass to 5 parts by mass, and still more preferably 0.01 parts by mass to 3 parts by mass, based on 100 parts by mass of the alkali-soluble resin.

The composition of the present invention, as necessary, may further contain a dye, a plasticizer, and an acid amplifier (described in WO95/29968A, WO98/24000A, JP1996-305262A (JP-H08-305262A), JP1997-34106A (JP-H09-34106A), JP1996-248561A (JP-H08-248561A), JP1996-503082A (JP-H08-503082A), U.S. Pat. No. 5,445,917A, JP1996-503081A (JP-H08-503081A), U.S. Pat. Nos. 5,534,393A, 5,395,736A, 5,741,630A, 5,334,489A, 5,582,956A, 5,578,424A, 5,453,345A, 5,445,917A, EP665960B, EP757628B, EP665961B, U.S. Pat. No. 5,667,943A, JP1998-1508A (JP-H10-1508A), JP1998-282642A (JP-H10-282642A), JP1997-512498A (JP-H09-512498A), JP2000-62337A, JP2005-17730A, and JP2008-209889A). As for these compounds, respective compounds described in JP2008-268935A may be exemplified.

<Onium Carboxylate>

The composition of the present invention may contain an onium carboxylate. Examples of the onium carboxylate may include sulfonium carboxylate, iodonium carboxylate, and ammonium carboxylate. Particularly, the onium carboxylate is preferably iodonium carboxylate or sulfonium carboxylate. Also, in the present invention, it is preferred that the carboxylate residue of the onium carboxylate does not contain an aromatic group and a carbon-carbon double bond. The anion moiety is particularly preferably a linear or branched, monocyclic or polycyclic alkylcarboxylate anion having 1 to 30 carbon atoms, and more preferably the carboxylate anion above in which the alkyl group is partially or wholly fluorine-substituted. Also, the alkyl chain may contain an oxygen atom. Accordingly, the transparency to light at 220 nm or less is ensured, and thus the sensitivity and resolution are enhanced, and the iso/dense bias and exposure margin are improved.

<Solvent>

Preferred examples of the solvent used for the composition of the present invention include ethylene glycol monoethyl ether acetate, cyclohexanone, 2-heptanone, propylene glycol monomethyl ether (PGME, another name: 1-methoxy-2-propanol), propylene glycol monomethyl ether acetate (PGMEA, another name: 1-methoxy-2-acetoxypropane), propylene glycol monomethyl ether propionate, propylene glycol monoethyl ether acetate, methyl 3-methoxypropionate, ethyl 3-ethoxypropionate, methyl β-methoxyisobutyrate, ethyl butyrate, propyl butyrate, methyl isobutyl ketone, ethyl acetate, isoamyl acetate, ethyl lactate, toluene, xylene, cyclohexyl acetate, diacetone alcohol, N-methylpyrrolidone, N,N-dimethylformamide, γ-butyrolactone, N,N-dimethylacetamide, propylene carbonate, and ethylene carbonate. These solvents are used alone or in combination thereof.

The solid content of the actinic ray-sensitive or radiation-sensitive resin composition is dissolved in the solvent, and is dissolved at a solid content concentration of preferably 1 mass % to 40 mass %, more preferably 1 mass % to 30 mass %, and still more preferably 3 mass % to 20 mass %.

The present invention also relates to an actinic ray-sensitive or radiation-sensitive film formed by the actinic ray-sensitive or radiation-sensitive resin composition of the present invention, and such an actinic ray-sensitive or radiation-sensitive film is formed, for example, by coating the composition on a support such as a substrate. The thickness of the actinic ray-sensitive or radiation-sensitive film is preferably 0.02 μm to 0.1 μm. As for the method of coating the composition on the substrate, an appropriate coating method such as spin coating, roll coating, flow coating, dip coating, spray coating, and doctor coating may be used. The spin-coating is preferred, and the spinning speed is preferably 1,000 rpm to 3,000 rpm. The coating film is pre-baked at 60° C. to 150° C. for 1 minute to 20 minutes, and preferably at 80° C. to 120° C. for 1 minute to 10 minutes to form a thin film.

As for a material which constitutes a substrate to be processed and its outermost layer, for example, in the case of a wafer for a semiconductor, a silicon wafer may be used, and as an example of a material used as the outermost layer, Si, $SiO_2$, SiN, SiON, TiN, WSi, BPSG, SOG, and an organic antireflection film may be exemplified.

Further, the present invention also relates to mask blank provided with the actinic ray-sensitive or radiation-sensitive film obtained as described above. In the case where a resist pattern is formed on photomask blank for manufacturing a photomask in order to obtain such actinic ray-sensitive or radiation-sensitive film-coated mask blank, for example, a transparent substrate such as quartz and calcium fluoride is used. In general, a light-shielding film, an antireflection film, further a phase shift film, and additionally a required functional film, such as an etching stopper film and an etching mask film, are stacked on the substrate. As for the material of the functional film, a film containing silicon or a transition metal such as chromium, molybdenum, zirconium, tantalum, tungsten, titanium, and niobium is stacked. As the material used for the outermost layer, a material containing, as a main constituent component, a material which contains silicon or contains silicon and oxygen and/or nitrogen; a silicon compound material containing, as a main constituent component, the material described above which further contains a transition metal; and a transition metal compound material containing, as a main constituent component, a material which contains a transition metal, particularly, one or more transition metals selected from chromium, molybdenum, zirconium, tantalum, tungsten, titanium, and niobium, or further contains one or more elements selected from oxygen, nitrogen, and carbon are further exemplified.

The light-shielding film may have a single-layer structure, but more preferably has a multilayer structure where a plurality of materials are applied one on another. In the case of a multilayer structure, the film thickness per layer is not particularly limited, but is preferably 5 nm to 100 nm, and more preferably 10 nm to 80 nm. The thickness of the whole light-shielding film is not particularly limited, but is preferably 5 nm to 200 nm, and more preferably 10 nm to 150 nm.

In the case where the patter formation is performed using a chemical amplification resist composition on the photomask blank having the material containing chromium and oxygen or nitrogen in the outermost layer thereof among the materials described above, a so-called undercut shape having a waisted shape near the substrate is likely to be formed in general. However, in the case of using the present invention, the undercut problem may be improved as compared with the conventional mask blank.

Subsequently, this actinic ray-sensitive or radiation-sensitive film is irradiated with actinic rays or radiation (for example, electron beam), then preferably baked (usually at 80° C. to 150° C., more preferably 90° C. to 130° C., usually for 1 minute to 20 minutes, preferably for 1 minute to 10 minutes), and subsequently developed. In this manner, a good pattern may be obtained. Etching, ion implantation or the like is appropriately performed by using this pattern as the mask to produce, for example, a semiconductor fine circuit, an imprint mold structure, or a photomask.

Meanwhile, the process for preparing an imprint mold by using the composition of the present invention is described, for example, in JP4109085B, JP2008-162101A, and "Basic and Technology Expansion-Application Development of Nanoimprint-Substrate Technology of Nanoimprint and Latest Technology Expansion-edited: Yoshihiko Hirai (Frontier Publishing)."

The usage form of the composition of the present invention and the resist pattern forming method will be subsequently described.

The present invention also relates to a pattern forming method which includes "exposing the actinic ray-sensitive or radiation-sensitive film" or "exposing a mask blank provided with the actinic ray-sensitive or radiation-sensitive film", and "developing the exposed actinic ray-sensitive or radiation-sensitive film" or "developing the exposed mask blank provided with the actinic ray-sensitive or radiation-sensitive film". In the present invention, the exposure is preferably performed using an electron beam or extreme ultraviolet rays.

In the manufacturing of a precision integrated circuit element, at the exposure on the actinic ray-sensitive or radiation-sensitive film (a pattern forming step), first, it is preferred to perform pattern wise irradiation of an electron beam or extreme ultraviolet rays (EUV) on the actinic ray-sensitive or radiation-sensitive film of the present invention. The exposure is performed at an exposure amount ranging from about 0.1 $\mu C/cm^2$ to 20 $\mu C/cm^2$ and preferably about 3 $\mu C/cm^2$ to 10 $\mu C/cm^2$ in a case of an electron beam, and an exposure amount ranging from about 0.1 $mJ/cm^2$ to 20 $mJ/cm^2$ and preferably from about 3 $mJ/cm^2$ to 15 $mJ/cm^2$ in a case of extreme ultraviolet rays. Then, on a hot plate, the film is subjected to post-exposure baking (PEB) at 60° C. to 150° C. for 1 minute to 20 minutes, preferably at 80° C. to 120° C. for 1 minute to 10 minutes, and then is developed, rinsed and dried to form a resist pattern. The development is performed using an aqueous alkali solution such as tetramethylammonium hydroxide (TMAH) or tetrabutylammonium hydroxide (TBAH) (preferably 0.1 mass % to 5 mass %, more preferably 2 mass % to 3 mass %) as for the developer through a conventional method such as a dip method, a puddle method, or a spraying method for preferably 0.1 minutes to 3 minutes and more preferably 0.5 minutes to 2 minutes. To the alkali developer, alcohols and/or a surfactant may be added in an appropriate amount. The pH of the alkali developer is generally 10.0 to 15.0. Particularly, an aqueous solution including 2.38 mass % of tetramethylammonium hydroxyde is preferred.

If necessary, alcohols and/or a surfactant may be added in an appropriate amount to the developer.

The surfactant is not particularly limited, but, for example, ionic or nonionic fluorine-based and/or silicon-based surfactant may be used. Examples of the fluorine and/or silicon-based surfactant may include surfactants described in JP1987-36663A (JP-S62-36663A), JP1986-226746A (JP-S61-226746A), JP1986-226745A (JP-S61-226745A), JP1987-170950A (JP-S62-170950A), JP1988-34540A (JP-S63-34540A), JP1995-230165A (JP-H07-230165A), JP1996-62834A (JP-H08-62834A), JP1997-54432A (JP-H09-54432A), JP1997-5988A (JP-H09-5988A), U.S. Pat. Nos. 5,405,720A. 5,360,692A, 5,529,881A, 5,296,330A, 5,436,098A, 5,576,143A, 5,294,511A, and 5,824,451A, and a nonionic surfactant is preferred. The nonionic surfactant is not particularly limited, but a fluorine-based surfactant or a silicon-based surfactant is more preferably used.

The amount of the surfactant to be used is usually 0.001 mass % to 5 mass %, preferably 0.005 mass % to 2 mass %, and more preferably 0.01 mass % to 0.5 mass %, based on the total amount of the developer.

As for the developing method, it is possible to apply, for example, a method of dipping a substrate in a bath filled with a developer for a predetermined time (a dipping method), a method of heaping up a developer on a substrate surface by a surface tension and keeping the substrate still for a fixed time, thereby performing development (a puddle method), a method of spraying a developer on a substrate surface (a spraying method), and a method of continuously ejecting a developer on a substrate spinning at a constant speed while scanning a developer ejecting nozzle at a constant rate (a dynamic dispense method).

In the case where the aforementioned various developing methods include a step of ejecting a developer toward a resist film from a development nozzle of a developing apparatus, the ejection pressure of the ejected developer (the flow rate per unit area of the ejected developer) is preferably 2 mL/sec/mm$^2$ or less, more preferably 1.5 mL/sec/mm$^2$ or less, and still more preferably 1 mL/sec/mm$^2$ or less. The flow rate has no particular lower limit, but is preferably 0.2 mL/sec/mm$^2$ or more in consideration of throughput.

By setting the ejection pressure of the ejected developer to fall within the above-described range, pattern defects resulting from the resist residue after development may be significantly reduced.

Details on the mechanism are not clear, but it is thought that it is because by setting the ejection pressure to fall within the above-described range, the pressure imposed on the actinic ray-sensitive or radiation-sensitive film by the developer is decreased and the actinic ray-sensitive or radiation-sensitive film pattern is suppressed from being inadvertently cut or collapsing.

Meanwhile, the ejection pressure (mL/sec/mm$^2$) of the developer is the value at the outlet of the development nozzle in the developing apparatus.

Examples of the method for adjusting the ejection pressure of the developer may include a method of adjusting the ejection pressure by a pump or the like, a method of supplying a developer from a pressurized tank and adjusting the pressure to change the ejection pressure, and the like.

In addition, after the step of performing development using a developer, a step of stopping the development while replacing the solvent with another solvent may be performed.

As for the rinsing liquid in the rinse treatment performed after the alkali development, pure water is used, and an appropriate amount of a surfactant may be added to be used therewith.

In this manner, in the negative pattern forming method using the composition of the present invention, an actinic ray-sensitive or radiation-sensitive film at an unexposed area is dissolved, and an exposed area is hardly dissolved in the developer due to crosslinking of a polymer compound, whereby a desired pattern is formed on the substrate.

The pattern forming method of the present invention can also be used for guide pattern formation in DSA (Directed Self-Assembly) (see, for example, ACS Nano Vol. 4, No. 8, pp. 4815-4823).

The resist pattern formed according to the aforementioned method may also be used as a core material (core) in the spacer process disclosed in JP1991-270227A (JP-H03-270227A) and JP2013-164509A.

The present invention also relates to a photomask obtained by a method including exposing the actinic ray-sensitive or radiation-sensitive film provided by a mask blank and developing the exposed film. As for the exposure and development, the steps described above are applied. The photomask is suitably used for manufacturing a semiconductor.

The photomask in the present invention may be a light transmission type mask used in, for example, ArF excimer laser, or a light reflective mask used in a reflective system lithography using EUV light as a light source.

Further, the present invention also relates to a method for manufacturing a semiconductor device, which includes the above-described pattern forming method, and a semiconductor device manufactured by the manufacturing method.

The semiconductor device of the present invention is suitably mounted in electrical and electronic devices (for example, home appliances, OA/media-related devices, optical devices, and communication devices).

EXAMPLES

Hereinafter, the present invention will be described with reference to examples, but is not limited thereto.

Synthesis of Crosslinking Agent

Synthesis Example 1

Synthesis of Crosslinking Agent (C-1)

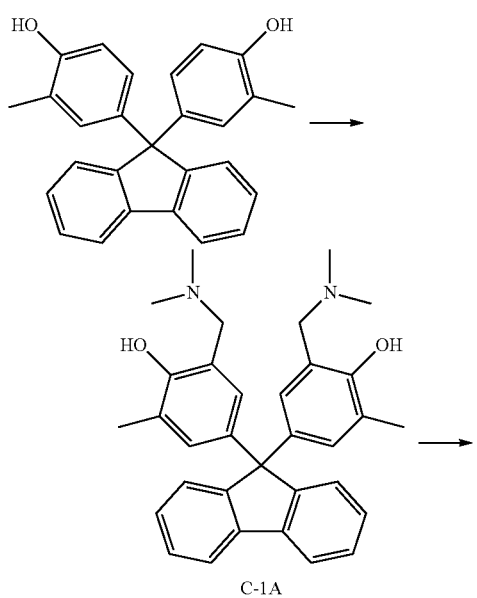

C-1A

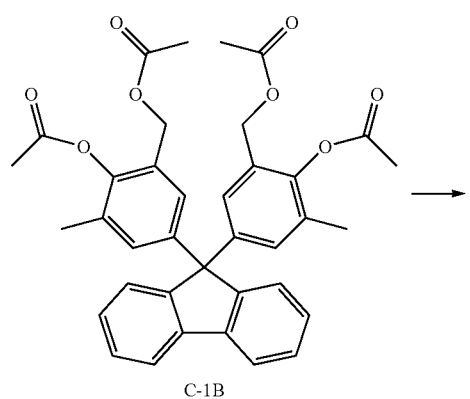

C-1B

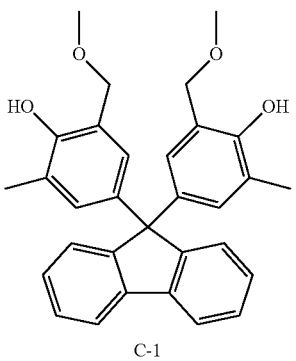

C-1

(Synthesis of Compound (C-1A))

A mixture of 18.8 g of 9,9-bis(4-hydroxy-3-methylphenyl)fluorene (manufactured by Wako Pure Chemical Industries, Ltd.), 19.8 g of a 50% aqueous dimethylamine solution, 6.6 g of paraformaldehyde, and 10 mL of ethanol was stirred at 80° C. for 2 hours. After ethanol was distilled off, 50 mL of ethyl acetate and 50 mL of water were added to the mixture to carry out liquid separation. The organic layer was washed twice with 50 mL of water. The resulting organic layer was dried over magnesium sulfate, dried and then filtered. The solvent in the filtrate was distilled off to give 23.4 g (yield: 95%) of (C-1A) as a crude product. FIG. 1 shows a $^1$H-NMR (acetone-d6) chart of the compound (C-1A).

(Synthesis of Compound (C-1B))

To 23.4 g of the above-obtained compound (C-1A) was added 37.2 g of an acetic anhydride, followed by stirring at 80° C. for 6 hours. After allowing to cool, acetic acid and acetic anhydride were distilled off to give 27.1 g of a compound (C-1B). The compound (C-1B) was used in the synthesis of compound (C-1) without further purification.

(Synthesis of Compound (C-1))

Figure 2:
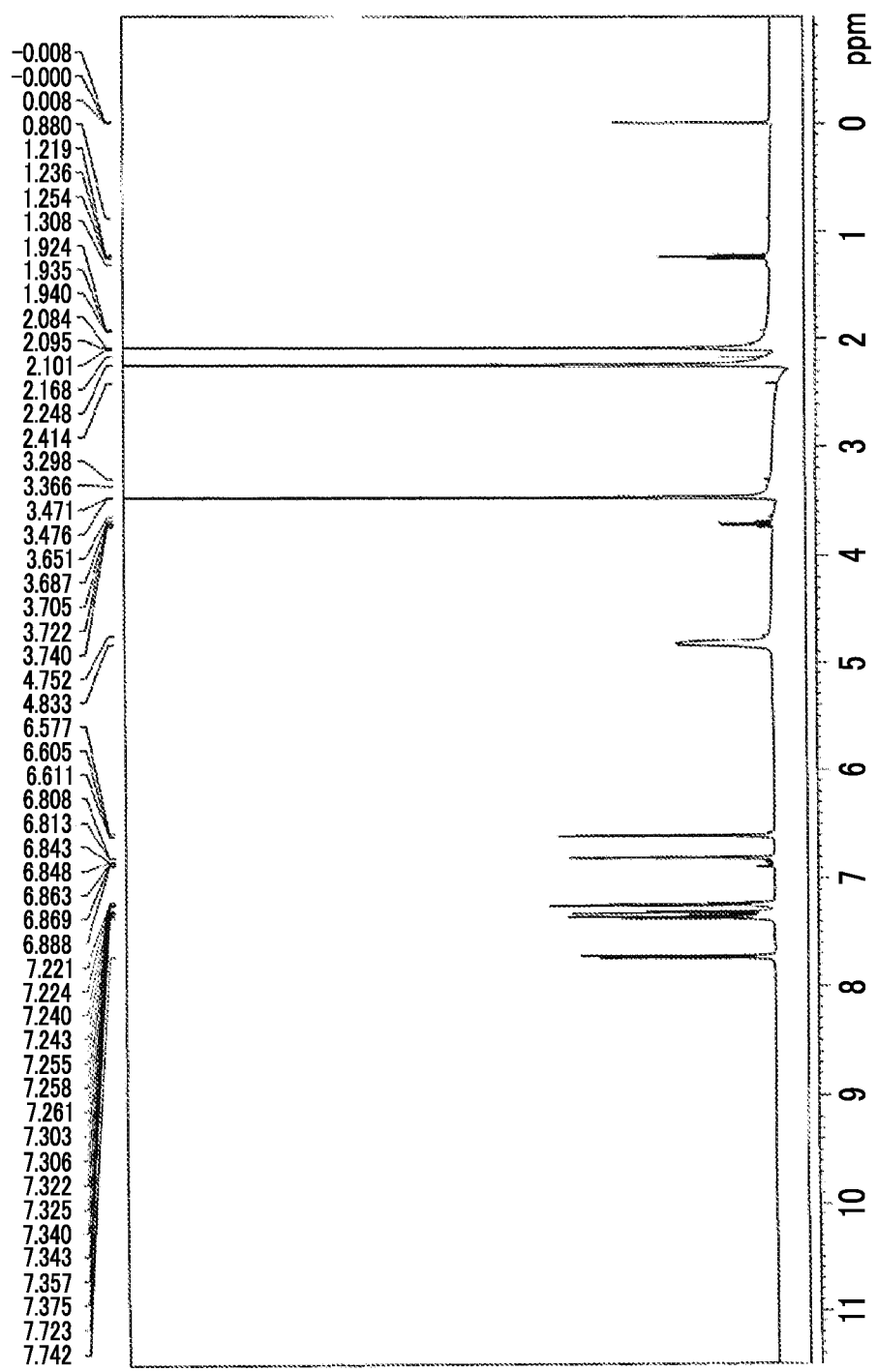
FIG. 2 shows an NMR chart ($^1$HNMR, acetone-d6) of a compound (C-1A) which is an intermediate of a crosslinking agent (C-1) synthesized in Examples.

To 27.1 g of the above-obtained compound (C-1B) were added 58 g of methanol and 6.9 g of potassium carbonate, and the mixture was stirred at 60° C. for 2 hours. After allowing to cool, methanol was distilled off. 100 mL of ethyl acetate and 100 mL of water were added to the mixture to carry out liquid separation, and the organic layer was washed with 100 mL of a 1N aqueous hydrochloric acid solution and then washed three times with 100 mL of water. The resulting organic layer was dried over magnesium sulfate, the desiccant agent was filtered, and the solvent in the filtrate was distilled off to give 19.8 g (total yield: 85%) of a compound (C-1). FIG. 2 shows a $^1$H-NMR (acetone-d6) chart of the compound (C-1).

Other compounds (C-2) to (C-5) described below were also synthesized in the same manner using a bisphenol compound corresponding thereto, respectively.

Synthesis of Alkali-Soluble Resin

Synthesis Example 1

Synthesis of Alkali-soluble Resin (A-2)

The alkali-soluble resin (A-2) was synthesized as follows.

20 g of poly(p-hydroxystyrene)(VP2500) manufactured by Nippon Soda Co., Ltd. was dissolved in 120 mL of tetrahydrofuran (THF), and 4.96 g of I-adamantanecarbonyl chloride and 3.37 g of triethylamine were added thereto. The mixture was stirred at 50° C. for 4 hours. The reaction solution was returned to room temperature. Thereafter, 100 mL of ethyl acetate and 100 mL of distilled water were added thereto, and a 1N HCl aqueous solution was little by little added to the reaction solution while stirring the reaction solution in ice water, such that the reaction solution was neutralized. The reaction solution was transferred to a separating funnel, and 100 mL of ethyl acetate and 100 mL of distilled water were further added. After stirring, the aqueous layer was removed. Thereafter, the organic layer was washed five times with 200 mL of distilled water. The organic layer was then concentrated and added dropwise to 2 L of hexane. The powder was filtered, aliquoted and then dried in vacuo to give 20.6 g of an alkali-soluble resin (A-2).

Synthesis Example 2

Synthesis of Alkali-soluble Resin (A-6)

The alkali-soluble resin (A-6) was synthesized as follows.

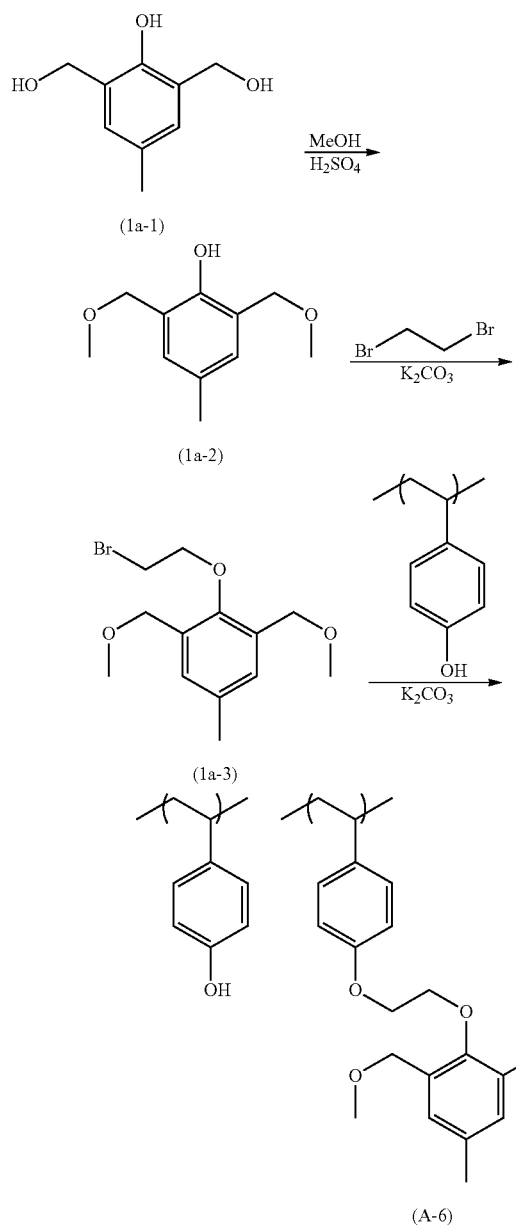

(Synthesis of Compound (1a-2))

35 g of 2,6-bis(hydroxymethyl)-p-cresol (1a-1) manufactured by Tokyo Chemical Industry Co., Ltd. was dissolved in 400 mL of methanol. 3.6 g of a 45% sulfuric acid aqueous solution was added dropwise thereto, followed by stirring at 50° C. for 5 hours. After the reaction was completed, the reaction solution was returned to room temperature. Then, sodium carbonate was added while stirring the reaction solution in an ice bath. The reaction solution was filtered through Celite. The filtrate was concentrated and then transferred to a separating funnel. To this filtrate were added 200 mL of distilled water and 200 mL of ethyl acetate, followed by extraction, and the aqueous layer was removed. Thereafter, the organic layer was washed five times with 200 mL of distilled water. The organic layer was concentrated to give 37 g of a compound (1a-2).

(Synthesis of Compound (1a-3))

20 g of the compound (1a-2) synthesized above was dissolved in 200 mL of dimethylsulfoxide. 38.3 g of dibromoethane and 16.9 g of potassium carbonate were added thereto, followed by stirring at 40° C. for 4 hours. After the reaction was completed, the reaction solution was returned to room temperature, and 100 mL of ethyl acetate and 100 mL of distilled water were added thereto. The reaction solution was transferred to a separating funnel, and the aqueous layer was removed. Thereafter, the organic layer was washed five times with 200 mL of distilled water, and the organic layer was concentrated. The concentrate was purified by silica gel column chromatography (developing solvent: hexane/ethyl acetate=20/1). After the solvent was distilled off under reduced pressure, the concentrate was dried in vacuo to give 24.7 g of a compound (1a-3).

(Synthesis of Alkali-Soluble Resin (A-6))

5 g of poly(p-hydroxystyrene)(VP2500) manufactured by Nippon Soda Co., Ltd. was dissolved in 30 g of dimethylsulfoxide. 1.7 g of potassium carbonate and 2 g of the above-synthesized compound (1a-3) were sequentially added thereto, followed by stirring at 60° C. for 2 hours. After the reaction was completed, the reaction solution was returned to room temperature, and 50 mL of ethyl acetate and 50 mL of distilled water were added thereto. The reaction solution was transferred to a separating funnel, and the aqueous layer was removed. Thereafter, the organic layer was washed five times with 50 mL of distilled water, and the organic layer was concentrated and added dropwise to 500 mL of hexane. The powder was filtered, aliquoted and then dried in vacuo to give 5.4 g of an alkali-soluble resin (A-6) containing the aforementioned repeating unit.

Synthesis Example 3

Synthesis of Alkali-Soluble Resin (A-5)

The alkali-soluble resin (A-5) was synthesized as follows.

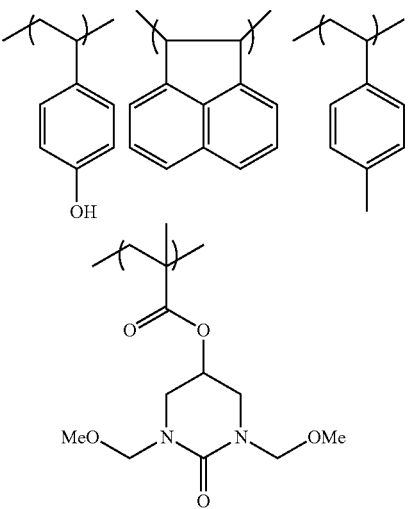

Monomer Synthesis Example 1

Synthesis of 1,3-bismethoxymethyl-2-oxohexahydropyrimidin-5-yl methacrylate (Z-1)

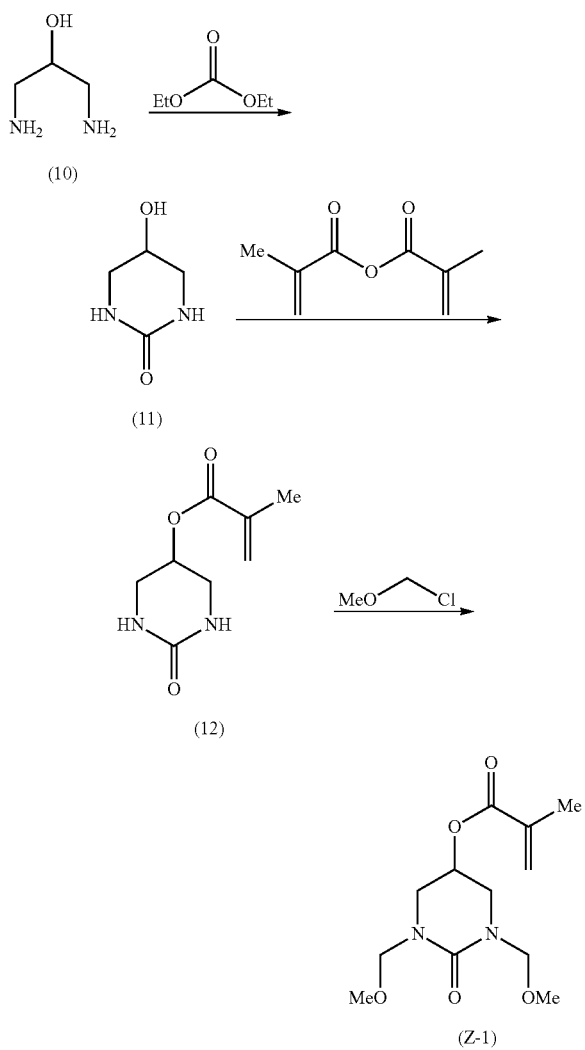

Monomer Synthesis Example 1-1

Synthesis of 5-hydroxytetrahydropyrimidin-2-one (11)

49.1 g of 1,3-diamino-2-propanol (10), 64.4 g of diethyl carbonate, and 3.79 g of 1,5,7-triazabicyclo[4,4,0]deca-5-ene were mixed and heated under reflux for 6 hours. Stirring was continued for a further 10 hours while gradually removing ethanol formed during the reaction. Thereafter, the solvent and diethyl carbonate were distilled off under reduced pressure to give 64.4 g (yield: 100%) of a desired 5-hydroxytetrahydropyrimidin-2-one (11). The resulting product was used in the next step without further purification.

Monomer Synthesis Example 1-2

Synthesis of 2-oxohexahydropyrimidin-5-yl methacrylate (12)

9.0 g of 5-hydroxytetrahydropyrimidin-2-one (11) obtained in (Monomer Synthesis Example 1-1) was dissolved in a mixed solvent of 45.0 g of tetrahydrofuran (THF) and 36.0 g of $H_2O$. To this solution were added dropwise 17.2 g of methacrylic anhydride and 17.8 g of a 25 mass % NaOH aqueous solution at 30° C. or lower. After stirring at that temperature for 3 hours, a conventional aftertreatment operation was carried out. The resulting crude product was dissolved in $CH_3CN$, and then the solution was added dropwise to diisopropylether to give 8.3 g (yield: 60%) of a desired 2-oxohexahydropyrimidin-5-yl methacrylate (12).

Monomer Synthesis Example 1-3

Synthesis of 1,3-bismethoxymethyl-2-oxohexahydropyrimidin-5-yl methacrylate (Z-1)

5.3 g of diisopropylethylamine, 10 g of 2-oxohexahydropyrimidin-5-yl methacrylate (12) obtained in (Monomer Synthesis Example 1-2), and 20.0 g of sodium iodide were added and mixed in 80 g of $CH_3CN$. 11.0 g of chloromethylmethylether was added dropwise at a temperature of 10° C. or lower. After the completion of dropwise addition, the reaction mixture was warmed to room temperature and stirred for 5 hours, followed by a conventional aftertreatment operation. The reaction product was purified by silica gel column chromatography to give 7.5 g (yield: 51%) of a desired 1,3-bismethoxymethyl-2-oxohexahydropyrimidin-5-yl methacrylate (Z-1).

(Synthesis of Alkali-Soluble Resin (A-5))

Under nitrogen atmosphere, 48.2 g of 4-acetoxystyrene, 6.0 g of 4-methylstyrene, 6.5 g of acenaphthalene, 9.3 g of a polymerizable crosslinking agent Z-1, 7.8 g of dimethyl-2,2'-azobis-(2-methylpropionate) (manufactured by Wako Pure Chemical Industries, Ltd., trade name V601), and 82.0 g of toluene as a solvent were charged into 250 mL of a dropping cylinder, whereby a solution was prepared. In addition, under nitrogen atmosphere, 82.0 g of toluene was charged into another 1 L polymerization flask which was then warmed to 80° C. To this 1 L polymerization flask was added dropwise the above-prepared solution over 4 hours. After the completion of dropwise addition, stirring was continuously carried out for 18 hours while mainting the polymerization temperature at 80° C., followed by cooling to room temperature. The resulting polymerization solution was added dropwise to 1,000 g of hexane, and the precipitated copolymer was separated by filtration. The separated copolymer was washed twice with 200 g of a 10:1 mixture of hexane and toluene. The resulting copolymer was dissolved in a mixed solvent of 126 g of tetrahydrofuran and 42 g of methanol in a 1 L flask under nitrogen atmosphere. 18.1 g of ethanolamine was added to the mixture, followed by stirring at 60° C. for 3 hours. This reaction solution was concentrated under reduced pressure, and the resulting concentrate was dissolved in a mixed solvent of 300 g of ethyl acetate and 80 g of water. The resulting solution was transferred to a separating funnel, and 9.1 g of acetic acid was added to carry out liquid separation. The lower layer was removed. 80 g of water and 12.1 g of pyridine were added to the resulting organic layer to carry out liquid separation. The lower layer was further removed, and 80 g of water was added to the resulting organic layer to carry out separating and washing with water (separating and washing with water: five times in total). When allowing to stand for each step of liquid separation, adding 20 g of acetone and some stirring could carry out the liquid separation with good separation.

The organic layer after the liquid separation was concentrated, and the concentrate was dissolved in 140 g of acetone. Then, this acetone solution was added dropwise to 2,800 g of water through a 0.02 μm nylon filter, thereby obtaining the crystallized precipitate. The crystallized precipitate was filtered, washed with water, and filtered with suction for 2 hours. The resulting filtrate was dissolved again in 150 g of acetone. Subsequently, this acetone solution was added dropwise to 2,800 g of water through a 0.02 μm nylon filter, thereby obtaining the crystallized precipitate. The crystallized precipitate was filtered, washed with water, and dried containing to give 42.0 g of a white alkali-soluble resin (A-5) the aforementioned repeating unit.

Other alkali-soluble resins described below were also synthesized in the same manner as the above-described synthesis method.

[Crosslinking Agent]

As the crosslinking agent, the following compounds were used.

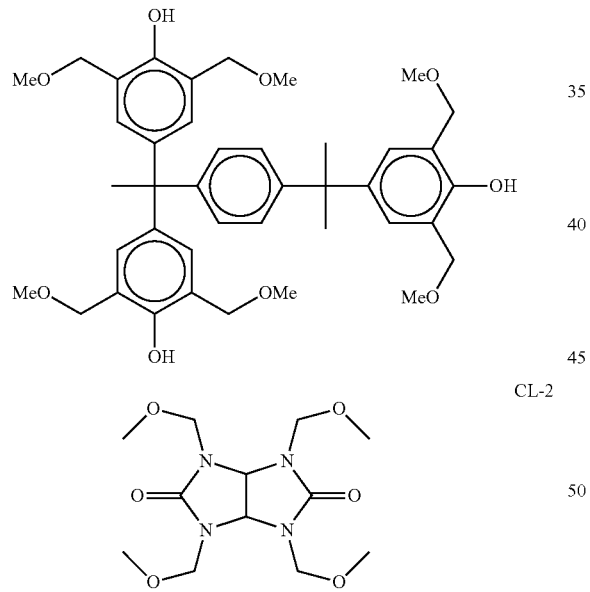
CL-1

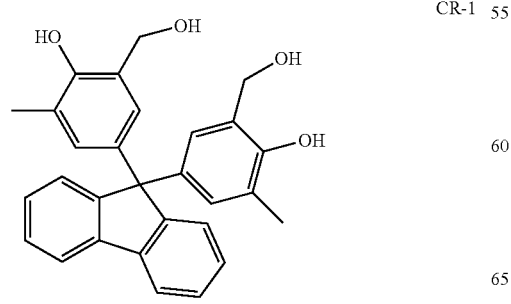
CL-2

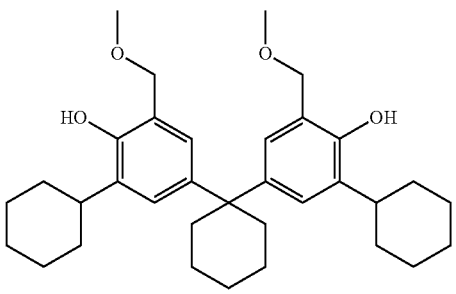
CR-1

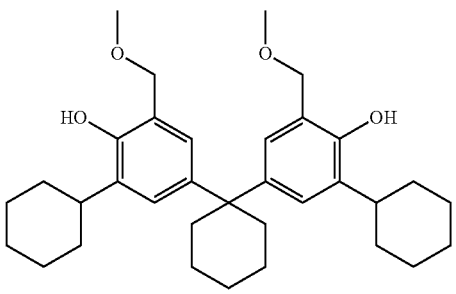
CR-2

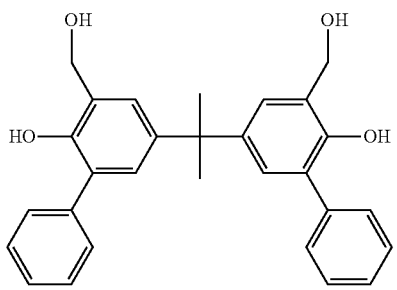
CR-3

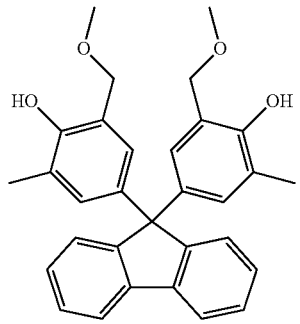
C-1

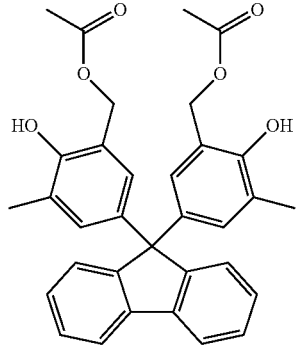
C-2

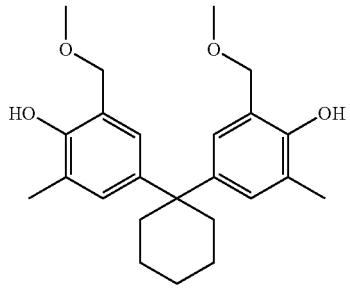
C-3

C-4

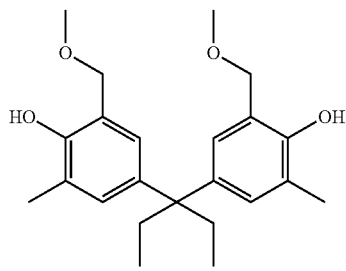

C-5

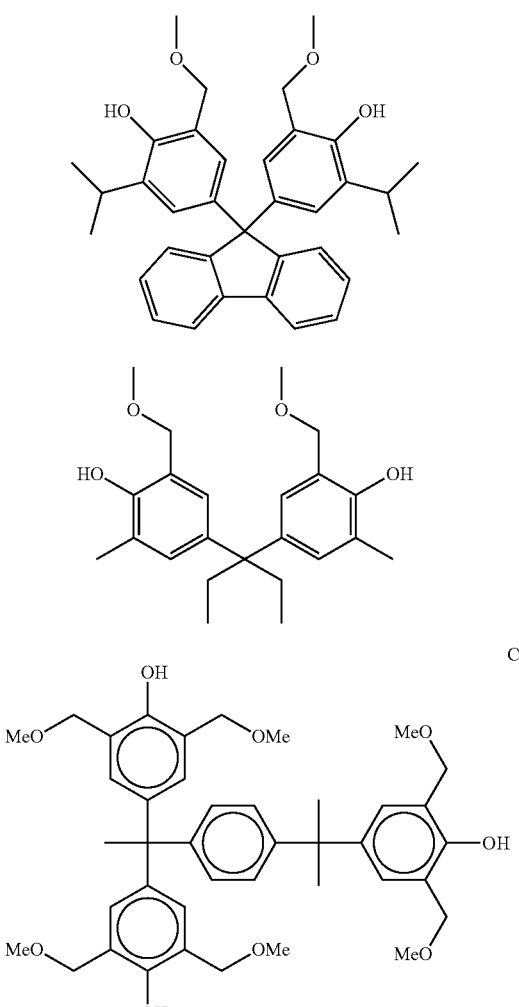

CL-1

CL-2

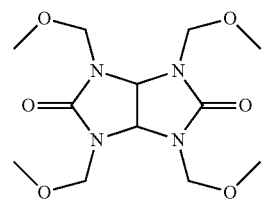

CR-1

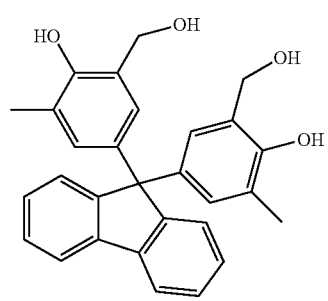

CR-2

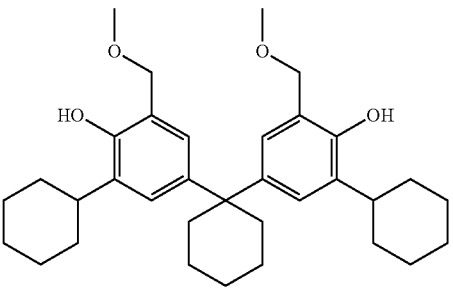

CR-3

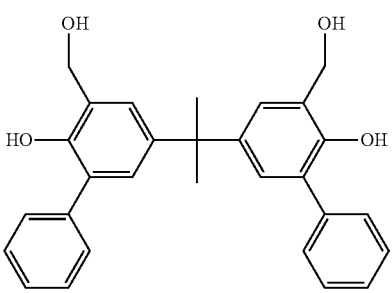

In Examples and Comparative Examples listed in the following Table 1, components described below were used.

[Alkali-soluble Resin]

As the alkali-soluble resin, resins A-1 to A-8 given below were used. The composition ratio (molar ratio), weight average molecular weight (Mw), and polydispersity (weight average molecular weight (Mw)/number average molecular weight (Mn): PDI) are given therewith. In addition, an acid generated from the resin A-7 is fixed to the resin A-7, and a volume of the acid exceeds 200 Å$^3$.

Here, the weight average molecular weight Mw (in terms of polystyrene), number average molecular weight Mn (in terms of polystyrene), and polydispersity Mw/Mn (PDI) were calculated by GPC (solvent: THF) measurement. In addition, the composition ratio (molar ratio) was calculated by $^1$H-NMR measurement.

A-1

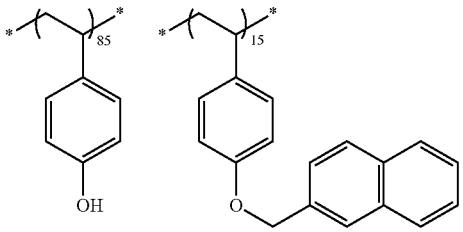

Mw 10000
PDI 1.25

-continued
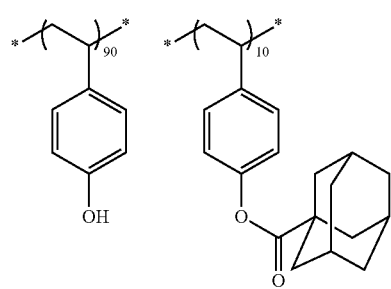
A-2
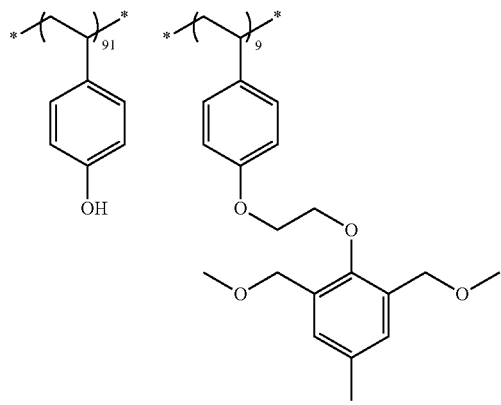
A-6
Mw 3500
PDI 1.10
Mw 3800
PDI 1.12
A-3
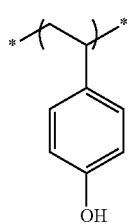
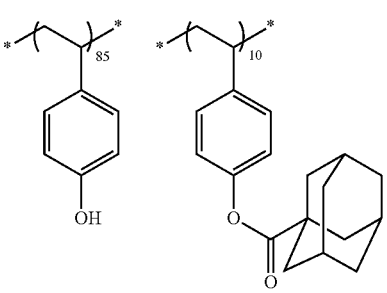
A-7
Mw 8000
PDI 1.05
A-4
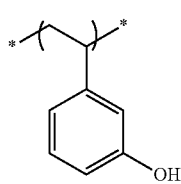
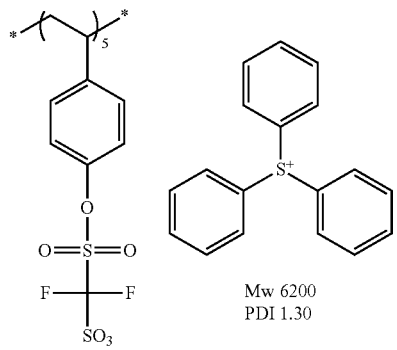
Mw 4200
PDI 1.03
Mw 6200
PDI 1.30
A-5
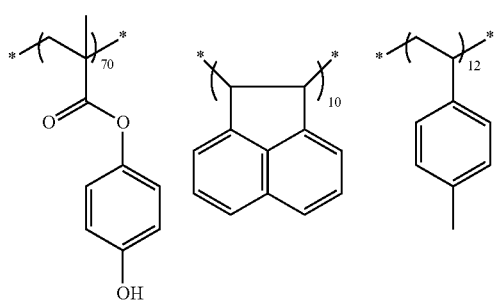
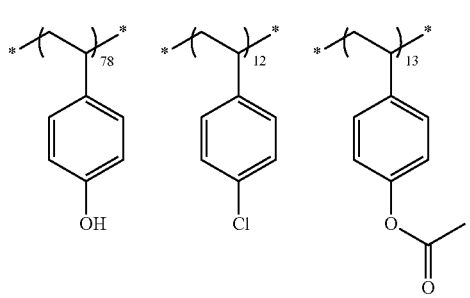
A-8
Mw 9600
PDI 1.45
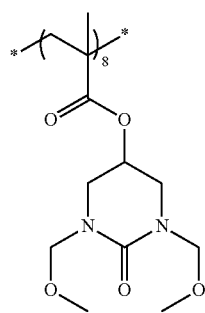
Mw 4300
PDI 1.75
[Acid Generator]
The structure of the acid generator used in Examples or Comparative Examples, and the volume value of an acid generated from the acid generator are shown below.

B-1
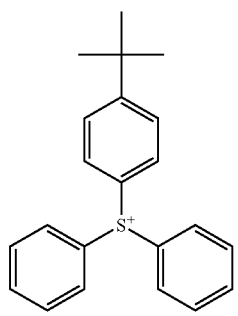 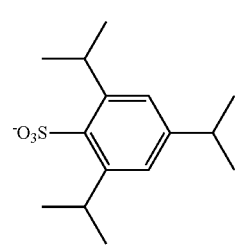
303 Å³
B-2
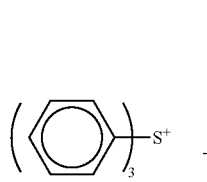 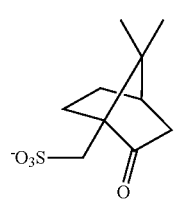
216 Å³
B-3
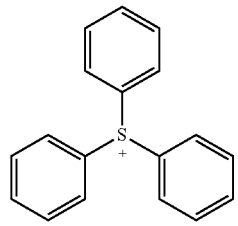 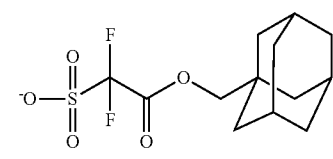
271 Å³
B-4
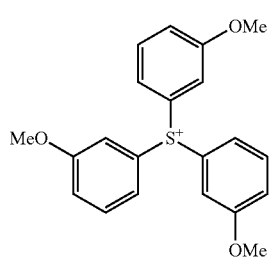 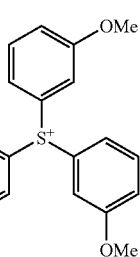 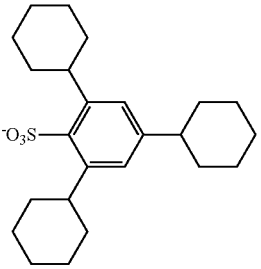
437 Å³
B-5
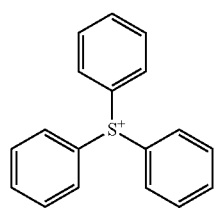 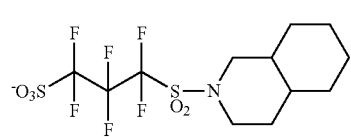
311 Å³
-continued
B-6
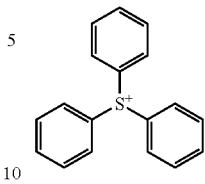 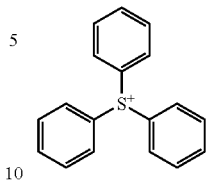
535 Å³
B-7
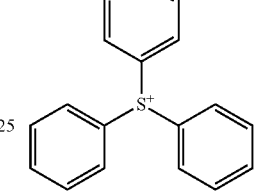 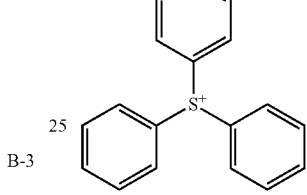
244 Å³
(Basic Compound)
As the basic compound, the following compounds were used.
N-1: Tetrabutylammonium hydroxide
N-3: Tri(n-octyl)amine
N-4: 2,4,5-triphenylimidazole
N-2
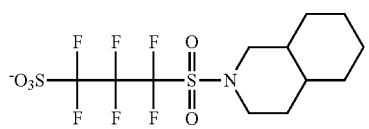
N-5
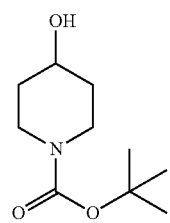

[Developer]
As the developer, the followings were used.
SG-1: Methyl amyl ketone
SG-2: Butyl acetate
SG-3: Aqueous solution of 2.38 mass % tetramethylammonium hydroxide
[Rinsing Solution]
As the rinsing solution, the followings were used.
SR-1: Methyl isobutyl carbinol
SR-2: Pure water
[Preparation of Support]
A Cr oxide-deposited 6-inch wafer (a wafer subjected to a treatment of forming a shielding film, which is used for conventional photomask blank) was prepared.
[Preparation of Resist Solution]
(Resist Solution in Example 1)

| | |
|---|---|
| Alkali-soluble resin (A-1) | 0.55 g |
| Acid generator (B-5) | 0.13 g |
| Crosslinking agent (C-1) | 0.16 g |
| Tetrabutylammonium hydroxide (N-1) | 0.002 g |
| Benzoic acid | 0.012 g |
| Surfactant PF6320 (manufactured by OMNOVA Solutions Inc.) | 0.001 g |
| Propylene glycol monomethyl ether acetate (solvent) | 4.0 g |
| Propylene glycol monomethyl ether (solvent) | 5.0 g |

A composition solution obtained by mixing the compounds above was microfiltered through a polytetrafluoroethylene filter having a pore size of 0.03 μm to obtain a resist solution.

(Resist Solution in Examples 2 to 29, and Comparative Examples 1 to 3)

The resist solutions were prepared in the same manner as in Example 1, except for components described in Table 1 below, with regard to the formulation of the resist solution.

[Preparation of Resist Film]

The resist solution was coated on the 6-inch wafer above by using a spin coater MARK 8, manufactured by Tokyo Electron Ltd. and dried on a hot plate at 110° C. for 90 seconds to obtain a resist film having a thickness of 50 nm. That is, a resist-coated mask blank was obtained.

[Production of Negative Resist Pattern]

This resist film was patternwise irradiated by using an electron beam lithography device (ELS-7500 manufactured by ELIONIX INC., accelerating voltage: 50 KeV). After the irradiation, the resist film was heated on a hot plate at 110° C. for 90 seconds, dipped in the developer described in Table 1 for 60 seconds, rinsed with the rinsing solution described in Table 1 for 30 seconds and dried.

[Evaluation]

Regarding the obtained resist solution and negative resist pattern, the pattern was evaluated for the storage stability and PEB temperature dependency according to the following methods.

(Storage Stability Evaluation)

The sample was stored at 5° C. for 30 days, and the total number of foreign materials having a size of 0.25 μm to 1.0 μm before and after the storage was measured using KL-20A Particle Counter manufactured by RION Co., Ltd., under the condition of a flow rate of 10 ml/min. The number of foreign materials before and after the storage under the above condition was expressed in terms of a ratio (number after aging-number before aging). A lower value leads to less change with aging, thus providing superior storage stability. The results are shown Table 1.

(PEB Temperature Dependency)

The condition of post exposure bake (PEB) was set to 110° C. for 90 seconds. An irradiation dose which reproduces a 1:1 line and space having a mask size of 100 nm under this condition was taken as the optimum exposure amount. Next, after the irradiation with this optimum irradiation dose, PEB was carried out at two different temperatures of the above-described PEB temperature ±2° C. (112° C., 108° C.). The length of each of the obtained line and space was measured to calculate line widths L1 and L2 thereof. PEB temperature dependency (PEBS) was defined as a variation of the line width per 1° C. of PEB temperature change, and calculated according to the following equation. The results are shown in Table 1.

PEB temperature dependency (nm/° C.)=|L1−L2|/4

A smaller value indicates less change in performance to PEB temperature variation and favorable performance.

TABLE 1

| | Resin (A) Amount added (g) | Photoacid generator (B) Amount added (g) | Crosslinking agent (C) Amount added (g) | Basic compound Amount added (g) | Developer | Rinsing solution | Particle | PEB temperature dependency (nm/° C.) |
|---|---|---|---|---|---|---|---|---|
| Example 1 | A-1 0.55 g | B-5 0.13 g | C-1 0.16 g | N-1 0.05 g | SG-3 | SR-2 | 8 | 6 |
| Example 2 | A-2 0.55 g | B-5 0.13 g | C-1 0.16 g | N-2 0.05 g | SG-3 | SR-2 | 2 | 2 |
| Example 3 | A-3 0.55 g | B-5 0.13 g | C-1 0.16 g | N-2 0.05 g | SG-3 | SR-2 | 15 | 8 |
| Example 4 | A-4 0.55 g | B-5 0.13 g | C-1 0.16 g | N-1 0.05 g | SG-3 | SR-2 | 20 | 12 |
| Example 5 | A-5 0.71 g | B-5 0.13 g | C-1 0.16 g | N-2 0.05 g | SG-3 | SR-2 | 10 | 6 |
| Example 6 | A-6 0.71 g | B-5 0.13 g | C-1 0.16 g | N-3 0.05 g | SG-3 | SR-2 | 12 | 6 |
| Example 7 | A-7 0.60 g | — | C-1 0.16 g | N-4 0.05 g | SG-3 | SR-2 | 13 | 4 |
| Example 8 | A-8 0.55 g | B-5 0.13 g | C-1 0.16 g | N-8 0.05 g | SG-3 | SR-2 | 8 | 9 |
| Example 9 | A-2 0.55 g | B-2 0.05 g | C-1 0.16 g | N-2 0.05 g | SG-3 | SR-2 | 10 | 12 |
| Example 10 | A-2 0.47 g | B-3 0.13 g | C-1 0.24 g | N-2 0.05 g | SG-3 | SR-2 | 6 | 8 |
| Example 11 | A-2 0.55 g | B-4/B-6 0.08 g/0.08 g | C-1 0.16 g | N-5 0.05 g | SG-3 | SR-2 | 4 | 6 |
| Example 12 | A-2 0.55 g | B-1 0.11 g | C-1 0.16 g | N-2 0.05 g | SG-3 | SR-2 | 6 | 13 |
| Example 13 | A-2 0.55 g | B-6 0.16 g | C-1 0.16 g | N-3 0.05 g | SG-3 | SR-2 | 13 | 13 |
| Example 14 | A-2 0.55 g | B-7 0.13 g | C-1 0.16 g | N-1 0.05 g | SG-3 | SR-2 | 10 | 2 |
| Example 15 | A-1 0.55 g | B-5 0.13 g | C-2 0.16 g | N-9 0.05 g | SG-3 | SR-2 | 12 | 10 |
| Example 16 | A-1 0.55 g | B-5 0.13 g | C-3 0.16 g | N-2 0.05 g | SG-3 | SR-2 | 16 | 12 |
| Example 17 | A-1 0.55 g | B-5 0.13 g | C-4 0.16 g | N-9 0.05 g | SG-3 | SR-2 | 16 | 6 |
| Example 18 | A-1 0.55 g | B-5 0.13 g | C-5 0.16 g | N-3 0.05 g | SG-3 | SR-2 | 24 | 16 |
| Example 19 | A-1 0.55 g | B-7 0.13 g | C-1 0.16 g | N-4 0.05 g | SG-3 | SR-2 | 6 | 6 |
| Example 20 | A-2/A-3 0.20 g/0.51 g | B-5 0.13 g | C-1 0.16 g | N-6 0.05 g | SG-3 | SR-2 | 8 | 6 |
| Example 21 | A-1 0.55 g | B-7 0.13 g | C-1/CL-1 0.12 g/0.04 g | N-7 0.05 g | SG-3 | SR-2 | 4 | 6 |
| Example 22 | A-1 0.55 g | B-7 0.13 g | C-1/CL-2 0.12 g/0.04 g | N-8 0.05 g | SG-3 | SR-2 | 9 | 8 |
| Example 23 | A-1 0.55 g | B-5 0.13 g | C-1 0.16 g | N-1 0.05 g | SG-1 | SR-1 | 4 | 5 |
| Example 24 | A-1 0.55 g | B-5 0.13 g | C-1 0.16 g | N-1 0.05 g | SG-2 | SR-1 | 6 | 6 |
| Example 25 | A-1 0.55 g | B-5 0.13 g | C-1 0.16 g | N-3 0.05 g | SG-3 | SR-2 | 9 | 4 |
| Example 26 | A-2 0.55 g | B-5 0.13 g | C-1 0.16 g | N-4 0.05 g | SG-3 | SR-2 | 10 | 6 |
| Example 27 | A-1 0.55 g | B-5 0.13 g | C-1 0.16 g | N-5 0.05 g | SG-3 | SR-2 | 8 | 9 |
| Example 28 | A-2 0.55 g | B-5 0.13 g | C-1 0.16 g | N-6 0.05 g | SG-3 | SR-2 | 6 | 10 |
| Example 29 | A-1 0.55 g | B-5 0.13 g | C-1 0.16 g | N-7 0.05 g | SG-3 | SR-2 | 7 | 6 |
| Comparative Example 1 | A-1 0.55 g | B-5 0.13 g | CR-1 0.16 g | N-1 0.05 g | SG-3 | SR-2 | 448 | 25 |
| Comparative Example 2 | A-1 0.55 g | B-5 0.13 g | CR-2 0.16 g | N-1 0.05 g | SG-3 | SR-2 | 589 | 42 |
| Comparative Example 3 | A-1 0.55 g | B-5 0.13 g | CR-3 0.16 g | N-1 0.05 g | SG-3 | SR-2 | 750 | 60 |

What is claimed is:

1. An actinic ray-sensitive or radiation-sensitive resin composition comprising:
   an alkali-soluble resin;
   a crosslinking agent; and
   a compound capable of generating an acid upon irradiation with actinic rays or radiation,
   wherein the crosslinking agent is represented by the following General Formula (I),

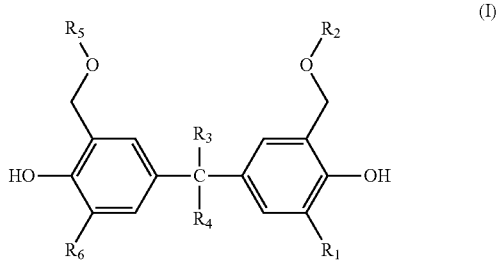

(I)

wherein in General Formula (I),
each of $R_1$ and $R_6$ independently represents a hydrocarbon group having 5 or less carbon atoms,
each of $R_2$ and $R_5$ independently represents an alkyl group, a cycloalkyl group, an aryl group, or an acyl group,
$R_3$ and $R_4$ are bonded to each other to form a ring which is an aromatic or non-aromatic hydrocarbon ring, an aromatic or non-aromatic heterocyclic ring, or a polycyclic fused ring formed by a combination of two or more rings thereof,
the ring formed by $R_3$ and $R_4$ may have a substituent which is at least one selected from the group consisting of an alkyl group, a cycloalkyl group, an alkoxy group, a carboxyl group, an aryl group, an acyl group, an alkoxycarbonyl group, a nitro group, halogen, and a hydroxy group, the alkali-soluble resin includes a repeating unit represented by the following General Formula (4),

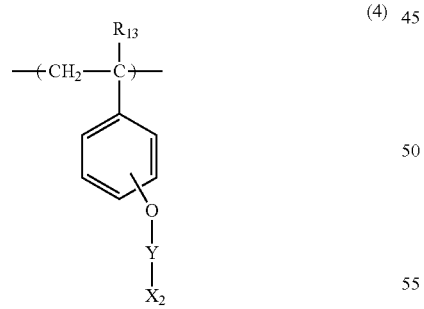

(4)

wherein in General Formula (4),
$R_{13}$ represents a hydrogen atom or a methyl group,
Y represents a single bond or a divalent linking group, and
$X_2$ represents a non-acid-decomposable hydrocarbon group, the hydrocarbon group being a chain-like or branched hydrocarbon group, a phenyl group, or a naphthyl group, and
the content of the cross-linking agent is 10 mass% or more based on the solids content of the actinic ray-sensitive or radiation-sensitive.

2. The actinic ray-sensitive or radiation-sensitive resin composition according to claim 1, wherein $R_3$ and $R_4$ in General Formula (I) are bonded to each other to form a ring represented by the following General Formula (I-a),

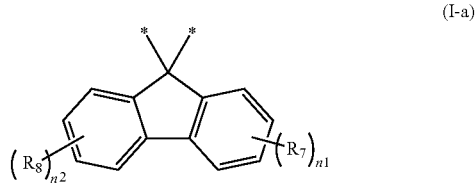

(I-a)

wherein in General Formula (I-a),
each of $R_7$ and $R_8$ independently represents the substituent,
each of n1 and n2 independently represents an integer of 0 to 4, and
* indicates a connecting site to the phenolic nucleus.

3. The actinic ray-sensitive or radiation-sensitive resin composition according to claim 1, wherein the compound capable of generating an acid upon irradiation with actinic rays or radiation is an onium salt.

4. The actinic ray-sensitive or radiation-sensitive resin composition according to claim 1, wherein the compound capable of generating an acid upon irradiation with actinic rays or radiation is a compound capable of generating an acid represented by the following General Formula (IIIB) or (IVB),

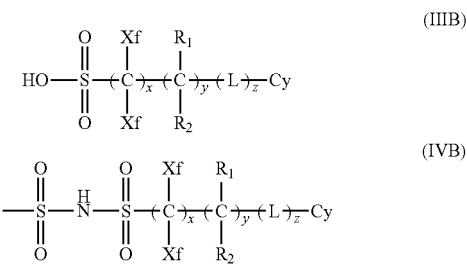

wherein in General Formula (TIM),
each Xf independently represents a fluorine atom, or an alkyl group substituted with at least one fluorine atom,
each of $R_1$ and $R_2$ independently represents a hydrogen atom, or an alkyl group,
each L independently represents a divalent linking group,
Cy represents a cyclic organic group, and
x represents an integer of 1 to 20, y represents an integer of 0 to 10, and z represents an integer of 0 to 10, and
in General Formula (IVB),
each Xf independently represents a fluorine atom, or an alkyl group substituted with at least one fluorine atom,
each of $R_1$ and $R_2$ independently represents a hydrogen atom, or an alkyl group,
each L independently represents a divalent linking group,
Cy represents a cyclic organic group,
Rf represents a group containing a fluorine atom, and
x represents an integer of 1 to 20, y represents an integer of 0 to 10, and z represents an integer of 0 to 10.

5. An actinic ray-sensitive or radiation-sensitive film formed using the actinic ray-sensitive or radiation-sensitive resin composition according to claim 1.

6. A mask blank provided with the actinic ray-sensitive or radiation-sensitive film according to claim 5.

7. A photomask produced by a method including exposing the actinic ray-sensitive or radiation-sensitive film provided in the mask blank according to claim 6, and developing the exposed actinic ray-sensitive or radiation-sensitive film.

8. A pattern forming method, comprising:

forming an actinic ray-sensitive or radiation-sensitive film using the actinic ray-sensitive or radiation-sensitive resin composition according to claim 1;

exposing the film; and developing the exposed film using a developer to form a pattern.

9. The pattern forming method according to claim 8, wherein the exposure is carried out using X-rays, an electron beam, or EUV.

10. A method for manufacturing an electronic device, comprising the pattern forming method according to claim 8.

11. The actinic ray-sensitive or radiation-sensitive resin composition according to claim 1, wherein in General Formula (4), $X_2$ represents a chain-like or branched hydrocarbon group having 1 to 20 carbon atoms.

12. The actinic ray-sensitive or radiation-sensitive resin composition according to claim 1, wherein in General Formula (4), $X_2$ represents a propyl group, an isopropyl group, an n-butyl group, an s-butyl group, an isobutyl group, a pentyl group, an isopentyl group, a neopentyl group, a hexyl group, a 2-ethylhexyl group, or an octyl group.

13. The actinic ray-sensitive or radiation-sensitive resin composition according to claim 1, wherein in General Formula (4), $X_2$ represents a group having a plurality of monocyclic alicyclic hydrocarbon groups, and the monocyclic alicyclic hydrocarbon groups are at least two selected from the group consisting of a cyclopropyl group, a cyclopentyl group, a cyclohexyl group, a cyclobutyl group, and a cyclooctyl group.

14. The actinic ray-sensitive or radiation-sensitive resin composition according to claim 1, wherein in General Formula (I), each of $R_1$ and $R_6$ independently represents an unsubstituted hydrocarbon group having 5 or less carbon atoms.

15. The actinic ray-sensitive or radiation-sensitive resin composition according to claim 1, wherein the crosslinking agent is the following compound C-1 or C-4:

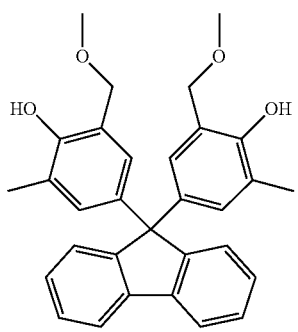

C-1

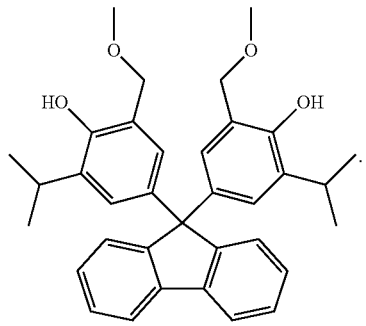

C-4

16. The actinic ray-sensitive or radiation-sensitive resin composition according to claim 1, wherein the alkali-soluble resin further includes a repeating unit represented by the following General Formula (Q-1),

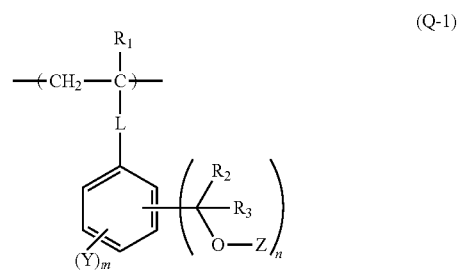

(Q-1)

wherein in General Formula (Q-1), $R_1$ represents a hydrogen atom, a methyl group, or a halogen atom, $R_2$ and $R_3$ represent a hydrogen atom, an alkyl group, or a cycloalkyl group, L represents a divalent linking group or a single bond, Y represents a monovalent substituent except for a methylol group, Z represents a hydrogen atom or substituent, m represents an integer of 0 to 4, n represents an integer of 1 to 5, m+n is 5 or less, in the case where m is 2 or more, plural Y's may be the same as or different from each other, in the case where n is 2 or more, plural $R_2$'s, $R_3$'s, and Z's may be the same as or different from each other, and any two or more of Y, $R_2$, $R_3$, and Z may be bonded to each other to form a ring structure.

17. An actinic ray-sensitive or radiation-sensitive resin composition comprising:

an alkali-soluble resin;

a crosslinking agent represented by the following General Formula (I-b); and a compound capable of generating an acid upon irradiation with actinic rays or radiation,

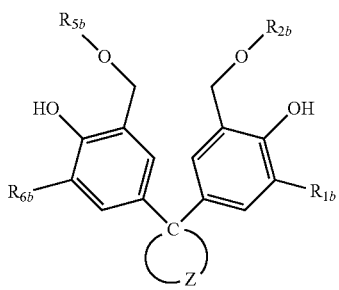

(I-b)

wherein in General Formula (I-b), each of $R_{1b}$ and $R_{6b}$ independently represents an unsubstituted alkyl group having 5 or less carbon atoms, each of $R_{2b}$ and $R_{5b}$ independently represents an alkyl group having 6 or less carbon atoms or a cycloalkyl group having 3 to 12 carbon atoms, and Z represents an atomic group necessary for forming a ring together with the carbon atom in General Formula (I-b), and the ring includes a fluorene structure represented by the following General Formula (I-a):

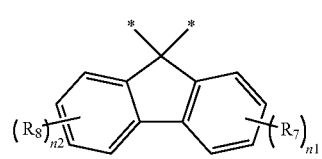

(I-a)

wherein in General Formula (I-a), each of $R_7$ and $R_8$ independently represents a substituent which is at least one selected from the group consisting of an alkyl group, a cycloalkyl group, an alkoxy group, a carboxyl group, an aryl group, an acyl group, an alkoxycarbonyl group, a nitro group, halogen, and a hydroxy group, each of n1 and n2 independently represents an integer of 0 to 4, and

*indicates a connecting site to the phenolic nucleus.

18. The actinic ray-sensitive or radiation-sensitive resin composition according to claim 17, wherein the crosslinking agent is the following compound C-1 or C-4:

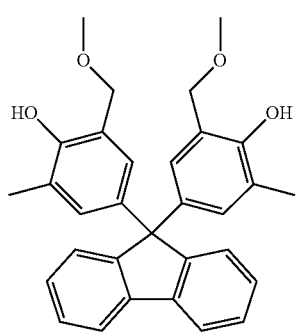

C-1

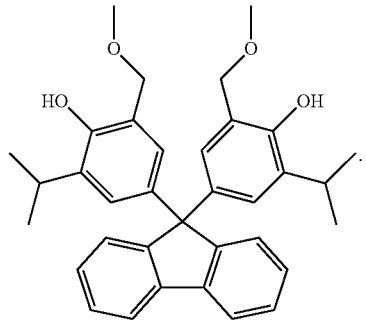

C-4

19. The actinic ray-sensitive or radiation-sensitive resin composition according to claim 17, wherein the cross-linking agent is the following compound C-1, C-2, C-3, C-4, or C-5:

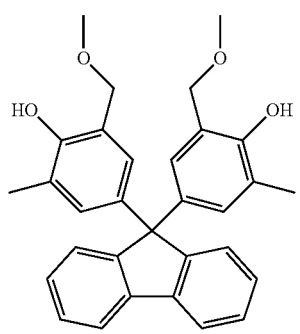

C-1

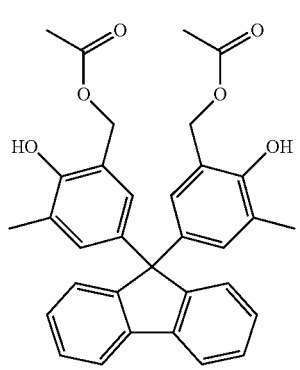

C-2

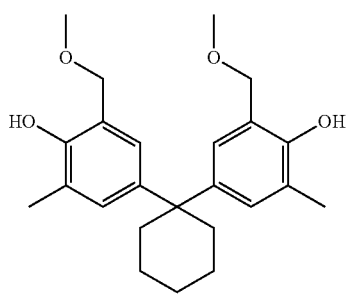

C-3

-continued
C-4
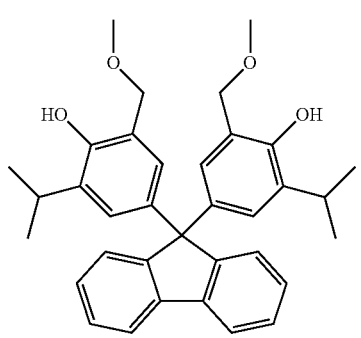
C-5
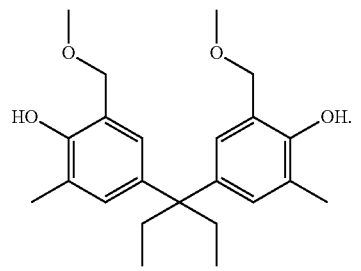
20. The actinic ray-sensitive or radiation-sensitive resin composition according to claim 19, wherein the crosslinking agent is the compound C-1.